(12) United States Patent
Burgard et al.

(10) Patent No.: US 9,932,611 B2
(45) Date of Patent: *Apr. 3, 2018

(54) MICROORGANISMS AND METHODS FOR ENHANCING THE AVAILABILITY OF REDUCING EQUIVALENTS IN THE PRESENCE OF METHANOL, AND FOR PRODUCING SUCCINATE RELATED THERETO

(71) Applicant: Genomatica, Inc., San Diego, CA (US)

(72) Inventors: Anthony P. Burgard, Bellefonte, PA (US); Robin E. Osterhout, San Diego, CA (US); Stephen J. Van Dien, Encinitas, CA (US); Cara Ann Tracewell, Solana Beach, CA (US); Priti Pharkya, San Diego, CA (US); Stefan Andrae, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/059,285

(22) Filed: Oct. 21, 2013

(65) Prior Publication Data

US 2014/0235815 A1 Aug. 21, 2014

Related U.S. Application Data

(60) Provisional application No. 61/717,001, filed on Oct. 22, 2012, provisional application No. 61/766,642, filed on Feb. 19, 2013.

(51) Int. Cl.
| | |
|---|---|
| *C12P 7/46* | (2006.01) |
| *C07C 55/10* | (2006.01) |
| *C08G 63/00* | (2006.01) |
| *C12N 15/70* | (2006.01) |
| *C12N 15/81* | (2006.01) |
| *C12P 7/24* | (2006.01) |
| *C12N 9/04* | (2006.01) |
| *C12N 9/06* | (2006.01) |
| *C12N 9/10* | (2006.01) |
| *C07C 59/235* | (2006.01) |
| *C12N 15/74* | (2006.01) |
| *C12N 15/77* | (2006.01) |

(52) U.S. Cl.
CPC ............... *C12P 7/46* (2013.01); *C07C 55/10* (2013.01); *C07C 59/235* (2013.01); *C08G 63/00* (2013.01); *C12N 9/0006* (2013.01); *C12N 9/0028* (2013.01); *C12N 9/1007* (2013.01); *C12N 15/70* (2013.01); *C12N 15/74* (2013.01); *C12N 15/77* (2013.01); *C12N 15/81* (2013.01); *C12N 15/815* (2013.01); *C12P 7/24* (2013.01); *C12Y 101/01244* (2013.01); *C12Y 105/0102* (2013.01)

(58) Field of Classification Search
CPC .. C12N 9/1007; C12N 9/0006; C12N 9/0028; C12N 15/70; C12N 15/81; C12Y 101/01244; C12Y 105/10
See application file for complete search history.

(56) References Cited

U.S. PATENT DOCUMENTS

| | | | |
|---|---|---|---|
| 7,127,379 B2 | 10/2006 | Palsson et al. | |
| 7,973,222 B1* | 7/2011 | Izui ................. | C12N 15/8259 800/288 |
| 2002/0012939 A1 | 1/2002 | Palsson et al. | |
| 2002/0168654 A1 | 11/2002 | Clow et al. | |
| 2003/0059792 A1 | 3/2003 | Negin et al. | |
| 2003/0119155 A1* | 6/2003 | Yasueda ............ | C12P 13/08 435/115 |
| 2003/0224363 A1 | 12/2003 | Park et al. | |
| 2003/0233218 A1 | 12/2003 | Schilling et al. | |
| 2004/0009466 A1 | 1/2004 | Maranas et al. | |
| 2004/0029149 A1 | 2/2004 | Palsson et al. | |
| 2004/0072723 A1 | 4/2004 | Palsson et al. | |
| 2005/0053825 A1* | 3/2005 | Sakai ................. | H01M 8/16 429/401 |
| 2005/0208634 A1* | 9/2005 | Usuda ................ | C07K 14/195 435/106 |
| 2007/0184539 A1* | 8/2007 | San .................... | C12P 7/46 435/136 |
| 2009/0047719 A1* | 2/2009 | Burgard ............. | C12P 7/18 435/158 |
| 2009/0075351 A1* | 3/2009 | Burk ................. | C12N 9/0006 435/141 |
| 2010/0068773 A1* | 3/2010 | Marx ................. | C12N 9/001 435/135 |

(Continued)

FOREIGN PATENT DOCUMENTS

| | | | | |
|---|---|---|---|---|
| EP | 0 066 994 | * 12/1982 | ............ | C12N 15/00 |
| EP | 0066994 | 12/1982 | | |

(Continued)

OTHER PUBLICATIONS

US 8,236,539, 08/2012, Burgard et al. (withdrawn)
Converti, A., et al., 2002, "Use of carbon and energy balances in the study of the anaerobic metabolism of Enterobacter aerogenes at variable starting glucose concentrations", Applied Microbiology and Biotechnology, vol. 59, Nos. 2-3, pp. 303-309.*
Goenrich et al., 2005, Formaldehyde activating enzyme (Fae) and hexulose-6-phosphate synthase (Hps) in Methanosarcina barkeri : a possible function in ribose-5-phosphate biosynthesis, Archives of Microbiology, vol. 148, No. 1, pp. 41-48.*

(Continued)

*Primary Examiner* — Anand U Desai
(74) *Attorney, Agent, or Firm* — Jones Day

(57) ABSTRACT

Provided herein is a non-naturally occurring microbial organism having a methanol metabolic pathway that can enhance the availability of reducing equivalents in the presence of methanol. Such reducing equivalents can be used to increase the product yield of organic compounds produced by the microbial organism, such as succinate. Also provided herein are methods for using such an organism to produce succinate.

19 Claims, 4 Drawing Sheets

(56) References Cited

U.S. PATENT DOCUMENTS

| | | | | |
|---|---|---|---|---|
| 2010/0068774 A1* | 3/2010 | Fukui | ................ | C12P 7/46 435/145 |
| 2010/0291644 A1* | 11/2010 | Marx | ................ | C12N 9/001 435/135 |
| 2011/0045575 A1* | 2/2011 | Van Dien | ................ | C12P 7/18 435/252.33 |
| 2011/0129899 A1* | 6/2011 | Haselbeck | ................ | C12P 7/18 435/243 |
| 2011/0129904 A1 | 6/2011 | Burgard et al. | | |
| 2011/0207189 A1 | 8/2011 | Burgard et al. | | |
| 2011/0217742 A1* | 9/2011 | Sun | ................ | C12N 1/20 435/126 |
| 2012/0003652 A1 | 1/2012 | Reeves et al. | | |
| 2013/0034884 A1* | 2/2013 | Burgard | ................ | C12N 15/52 435/126 |
| 2014/0030779 A1* | 1/2014 | Pharkya | ................ | C12N 15/63 435/146 |
| 2016/0083752 A1* | 3/2016 | Burgard | ................ | C07C 55/10 523/222 |

FOREIGN PATENT DOCUMENTS

| | | |
|---|---|---|
| WO | WO 02/055995 | 7/2002 |
| WO | WO 03/106998 | 12/2003 |

OTHER PUBLICATIONS

De Schutter, K., et al., 2009, "Genome sequence of the recombinant protein production host Pichia pastoris", Nature Biotechnology, vol. 27, No. 6, pp. 561-566, inluding three further pages of on-line published methods.*

Orencio-Trejo, M., et al., 2010, "Engineering the Escherichia coli fermentative metabolism", Advances in Biochemical Engineering/Biotechnology, vol. 121 (Biosystems Engineering II), No. 1, pp. 71-107.*

Yim, H., et al., 2011, "Metabolic engineering of Escherichia coli for direct production of 1,4-butanediol", Nature Chemical Biology, vol. 7, pp. 445-452.*

Chen, N.H., et al., 2012, "A glutathione-dependent detoxification system is required for formaldehyde resistance and optimal survival of Neisseria meningitidis in biofilms", Antioxidants & Redox Signaling, vol. 18, No. 7, pp. 743-755.*

Publication date information for Chen, N.H., et al., 2012, Antioxidants & Redox Signaling, vol. 18, No. 7, pp. 743-755.*

Witthoff, S., et al., 2013, "C1 metabolism in Corynebacterium glutamicum: an endogenous pathway for oxidation of methanol to carbon dioxide", Applied and Environmental Microbiology, vol. 79, No. 22, pp. 6974-6983.*

Becker, J., et al., published online Jul. 9, 2013, "Systems-wide analysis and engineering of metabolic pathway fluxes in biosuccinate producing Basfia succiniciproducens", Biotechnology and Bioengineering, vol. 110, No. 11, pp. 3013-3023.*

International Search Report—ISA-210—for PCT/US2013/065887, dated Jan. 31, 2014, three pages.*

Inui, M., et al., 2004, "Metabolic analysis of Corynebacterium glutamicum during lactate and succinate productions under oxygen deprivation conditions", Journal of Molecular Microbiology and Biotechnology, vol. 7, No. 4, pp. 182-196.*

Ito, K., et al., 1994, "Cloning and high-level expression of the glutathione-Independent formaldehyde dehydrogenase gene from Pseudomonas putida," Journal of Bacteriology, vol. 176, No. 9, pp. 2483-2491.*

Vorholt, J. A., 2002, "Co-factor-dependent pathways of formaldehyde oxidation in methylotrophic bacteria", Archives of Microbiology, vol. 178, pp. 239-249.*

Song, H., et al., 2007, "Effects of dissolved CO2 levels on the growth of Mannheimia succiniciproducens and succinic acid production", Biotechnology and Bioengineering, vol. 98, pp. 1296-1304.*

Liu, R., et al., 2013, "CO2 fixation for succinic acid production by engineered Escherichia coli co-expressing pyruvate carboxylase and nicotinic acidphosphoribosyltransferase", Biochemical Engineering Journal, vol. 79, pp. 77-83.*

U.S. Appl. No. 13/975,678, filed Aug. 26, 2013, 2014-0058056, Chowdhury, Iqbal Hossain, Microorganisms and Methods for Enhancing the Availability of Reducing Equivalents in the Presence of Methanol, and for Producing 1,4-Butanediol Related Thereto, Pending.

U.S. Appl. No. 14/107,832, filed Dec. 16, 2013, 2014-0329916, Fronda, Christian L., Microorganisms and Methods for Enhancing the Availability of Reducing Equivalents in the Presence of Methanol, and for Producing Adipate, 6-Aminocaproate, Hexamethylenediamine or Caprolactam Related Thereto, Pending.

U.S. Appl. No. 14/071,339, filed Nov. 4, 2013, 2014-0288254, Nashed, Nashaat T., Microorganisms and Methods for Enhancing the Availability of Reducing Equivalents in the Presence of Methanol, and for Producing 3-Hydroxyisobutyrate or Methacrylic Acid Related Thereto, Allowed.

U.S. Appl. No. 14/071,318, filed Nov. 4, 2013, 2014-0302575, Ekstrom, Richard C., Microorganisms and Methods for Enhancing the Availability of Reducing Equivalents in the Presence of Methanol, and for Producing 1,2-Propanediol, n-Propanol, 1,3-Propanediol, or Glycerol Related Thereto, Pending.

U.S. Appl. No. 14/424,404, filed Feb. 26, 2015, 2015-0203875, Saidha, Tekchand, Microorganisms and Methods for Enhancing the Availability of Reducing Equivalents in the Presence of Methanol, and for Producing 1.4-Butanediol Related Thereto, Pending.

U.S. Appl. No. 14/652,727, filed Jun. 16, 2015, 2015-0329885, Kim, Alexander D., Microorganisms and Methods for Enhancing the Availability of Reducing Equivalents in the Presence of Methanol, and for Producing Adipate, 6-Aminocaproate Hexamethylenediamine or Caprolactam Related Thereto, Pending.

PCT/US13/68265, Nov. 4, 2013, Unpublished, Microorganisms and Methods for Enhancing the Availability of Reducing Equivalents in the Presence of Methanol, and for Producing 3-Hydroxyisobutyrate or Methacrlic Acid Related Thereto, Pending.

PCT/US13/68264, Nov. 4, 2013, Unpublished, Microorganisms and Methods for Enhancing the Availability of Reducing Equivalents in the Presence of Methanol, and for Producing 1,2-Propanediol, N-Propanol, 1,3-Propanediol, or Glycerol Related Thereto, Pending.

U.S. Appl. No. 14/436,722, filed Apr. 17, 2015, Unpublished, Microorganisms and Methods for Enhancing the Availability of Reducing Equivalents in the Presence of Methanol, and for Producing Succinate Related Thereto, Pending.

Abdel-Hamid et al., "Pyruvate oxidase contributes to the aerobic growth efficiency of Escherichi coli," Microbiol 147:1483-98 (2001).

Andreesen and Ljungdahl, "Formate Dehydrogenase of Clostridium thermoaceticum: Incorporation of Selenium-75, and the Effects of Selenite, Molybate, and Tungstate on the Enzyme," J. Bacteriol. 116(2):867-873 (1973).

Arikawa et al., "Soluble fumarate reductase isoenzymes from Saccharomyces cerevisiae are required for anaerobic growth," FEMS Microbiol. Lett. 165:111-116 (1998).

Arps et al., "Genetics of Serine Pathway Enzymes in Methylobacterium extorquens AM1: Phosphoenolpyruvate Carboxylase and Malyl Coenzyme A Lyase," J. Bacteriol. 175(12):3776-3783 (1993).

Atteia et al., "Pyruvate formate-lyase and a novel route of eukaryotic ATP synthesis in Chlamydomonas mitochondria," J. Biol. Chem. 281:9909-9918 (2006).

Bakker et al., "Stoichiometry and compartmentation of NADH metabolism in Saccharomyces cerevisiae," FEMS Microbiol. Rev. 25:15-37 (2001).

Beopoulos et al., "Control of Lipid Accumulation in the Yeast Yarrowia lipolytica," AEM 74:7779-89 (2008).

Bergquist and Gibbs, "Degenerate oligonucleotide gene shuffling," Methods Mol. Biol. 352:191-204 (2007).

(56) References Cited

OTHER PUBLICATIONS

Bergquist et al., "Degenerate oligonucleotide gene shuffling (DOGS) and random drift mutagenesis (RNDN): two complementary techniques for enzyme evolution," Biomol. Eng. 22:63-72 (2005).
Bernhard et al., "Functional and structural role of the cytochrome b subunit of the membrane-bound hydrogenase complex of Alcaligenes eutrophus H16," Eur. J. Biochem. 248, 179-186 (1997).
Blaschkowski et al., "Routes of Flavodoxin and Ferredoxin Reduction in Escherichia coli," Eur. J. Biochem. 123:563-569 (1982).
Boles et al., "Characterization of a glucose-repressed pyruvate kinase (Pyk2p) in Saccharomyces cerevisiae that is catalytically insensitive to fructose-1,6-bisphosphate," J. Bacteriol. 179:2987-2993 (1997).
Bose et al., "Genetic analysis of the methanol- and methylamine-specific methyltransferase 2 genes of Methanosarcina acetivorans C2A," J. Bacteriol. 190(11):4017-4026 (2008).
Bozzi et al., "Structural and biochemical studies of alcohol dehydrogenase isozymes from Kluyveromyces lactis," Biochim. Biophys. Acta 1339:133-142 (1997).
Bricker et al., "A mitochondrial pyruvate carrier required for pyruvate uptake in yeast, Drosophila, and humans," Science 337:96-100 (2012).
Burgard et al., "Optknock: a bilevel programming framework for identifying gene knockout strategies for microbial strain optimization," Biotechnol. Bioeng. 84(6):647-657 (2003).
Burgard et al., "Minimal Reaction Sets for Escherichia coli Metabolism under Different Growth Requirements and Uptake Environments," Biotechnol. Prog. 17:791-797 (2001).
Burgdorf, "The Soluble NAD-Reducing [NiFe]-Hydrogenase from Ralstonia eutropha H16 Consists of Six Subunits and Can Be Specifically Activated by NADPH," J. Bact. 187(9) 3122-3132(2005).
Burke et al., "The Isolation, Characterization, and Sequence of the Pyruvate Kinase Gene of Saccharomyces cerevisiae," J. Biol. Chem. 258(4):2193-2201 (1983).
Chandra Raj et al., "Pyruvate decarboxylase: a key enzyme for the oxidative metabolism of lactic acid by Acetobacter pasteruianus," Arch. Microbiol. 176:443-451 (2001).
Chen et al., "Phosphoenolpyruvate carboxykinase assayed at physiological concentrations of metal ions has a high affinity for $CO_2$," Plant Physiol. 128:160-164 (2002).
Clark and Ljungdahl, "Purification and Properties of 5,10-Methylenetetrahydrofolate Reductase, an Iron-sulfur Flavoprotein from Clostridium formicoaceticum," J. Biol. Chem. 259(17)10845-10849 (1984).
Coco et al., "DNA shuffling method for generating highly recombined genes and evolved enzymes," Nat. Biotechnol. 19(4):354-359 (2001).
Colonna et al., "Synthesis and radiocarbon evidence of terephthalate polyesters completely prepared from renewable resources," Green Chemistry, 13:2543-2548 (2011).
Coppi, "The hydrogenases of Geobacter sulfurreducens: a comparative genomic perspective," Microbiology 151, 1239-1254 (2005).
Cotelesage et al., "How does an enzyme recognize $CO_2$?," Int. J. Biochem. Cell Biol. 39:1204-1210 (2007).
Cracknell, et al., "A kinetic and thermodynamic understanding of O2 tolerance in [NiFe]-ydrogenases," Proc Nat Acad Sci, 106(49) 20681-20686 (2009).
Currie et al., "Authentication and dating of biomass components of industrial materials; links to sustainable technology," Nuclear Instruments and Methods in Physics Research B, 172:281-287 (2000).
Daniel et al., "Biochemical and molecular characterization of the oxidative branch of glycerol utilization by Citrobacter freundii," JBac 177(15):4392-4401 (1995).
D'Ari and Rabinowitz, "Purification Characterization, cloning, and Amino Acid Sequence of the Bifunctional Enzyme 5,10-Methylenetetrahydrofolate Dehydrogenase/5,10-Methenyltetrahydrofolate Cyclohydrolase from Escherichia coli," J. Biol. Chem. 266(35):23953-23958 (1991).
Das et al., "Characterization of a corrinoid protein involved in the C1 metabolism of strict anaerobic bacterium Moorella thermoacetica," Proteins 67(1):167-176 (2007).
de Bok et al., "Two W-containing formate dehydrogenases (CO2-reductases) involving syntrophic propionate oxidation by Syntrophobacter fumaroxidans," Eur. J. Biochem. 270:2476-2485 (2003).
de Graes et al., "The steady-state internal redox state (NADH/NAD) reflects the external redox state and is correlated with catabolic adaptation in Escherichia coli," J. Bacteriol. 181:2351-2357 (1999).
de Smidt et al., "The alcohol dehydrogenases of Saccharomyces cerevisiae: a comprehensive review," FEMS Yeast Rev. 7:967-978 (2008).
Drake and Daniel, " Physiology of the thermophilic acetogen Moorella thermoacetica," Res. Microbiol. 155:869-883 (2004).
Drake, H. L., "Demonstration of Hydrogenase in Extracts of the Homoacetate-Fermenting Bacterium Clostridium thermoaceticum," J. Bacteriol. 150:702-709 (1982).
Drewke et al., "Ethanol formation in adh) mutants reveals the existence of a novel acetaldehyde-reducing activity in Saccharomyces cerevisiae," J. Bacteriol. 172:3909-3917 (1990).
Eikmanns et al., "The phosphoenolpyruvate carboxylase gene of Corynebacterium glutamicum: Molecular cloning, nucleotide sequence, and expression." Mol. Gen. Genet. 218:330-339 (1989).
Enomoto et al., "Cloning and sequencing of the gene encoding the soluble fumarate reductase from Saccharomyces cerevisiae," DNA Res. 3:263-267 (1996).
Fan et al., "Disruption of a gene encoding glycerol 3-phosphatase from Candida albicans impairs intracellular glycerol accumulation-mediated salt-tolerance," FEMS Microbiol. Lett. 245:107-116 (2005).
Fox et al., "Characterization of the Region Encoding the CO-Induced Hydrogenase of Rhodospirillum rubrum," J Bacteriol. 178:6200-6208 (1996).
Fuchs, "Alternative pathways of carbon dioxide fixation: insights into the early evolution of life?," Annu. Rev. Microbiol. 65:631-658 (2011).
Fujii et al., "Error-prone rolling circle amplification: the simplest random mutagenesis protocol," Nat. Protoc. 1(5):2493-2497 (2006).
Fujii et al., "One-step random mutagenesis by error-prone rolling circle amplification," Nucleic Acids Res. 32(19):e145 (2004).
Fujinaga and Meyer, "Cloning and Expression in Escherichia coli of the Gene Encoding the [2Fe—2S] Ferredoxin from Clostridium Pasteurianum," Biochemical and Biophysical Research Communications, 192(3):1115-1122 (1993).
Galagan et al., "The genome of M. acetivorans reveals extensive metabolic and physiological diversity," Genome Res. 12(4):532-542 (2002).
Garcia-Alles et al., "Phosphoenolpyruvate- and ATP-dependent dihydroxyacetone kinases: covalent substrate-binding and kinetic mechanism.," Biochemistry, 43(41):13037-45 (2004).
Germer, "Overexpression, Isolation, and Spectroscopic Characterization of the Bidirectional [NiFe] Hydrogenase from Synechocystis sp. PCC 6803," J. Biol. Chem. 284(52), 36462-36472 (2009).
Gibbs et al., "Degenerate oligonucleotide gene shuffling (DOGS): a method for enhancing the frequency of recombination with family shuffling," Gene. 271:13-20 (2001).
Gibson and McAlister-Henn, "Physical and genetic interactions of cytosolic malate dehydrogenase with other gluconeogenic enzymes," J. Biol. Chem. 278:25628-25636 (2003).
Goenrich, et al., "A glutathione-dependent formaldehyde-activating enzyme (Gfa) from Paracoccus denitrificans detected and purified via two-dimensional proton exchange NMR spectroscopy," J Biol Chem 277(5);3069-72 (2002).
Guest et al., "The fumarase genes of Escherichia coli: location of the fumB gene and discovery of a new gene (fumC)," J. Gen. Microbiol. 131(11):2971-2984 (1985).
Gutknecht et al., "The dihydroxyacetone kinase of Escherichia coli utilizes a phosphoprotein instead of ATP as phosphoryl donor," EMBO J. 20(10):2480-2486 (2001).

(56) References Cited

OTHER PUBLICATIONS

Guzman et al., "Tight regulation, modulation, and high-level expression by vectors containing the arabinose PBAD promoter," *J. Bacteriol.* 177:4121-4130 (1995).
Hagemeier et al., "Insight into the mechanism of biological methanol activation based on the crystal structure of the methanol-cobalamin methyltransferase complex," Proc. Natl. Acad. Sci. U.S.A. 103(50):18917-18922 (2006).
Harms and Thauer, "Methylcobalamin: Coenzyme M methyltransferase isoenzymes MtaA and MtbA from Methanosarcina barkeri. Cloning, sequencing and differential transcription of the encoding genes, and functional overexpression of the mtaA gene in *Escherichia coli*," Eur. J. Biochem. 235(3):653-659 (1996).
Hayes et al., "Combining computational and experimental screening for rapid optimization of protein properties," Proc. Natl. Acad. Sci. U.S.A. 99(25):15926-15931 (2002).
Heggeset, et al., "Genome sequence of thermotolerant Bacillus methanolicus: features and regulation related to methylotrophy and production of L-lysine and L-glutamate from methanol," Applied and Environmental Microbiology, 78(15):5170-5181 (2012).
Hemschemeier et al., "Biochemical and physiological characterization of the pyruvate formate-lyase Pfl 1 of Chlamydomonas reinhardtii, a typically bacterial enzyme in eukaryotic alga, " Eukaryot. Cell 7:518-526 (2008).
Hermann et al., "Energy Conservation via Electron-Transferring Flavoprotein in Anaerobic Bacteria," J. Bacteriol. 190(3):784-791 (2008).
Hesslinger et al., "Novel keto acid formate-lyase and propionate kinase enzymes are components of an anaerobic pathway in *Escherichia coli* that degrades L-threonine to propionate," Mol. Microbiol 27:477-492 (1998).
Hibbert et al. "Directed evolution of biocatalytic processes," Biomol. Eng. 22:11-19 (2005).
Hoffmeister et al., "Mitochondrial trans-2-enoyl-CoA reductase of wax ester fermentation from Euglena gracilis defines a new family of enzymes involved in lipid synthesis," J. Biol. Chem. 280:4329-4338 (2005).
Hohmann et al., "Characterisation of PDC2, a gene necessary for high level expression of pyruvate decarboxylase structural genes in *Saccharomyces cerevisiae*," Mol. Gen. Genet. 241:657-666 (1993).
Huisman and Lalonde, "Ch. 30: Enzyme Evolution for Chemical Process Applications," In R N. Patel (ed.), Biocatalysis in the pharmaceutical and biotechnology industries, CRC Press, Boca Raton, FL, p. 717-742 (2007).
Ishida et al., "Efficient production of L-Lactic acid by metabolically engineered *Saccharomyces cerevisiae* with a genome-integrated L-lactate dehydrogenase gene." *Appl. Envirom. Microbiol.* 71:1964-1970 (2005).
Ito et al., "Cloning and high-level expression of the glutathione-independent formaldehyde dehydrogenase gene from Pseudomonas putida," J Bacteriol 176: 2483-2491 (1994).
Iverson et al., "Structure of the *Escherichia coli* fumarate reductase respiratory complex," Science 284(5422):1961-1966 (1999).
Iwakura et al., "Studies on regulatory functions of malic enzymes. VI. Purification and molecular properties of NADP-linked malic enzyme from *Escherichia coli* W," J. Biochem. 85:1355-1365 (1979).
Jacobi et al., "The hyp operon gene products are required for the maturation of catalytically active hydrogenase isoenzymes in *Escherichia coli*," Arch. Microbiol. 158(6):444-451 (1992).
Jerome et al., "Development of a fed-batch process for the production of a dye-linked formaldehyde dehydrogenase in Hyphomicrobium zavarzinii ZV 580,"Appl Microbiol Biotechnol 77:779-88 (2007).
Johnson et al. Purification and properties of dihydroxyacetone kinase from Klebsiella pneumoniae. J. Bacteriol. 1984, 160(1):55-60.

Kai et al., "Phosphoenolpyruvate carboxylase: three-dimensional structure and molecular mechanisms," Arch. Biochem. Biophys. 414:170-179 (2003).
Karlen et al., "Absolute determination of the activity of two $C^{14}$ dating standards," Arkiv Geofysik 4:465-471 (1968).
Kato et al., "The physiological role of the ribulose monophosphate pathway in bacteria and archaea," BioSci Biotechnol Biochem. 70(1):10-21 (2006).
Kellum and Drake, "Effects of cultivation gas phase on hydrogenase of the acetogen Clostridium thermoaceticum," J. Bacteriol. 160(1):466-469 (1984).
Kerscher et al., "A single external enzyme confers alternative NADH:ubiquinone oxidoreductase activity in Yarrowia lipolytica," J. Cell Sci. 112:2347-54 (1999).
Killenberg-Jabs et al., "Active oligomeric states of pyruvate decarboxylase and their functional characterization," Eur. J. Biochem. 268:1698-1704 (2001).
Kim et al., "Effect of overexpression of Actinobacillus succinogenes phosphoenolpyruvate carboxykinase on succinate production in *Escherichia coli*," Appl. Environ. Microbiol. 70:1238-1241 (2004).
Kim et al., "Construction of an *Escherichia coli* K-12 Mutant for Homoethanologenic Fermentation of glucose or Xylose without Foreign Genes, " Appl. Environ. Microbiol. 73:1766-1771 (2007).
Kim et al., "Dihydrolipoamide Dehydrogenase Mutation Alters the NADH Sensitivity of Pyruvate Dehydrogenase Complex of *Escherichi coli* K-12," J. Bacteriol. 190:3851-3858 (2008).
Kloosterman et al., "Molecular, biochemical, and functional characterization of a Nudix hydrolase protein that stimulates the activity of a nicotinoprotein alcohol dehydrogenase," J Biol Chem 277:34785-92 (2002).
Knappe et al., "Post-translational activation introduces a free radical into pyruvate formate-lyase," Proc. Natl. Acad. Sci. U.S.A. 81:1332-1335 (1984).
Kobayashi et al., "Physiochemical, Catalytic, and Immunochemical Properties of Fumarases Crystallized Separately from Mitochondrial and Cytosolic Fractions of Rat Liver," J. Biochem. 89:1923-1931 (1981).
Koland and Gennis, "Proximity of Reactive Cysteine Residue and Flavin in *Escherichia coli* Pyruvate Oxidase as Estimated by Flourescence Energy Transfer," Biochemistry 21:4438-4442 (1982).
Kretz et al., "Gene site saturation mutagenesis: a comprehensive mutagenesis approach," Methods Enzymol. 388:3-11 (2004).
Krieger et al., "Pyruvate decarboxylase from Kluyveromyces lactis an enzyme with an extraordinary substrate activation behaviour," Eur. J. Biochem. 269:3256-3263 (2002).
Kwon et al., "Influence of gluconeogenic phosphoenolpyruvate carboxykinase (PCK) expression on succinic acid fermentation in *Escherichia coli* under high bicarbonate condition," J. Microbiol. Biotechnol. 16(9):1448-1452 (2006).
Laivenieks et al., "Cloning sequencing, and overexpression of the Anaerobiospirillum succinicproducens phosphoenolpyruvate carboxykinase (pckA) gene," Appl. Environ. Microbiol. 63:2273-2280 (1997).
Lee et al., "Cloning and Characterization of Mannheimia succiniciproducens MBEL55E Phosphoenolpyruvate Carboxykinase (pckA) Gene," Biotechnol. Bioprocess Eng. 7:95-99 (2002).
Lee et al., "A new approach to directed gene evolution by recombined extension on truncated templates (RETT)," J. Molec. Catalysis 26:119-129 (2003).
Lehtio and Goldman, "The pyruvate format lyase family: sequences, structures and activation," Protein Eng. Des.Sel. 17:545-552 (2004).
Leppänen et al., "Pyruvate formate lyase is structurally homologous to type I ribonucleotide reductase," Structure 7:733-744 (1999).
Li and Jordan, "Effecrts of Substitution of Tryptophan 412 in the Substrate Activation Pathway of Yeast Pyruvate Decarboxylase," Biochemistry 38:10004-10012 (1999).
Li et al., "Properties of Nicotinamide Adenine Dinucleotide Phosphate-Dependent Formate Dehydrogenase from Clostridium thermoaceticum," J. Bacteriol. 92(2):405-412 (1966).

(56) References Cited

OTHER PUBLICATIONS

Lin et al., "Fed-batch culture of a metabolically engineered *Escherichia coli* strain designed for high-level succinate production and yield under aerobic conditions," Biotechnol. Bioeng. 90(6):775-779 (2005).
Lovell et al., "Cloning and expression in *Escherichia coli* of the Clostridium thermoaceticum gene encoding thermostable formyltetrahydrofolate synthetase," Arch. Microbiol. 149(4):280-285 (1988).
Lovell, et al., "Primary structure of the thermostable formyltetrahydrofolate synthetase from Clostridium thermoaceticum," Biochemistry 20(29):5687-5694 (1990).
Low et al., "Mimicking somatic hypermutation: affinity maturation of antibodies displayed on baceriophage using a bacterial mutator strain," J. Mol. Biol. 260(3):359-368 (1996).
Lutz et al., "Rapid generation of incremental truncation libraries for protein engineering using α-phosphothioate nucleotides," Nucleic Acids Res. 15:29(4):e16 (2001).
Lutz et al., "Creating multiple-crossover DNA libraries independent of sequence identity," Proc. Natl. Acad. Sci. U.S.A. 98(20):11248-11253 (2001).
Maeda et al., "Enhanced hydrogen production from glucose by metabolically engineered *Escherichia coli*," Appl. Microbiol. Biotechnol. 77:879-890 (2007).
Maeder et al., "The Methanosarcina barkeri genome: comparative analysis with Methanosarcina acetivorans and Methanosarcina mazei reveals extensive rearrangement within methanosarcinal genomes," J. Bacteriol. 188(22):7922-7931 (2006).
Maklashina et al., "Anaerobic expression of *Escherichia coli* succinate dehydrogenase: functional replacement of fumarate reductase in the respiratory chain during anaerobic growth," *J. Bacteriol.* 180(22):5989-5996 (1998).
Maklashina et al., "Fumarate reductase and succinate oxidase activity of *Escherichia coli* complex II homologs are perturbed differently by mutation of the flavin binding domain," J Biol Chem 281:11357-65 (2006).
Makuc et al., "The putative monocarboxylate permeases of the yeast *Saccharomyces cerevisiae* do not transport monocarboxylic acids across the plasma membrane," Yeast 18:1131-43 (2001.
Mann, "An International Reference Materian for Radiocarbon Dating," Radiocarbon, 25(2):519-527 (1983).
Mattevi et al., "Atomic structure of the cubic core of the pyruvate dehydrogenase multienzyme complex," Science 255:1544-1550 (1992).
McAlister-Henn and Thompson, "Isolation and expression of the gene encoding yeast mitochondrial malate dehydrogenase," J. Bacteriol. 169:5157-5166 (1987).
Melchiorsen et al., "The level of pyruvate-formate lyase controls the shift from homolactic to mixed-acid product formation in Lactoccus lactis," Appl. Microbiol. Biotechnol. 58(3):338-344 (2002).
Menzel et al., "Enzymatic evidence for an involvement of pyruvate dehydrogenase in the anaerobic glycerol metabolism of Klebsiella pneumoniae," J. Biotechnol. 56:135-142 (1997).
Minard and McAlister-Henn, "Isolation, nucleotide sequence analysis, and disruption of the MDH2 gene from *Saccharomyces cerevisiae*: evidence for three isozymes of yeast malate dehydrogenase," Mol. Cell. Biol. 11:370-380 (1991).
Mitsui et al., "Formaldehyde fixation contributes to detoxification for growth of a nonmethylotroph, Burkholderia cepacia TM1, on vanillic acid," AEM 69(10):6128-6132 (2003).
Mizobata et al., "Purification and Characterization of a thermostable Class II Fumarase from Thermus thermophilus," Arch. Biochem. Biophys. 355:49-55 (1998).
Molin et al., "Dihydroxyacetone kinases in *Saccharomyces cerevisiae* are involved in detoxification of dihydroxyacetone," J Biol Chem. 17; 278(3):1415-1423(2003).
Mukhopadhyay and Purwantini, "Pyruvate carboxylase from Mycobacterium smegmatis: stabilization, rapid purification, moleculare and biochemical characterization and regulation of the cellular level," Biochim. Biophys. Acta 1475(3):191-206 (2000).

Muller et al., "Nucleotide exchange and excision technology (NExT) DNA shuffling: a robust method for DNA fragmentation and directed evolution," Nucleic Acids Res. 33(13):e117 (2005).
Muratsubaki and Enomoto, "One of the fumarate reductase isoenzymes from *Saccharomyces* cerevisiae is encoded by the OSM1 gene," Arch. Biochem. Biophys. 352(2):175-181 (1998).
Myronova et al., "Three-dimensional structure determination of a protein supercomplex that oxidizes methane to formaldehyde in Methylococcus capsulatus (Bath)," Biochem 45:11905-14 (2006).
Nagy et al., "Formyltetrahydrofolate hydrolase, a regulatory enzyme that functions to balance pools of tetrahydrofolate and one-carbon tetrahydrofolate adducts in *Escherichia coli*," J. Bacteriol. 3:1292-1298 (1995).
Naidu and Ragsdale, "Characterization of a three-component vanillate O-demethylase from Moorella thermoacetica," J. Bacteriol. 183(11):3276-3281 (2001).
Nakano et al., "Characterization of Anaerobic Fermentative Growth of Bacillus subtilis: Identification of Fermentation End Products and Genes Required for Growth," J. Bacteriol. 179(21):6749-6755 (1997).
Ness et al., "Synthetic shuffling expands functional protein diversity by allowing amino acids to recombine independently," Nat. Biotechnol. 20(12):1251-1255 (2002).
Nunn et al., "The nucleotide sequence and deduced amino acid sequence of the genes for cytochrome cL and a hypothetical second subunit of the methanol dehydrogenase of Methylobacterium AM1," Nucl Acid Res 16:7722 (1988).
O'Brien and Gennis, "Studies of the Thiamin Pyrophosphate Binding Site of *Escherichia coli* Pyruvate Oxidase," J. Biol. Chem. 255(8):3302-3307 (1980).
O'Brien et al., "Regulation by Lipids of Cofactor Binding to a Peripheral Membrane Enzyme: Binding of Thiamin Pyrophosphate to Pyruvate Oxidase," Biochemistry 16(14):3105-3109 (1977).
O'Brien et al., "Chemical, physical and enzymatic comparisons of formyltetrahydrofolate synthetases from thermo- and mesophilic clostridia," Experientia. Suppl. 26:249-262 (1976).
Orita et al., "Bifunctional enzyme fusion of 3-hexulose-6-phosphate synthase and 6-phospho-3-hexuloisomerase," Appl Microbiol Biotechnol. 76:439-445 (2007).
Ostermeier et al., "A combinatorial approach to hybrid enzymes independent of DNA homology," Nat. Biotechnol. 17(12):1205-1209 (1999).
Ostermeier et al., "Combinatorial protein engineering by incremental truncation," Proc. Natl. Acad. Sci. U.S.A. 96(7):3562-3567 (1999).
Otten and Quax. Directed evolution: selecting today's biocatalysts. Biomol. Eng. 22:1-9 (2005).
Parkin et al., "Rapid and efficient electrocatalytic CO2/CO interconversions by Carboxydothermus hydrogenoformans CO dehydrogenase I on an electrode," J. Am. Chem. Soc. 129(34):10328-10329 (2007).
Park et al., "Growth of mycobacteria on carbon monoxide and methanol," 2003, JBac 185(1):142-7.
Passoth et al., "Molecular cloning of alcohol dehydrogenase genes of the yeast Pichia stipitis and identification of the fermentative ADH," Yeast 14:1311-23 (1998).
Paxton et al., "Role of branched-chain 2-oxo acid dehydrogenase and pyruvate dehydrogenase in 2-oxobutyrate metabolism," Biochem. J. 234:295-303 (1986).
Pierce et al., "The Complete Genome Sequence of Moorella thermoacetia (f. Clostridum thermoaceticum)," Environ. Microbiol. 10(10):2550-2573 (2008).
Poehlein et al., "An ancient pathway combining carbon dioxide fixation with the generation and utilization of a sodium ion gradient for ATP synthesis," PLoS One. 7:e33439 (2012).
Popp et al., "Fermentative production of L-glycerol 3-phosphate utilizing a *Saccharomyces cerevisiae* strain with an engineered glycerol biosynthetic pathway," Biotechnol Bioeng 100:497-505 (2008).
Portnoy et al., "Aerobic Fermentation of D-Glucose by an Evolved Cytochrome Oxidase-Deficient *Escherichia coli* Strain," AEM 74:7561-9 (2008).

(56) References Cited

OTHER PUBLICATIONS

Pritchard et al., "A general model of error-prone PCR," J. Theor. Biol. 234:497-509 (2005).
Pritchett and Metcalf, "Genetic, physiological and biochemical characterization of multiple methanol methyltransferase isozymes in Methanosarcina acetivorans C2A," Mol. Microbiol. 56(5):1183-1194 (2005).
Ragsdale, "Life with carbon monoxide," Crit. Rev. Biochem. Mol. Biol. 39(3):165-195 (2004).
Rajpal et al., "A general method for greatly improving the affinity of antibodies by using combinatorial libraries," Proc. Natl. Acad. Sci. U.S.A. 102(24):8466-8471 (2005).
Rangarajan et al., "Structure of [NiFe] hydrogenase maturation protein HypE from *Escherichia coli* and its interaction with HypF," J. Bacteriol. 190(4):1447-1458 (2008).
Reda et al., "Reversible interconversion of carbon dioxide and formate by an electroactive enzyme," Proc. Natl. Acad. Sci. U.S.A. 105:10654-10658 (2008).
Reetz et al., "Directed Evolution of an Enantioselective Enzyme through Combinatorial Multiple-Cassette Mutagenesis," Agnew. Chem. Int. Ed. Engl. 40:3589-3591 (2001).
Reetz et al., "Iterative Saturation Mutagenesis on the Basis of B Factors as a Strategy for Increasing Protein Thermostability," Agnew. Chem. Int. Ed. Engl. 45:7745-7751 (2006).
Reetz and Carballeria, "Iterative saturation mutagenesis (ISM) for rapid directed evolution of functional enzymes," Nat. Protoc. 2(4):891-903 (2007).
Reidhaar-Olson et al., "Random mutagenesis of protein sequences using oligonucleotide cassettes," Methods Enzymol. 208:564-586 (1991).
Reidhaar-Olson and Sauer, "Combinatorial cassette mutagenesis as a probe of the informational content of protein sequences," Science 241(4861):53-57 (1988).
Ro et al., "Dihydroxyacetone synthase from a methanol-utilizing carboxydobacterium, *Acinetobacter* sp. strain JC1 DSM 3803," 1997, JBac 179(19):6041-6047.
Sanchez et al., "Efficient succinic acid production from glucose through overexpression of pyruvate carboxylase in an *Escherichia coli* alcohol dehydrogenase and lactate dehydrogenase mutant," Biotechnol. Prog. 21(2):358-365 (2005).
Sass et al., "Folding of Fumarase during Mitochondrial Import Determines its Dual Targeting in Yeast," J. Biol. Chem. 278:45109-45116 (2003).
Sauer et al., "Methanol:Coenzyme M methyltransferase from Methanosarcina barkeri. Purification, properties and encoding genes of the corrinoid protein MT1," Eur. J. Biochem. 243(3):670-677 (1997).
Sawers and Boxer, "Purification and properties of membrane-bound hydrogenase isoenzyme 1 from anaerobically grown *Escherichia coli* K12," Eur. J. Biochem. 156(2):265-275 (1986).
Sawers et al., "Differential expression of hydrogenase isoenzymes in *Escherichia coli* K-12: evidence for a third isoenzyme," J. Bacteriol. 164(3):1324-1331 (1985).
Sawers et al., "Characterization and physiological roles of membrane-bound hydrogenase isoenzymes from *Salmonella typhimurium*," J. Bacteriol. 168(1):398-404 (1986).
Sawers, "The hydrogenases and formate dehydrogenases of *Escherichia coli*," Antonie Van Leeuwenhoek 66(1-3):57-88 (1994).
Schink and Schlegel, "The membrane-bound hydrogenase of Alcaligenes eutrophus. I. Solubilization, purification, and biochemical properties," Biochim. Biophys. Acta, 567, 315-324 (1979).
Schneider and Schlegel, "Purification and Properties of Soluble Hydrogenase from Alcaligenes Eutrphus H16," Biochim. Biophys. Acta 452, 66-80 (1976).
Schreiner et al., "Pyruvate: quinone oxidoreductase in Corynebacterium glutamicum: molecular analysis of the pqo gene, significance of the enzyme, and phylogenetic aspects," J Bacteriol 188:1341-50 (2006).

Seedorf et al., "The genome of Clostridium kluyveri, a strict anaerobe with unique metabolic features," Proc. Natl. Acad. Sci. U.S.A. 105(6):2128-2133 (2008).
Selifonova et al., "Rapid evolution of novel traits in microorganisms," Appl. Environ. Microbiol. 67(8):3645-3649 (2001).
Sen et al., "Developments in directed evolution for improving enzyme functions," Appl. Biochem. Biotechnol. 143(3):212-223 (2007).
Shao et al., "Random-priming in vitro recombination: an effective tool for directed evolution," Nucleic Acids Res. 26(2):681-683 (1998).
Sheppard et al., "Purification and properties of NADH-dependent 5, 10-methylenetetrahydrofolate reductase (MetF) from *Escherichia coli*," J. Bacteriol. 181:718-725 (1999).
Shimoyama et al., "MmcBC in Pelotomaculum thermopropionicum represents a novel group of prokaryotic fumarases," FEMS Microbiol Lett. 270(2):207-213 (2007).
Sieber et al., "Libraries of hybrid proteins from distantly related sequences," Nat. Biotechnol. 19(5):456-460 (2001).
Siebold et al., "A mechanism of covalent substrate binding in the x-ray structure of subunit K of the *Escherichia coli* dihydroxyacetone kinase," 2003, PNAS. 100(14):8188-8192.
Siegert et al., "Exchanging the substrate specificities of pyruvate decarboxylase from Zymomonas mobilis and benzoylase from Pseudomonas putida," Protein Eng. Des. Sel. 18:345-357 (2005).
Simanshu et al., "Structure and function of enzymes involved in the anaerobic degradation of L-threonine to propionate," J. Biosci. 32(6):1195-1206 (2007).
Skarstedt and Silverstein, "Escherichia coli Acetate Kinase Mechanism Studied by Net Initial Rate, Equilibriu, and Independent Isotopic Exchange Kinetics," J. Biol. Chem. 251:6775-6783 (1976).
Smith et al., "Fumarate metabolism and the microaerophily of *Campylobacter* species," Int. J. Biochem. Cell Biol. 31:961-975 (1999).
Soini et al., "High cell density media for *Escherichia coli* are generally designed for aerobic cultivations—consequences for large-scale bioprocesses and shake flask cultures," Microb. Cell. Fact. 7:26 (2008).
St. Maurice et al., "Flavodoxin:quinone reductase (FqrB): a redox partner of pyruvate:ferredoxin oxidoreductase that reversibly couples pyruvate oxidation to NADPH production in Helicobacter pylori and Campylobacter jejuni," J. Bacteriol. 189:4764-4773 (2007).
Steffan and McAlister-Henn, "Isolation and characterization of the yeast gene encoding the MDH3 isozyme of malate dehydrogenase," J. Biol. Chem. 267:24708-24715 (1992).
Steinbüchel and Schlegel, "NAD-linked L(+)-lactate dehydrogenase from the strict aerobe alcaligenes eutrophus. 2. Kinetic properties and inhibition by oxaloacetate," Eur. J. Biochem. 130(2):329-334 (1983).
Stemmer, "Rapid evolution of a protein in vitro by DNA shuffling," Nature 370:389-391 (1994).
Stemmer, "DNA Shuffling by random fragmentation and reassembly: in vitro recombination for molecular evolution," Proc. Natl. Acad. Sci. U.S.A. 91(22):10747-10751 (1994).
Stols and Donnelly, "Production of succinic acid through overexpression of NAD+-dependent malic enzyme in an *Escherichia coli* mutant," Appl. Environ. Microbiol. 63(7):2695-2701 (1997).
Stols et al., "Expression of Ascaris suum malic enzyme in a mutant *Escherichia coli* allows production of succinic acid from glucose," Appl. Biochem. Biotechnol. 63-65: 153-158 (1997).
Sunga et al., "The Pichia pastoris formaldehyde dehydrogenase gene (FLD1) as a marker for selection of multicopy expression strains of P. pastoris," Gene 330:39-47 (2004).
Suzuki, et al., "*Corynebacterium* sp. U-96 contains a cluster of genes of enzymes for the catabolism of sarcosine to pyruvate," Biosci. Biotechnol. Biochem. 69(5):952-956 (2005).
Suzuki, "Phosphotransacetylase of *Escherichia coli* B, activation by pyruvate and inhibition by NADH and certain nucleotides," Biochim. Biophys. Acta 191(3):559-569 (1969).
Takacs et al., "Formate hydrogenlyase in the hyperthermophilic archaeon, Thermococcus litoralis," BMC Microbiol. 8:88 (2008).

(56) References Cited

OTHER PUBLICATIONS

Takahashi et al., "Metabolic Pathways for Cytoxic End Product Formation from Glutamate-and Aspartate-Containing Peptides by Porphyromonas gingivalis," J. Bacteriol. 182(17):4704-4710 (2000).
Takeo, "Existence and properties of two malic enzymes in Escherichia coli especially of NAD-linked enzyme," J. Biochem. 66:379-387 (1969).
Tallant and Krzycki, "Coenzyme M methylase activity of the 480-kilodalton corrinoid protein from Methanosarcina barkeri," J. Bacteriol. 178(5):1295-1301 (1996).
Tallant and Krzycki, "Methylthiol:Coenzyme M Methyltransferase from Methanosarcina barkeri, an enzyme of methanogenesis from dimethylsulfide and methylmercaptopropionate," J. Bacteriol. 179(22):6902-6911 (1997).
Tallant et al., "The MtsA subunit of the methylthiol:Coenzyme M methyltransferase of Methanosarcina barkeri catalyses both half-reactions of corrinoid-dependent dimethylsulfide: Coenzyme M methyl transfer," J. Biol. Chem. 276(6):4485-4493 (2001).
Ter Schure et al., "Pyruvate Decarboxylase Catalyzes Decarboxylation of Branched-Chaing 2-Oxo Acids but Is Not Essential for Fusel Alcohol Production by Saccharomyces cerevisiae," Appl. Environ. Microbiol. 64(4):1303-1307 (1998).
Todisco et al., "Identification of the mitochondrial NAD+ transporter in Saccharomyces cerevisiae," J Biol Chem 281:1524-31 (2006).
Tseng et al., "Oxygen- and growth rate-dependent regulation of Escherichia coli fumarase (FumA, FumB, and BumC) activity," J. Bacteriol. 183(2):461-467 (2001).
Valdes-Hevia and Gancedo, "Isolation and characterization of the gene encoding phosphoenolpyruvate carboxykinase from Saccharomyces cerevisiae," FEBS Lett. 258(2):313-316 (1989).
van Maris et al., "Overproduction of threonine aldolase circumvents the biosynthetic role of pyruvate decarboxylase in glucose-limited chemostat cultures of Saccharomyces cerevisiae," AEM 69:2094-9 (2003).
Vardar-Schara et al., "Metabolically engineered bacteria for producing hydrogen via fermentation," Microbio. Biotechnol. 1:107-125 (2008).
Volkov et al., "Recombination and chimeragenesis by in vitro heteroduplex formation and in vivo repair," Nucleic Acids Res. 27(18):e18 (1999).
Volkov et al., "Random chimeragenesis by heteroduplex recombination," Methods Enzymol. 328:456-463 (2000).
Vorholt, et al., "Novel formaldehyde-activating enzyme in Methylobacterium extorquens AM1 required for growth on methanol," J. Bacteriol.,182(23), 6645-6650 (2000).
Walker et al., "Yeast pyruvate carboxylase: identification of two genes encoding isoenzymes," Biochem. Biophys. Res. Commun. 176:1210-1217 (2007).
Wang et al., "NADP Reduction with Reduced Ferredoxin and NADP Reduction with NADH Are Coupled via an Electron-Bifurcating Enzyme Complex in Clostridium kluyveri," J Bacteriol 192: 5115-5123 (2010).
Weidner and Sawers, "Molecular Characterization of the Genes Encoding Pyruvate Formate-Lyase and Its Activating Enzyme of Clostridium pasteruianum," J. Bacteriol. 178(8):2440-2444 (1996).
Whitehead and Rabinowitz, "Cloning and expression in Escherichia coli of the gene for 10-formyltetrahydrofolate synthetase from Clostridium acidiurici ("Clostridium acidi-urici")," J. Bacteriol. 167:205-209 (1986).
Whitehead and Rabinowitz, "Nucleotide Sequence of the Clostridium acidiurici ("Clostridium acidi-urici") Gene for 10-Formyltetrahydrofolate Synthetase Shows Extensive Amino Acid Homology with the Trifunctional Enzyme C1-Tetrahydrofolate Synthase from Saccharomyces cerevisiae," J. Bacteriol. 170(7):3255-3261 (1988).
Wong et al., "Sequence satruation mutagenesis with tunable mutation frequencies," Anal. Biochem. 341:187-189 (2005).
Wong et al., "Molecular Properties of Pyruvate Formate-Lyase Activating Enzyme," Biochemistry 32:14102-14110 (1993).
Wong et al., "Transversion-enriched sequence saturation mutagenesis (SeSaM-Tv+): a random mutagenesis method with consecutive nucleotide exchanges that complements the bias of error-prone PCR," Biotechnol. J. 3:74-82 (2008).
Wong et al., "Sequence saturation mutagenesis (SeSaM): a novel method for directed evolution," Nucleic Acids Res. 32(3):e26 (2004).
Woods et al., "Two biochemically distinct classes of fumarase in Escherichia coli," Biochim. Biophys. Acta 954(1):14-26 (1988).
Wu et al., "Life in hot carbon monoxide: the complete genome sequence of Carboxydothermus hydrogenoformans Z-2901," PLoS Genet. 1:e65 (2005).
Yamamoto et al., "Carboxylation reaction catalyzed by 2-oxoglutarate:ferredoxin oxidoreductases from Hydrogenobacter thermophilus," Extremophiles 14:79-85 (2010).
Yamamoto et al., "Purification and properties of NADP-dependent formate dehydrogenase from Clostridium thermoaceticum, a tungsten-selenium-iron protein," J. Biol. Chem. 258(3):1826-1832 (1983).
Yasueda et al., "Bacillus subtilis yckG and yckF encode two key enzymes of the ribulose monophosphate pathway used by methylotrophs, and yckH is required for their expression," 1999. J Bac 181(23):7154-7160.
Yim et al., "Metabolic engineering of Escherichia coli for direct production of 1,4-butanediol," Nature Chemical Biology, 7:445-452 (2011).
Zhang et al., "Metabolic evolution of energy-conserving pathways for succinate production in Escherichia coli," Proc. Natl. Acad. Sci. USA 106(48):20180-20185 (2009).
Zhao et al., "Molecular evolution by staggered extension process (StEP) in vitro recombination," Nat. Biotechnol. 16(3):258-261 (1998).
Zhou et al., "The remarkable structural and functional organization of the eukaryotic pyruvate dehydrogenase complexes," Proc. Natl. Acad. Sci. U.S.A. 98:14802-14807 (2001).
Zhou et al., "Isolation, crystallization and preliminary X-ray analysis of a methanol-induced corrinoid protein from Moorella thermoacetica," Acta Crystallogr. Sect. F. Struct. Biol. Cyrst. Commun. 61:537-540 (2005).
Zhou et al., "Engineering a native homoethanol pathway in Escherichia coli B for ethanol production," Biotechnol. Lett. 30:335-342 (2008).
Zhu and Lin, "A mutant crp allele that differentially activates the operons of the fuc regulon in Escherichia coli," J. Bacteriol. 170:2352-2358 (1988).
Vorholt et al., "Cofactor-dependent pathways of formaldehyde oxidation in methylotrophic bacteria", Arch Microbiol., 178(4):239-249 (2002).
Ao et al., "Towards kinetic modeling of global metabolic networks: Methylobacterium extorquens AM1 growth as validation", Sheng Wu Gong Cheng Xue Bao., 24(6):980-994 (2008).
Ragsdale et al., "Acetogenesis and the Wood-Ljungdahl pathway of CO(2) fixation", Biochim Biophys Acta., 1784(12):1873-1898 (2008).

* cited by examiner

MICROORGANISMS AND METHODS FOR ENHANCING THE AVAILABILITY OF REDUCING EQUIVALENTS IN THE PRESENCE OF METHANOL, AND FOR PRODUCING SUCCINATE RELATED THERETO

CROSS-REFERENCE TO RELATED APPLICATIONS

This application claims the benefit of U.S. Ser. No. 61/766,642 filed Feb. 19, 2013, and U.S. Ser. No. 61/717,001 filed Oct. 22, 2012, each of which is incorporated herein by reference in its entirety.

1. SUMMARY

Provided herein are methods generally relating to metabolic and biosynthetic processes and microbial organisms capable of producing organic compounds. Specifically, provided herein is a non-naturally occurring microbial organism having a methanol metabolic pathway that can enhance the availability of reducing equivalents in the presence of methanol. Such reducing equivalents can be used to increase the product yield of organic compounds produced by the microbial organism, such as succinate. Also provided herein are non-naturally occurring microbial organisms and methods thereof to produce optimal yields of succinate.

In a first aspect, provided herein is a non-naturally occurring microbial organism having a methanol metabolic pathway, wherein said organism comprises at least one nucleic acid encoding a methanol metabolic pathway enzyme expressed in a sufficient amount to enhance the availability of reducing equivalents in the presence of methanol. In certain embodiments, the methanol metabolic pathway comprises one or more enzymes selected from the group consisting of a methanol methyltransferase; a methylenetetrahydrofolate reductase; a methylenetetrahydrofolate dehydrogenase; a methenyltetrahydrofolate cyclohydrolase; a formyltetrahydrofolate deformylase; a formyltetrahydrofolate synthetase; a formate hydrogen lyase; a hydrogenase; a formate dehydrogenase; a methanol dehydrogenase; a formaldehyde activating enzyme; a formaldehyde dehydrogenase; a S-(hydroxymethyl)glutathione synthase; a glutathione-dependent formaldehyde dehydrogenase; and an S-formylglutathione hydrolase. Such organisms advantageously allow for the production of reducing equivalents, which can then be used by the organism for the production of succinate using any one of the succinate pathways provided herein.

In a second aspect, provided herein is a non-naturally occurring microbial organism having (1) a methanol metabolic pathway, wherein said organism comprises at least one exogenous nucleic acid encoding a methanol metabolic pathway enzyme expressed in a sufficient amount to enhance the availability of reducing equivalents in the presence of methanol; and (2) a succinate pathway. In some embodiments, the organism further comprises at least one nucleic acid encoding a succinate pathway enzyme expressed in a sufficient amount to produce succinate. In some embodiments, the nucleic acid is an exogenous nucleic acid. In other embodiments, the nucleic acid is an endogenous nucleic acid. In certain embodiments, the succinate pathway enzyme is selected from the group consisting of a phosphoenolpyruvate (PEP) carboxylase or a PEP carboxykinase; a pyruvate carboxylase; a malate dehydrogenase; a malic enzyme; a fumarase; and a fumarate reductase.

In other embodiments, the organism having a methanol metabolic pathway, either alone or in combination with a succinate pathway, as provided herein, further comprises a formaldehyde assimilation pathway that utilizes formaldehyde, e.g., obtained from the oxidation of methanol, in the formation of intermediates of certain central metabolic pathways that can be used, for example, in the formation of biomass. In some of embodiments, the formaldehyde assimilation pathway comprises a hexylose-6-phosphate synthase, 6-phospho-3-hexyloisomerase, dihydroxyacetone synthase or dihydroxyacetone kinase. In certain embodiments, provided herein is a non-naturally occurring microbial organism having a methanol metabolic pathway, wherein said organism comprises at least one exogenous nucleic acid encoding a methanol dehydrogenase expressed in a sufficient amount to enhance the availability of reducing equivalents in the presence of methanol and/or expressed in a sufficient amount to convert methanol to formaldehyde. In some embodiments, the microbial organism further comprises a formaldehyde assimilation pathway. In certain embodiments, the organism further comprises at least one exogenous nucleic acid encoding a formaldehyde assimilation pathway enzyme expressed in a sufficient amount to produce an intermediate of glycolysis. In certain embodiments, the formaldehyde assimilation pathway enzyme is selected from the group consisting of a hexylose-6-phosphate synthase, 6-phospho-3-hexyloisomerase, dihydroxyacetone synthase and dihydroxyacetone kinase.

In some embodiments, the organism further comprises one or more gene disruptions, occurring in one or more endogenous genes encoding protein(s) or enzyme(s) involved in native production of ethanol, glycerol, acetate, lactate, formate, $CO_2$, and/or amino acids by said microbial organism, wherein said one or more gene disruptions confer increased production of succinate in said microbial organism. In some embodiments, one or more endogenous enzymes involved in native production of ethanol, glycerol, acetate, lactate, formate, $CO_2$ and/or amino acids by the microbial organism, has attenuated enzyme activity or expression levels. In certain embodiments, the organism comprises from one to twenty-five gene disruptions. In other embodiments, the organism comprises from one to twenty gene disruptions. In some embodiments, the organism comprises from one to fifteen gene disruptions. In other embodiments, the organism comprises from one to ten gene disruptions. In some embodiments, the organism comprises from one to five gene disruptions. In certain embodiments, the organism comprises 1, 2, 3, 4, 5, 6, 7, 8, 9, 10, 11, 12, 13, 14, 15, 16, 17, 18, 19, 20, 21, 22, 23, 24 or 25 gene disruptions or more.

In other aspects, provided herein are methods for producing succinate, comprising culturing any one of the non-naturally occurring microbial organisms comprising a methanol metabolic pathway and a succinate pathway provided herein under conditions and for a sufficient period of time to produce succinate. In certain embodiments, the organism is cultured in a substantially anaerobic culture medium.

2. BRIEF DESCRIPTION OF THE DRAWINGS

FIG. 1 shows exemplary metabolic pathways enabling the extraction of reducing equivalents from methanol. The enzymatic transformations shown are carried out by the following enzymes: 1A) a methanol methyltransferase, 1B) a methylenetetrahydrofolate reductase, 1C) a methylenetetrahydrofolate dehydrogenase, 1D) a methenyltetrahydrofolate cyclohydrolase, 1E) a formyltetrahydrofolate deformylase, 1F) a formyltetrahydrofolate synthetase, 1G) a formate hydrogen lyase, 1H) a hydrogenase, 1I) a formate dehydrogenase, 1J) a methanol dehydrogenase, 1K) a formaldehyde activating enzyme, 1L) a formaldehyde dehydrogenase, 1M) a S-(hydroxymethyl)glutathione synthase, 1N) a glutathione-dependent formaldehyde dehydrogenase, and 1O) a S-formylglutathione hydrolase. In certain embodiments, steps K and/or M are spontaneous.

FIG. 2 shows exemplary succinate pathways, which can be used to increase succinate yields from carbohydrates when reducing equivalents produced by a methanol metabolic pathway provided herein are available. For example, pathways for the production of succinate from glucose, $CO_2$, and reducing equivalents (e.g., MeOH) at a theoretical yield of 2.0 mol succinate/mol glucose are provided. The enzymatic transformations shown are carried out by the following enzymes: 2A) a phosphoenolpyruvate (PEP) carboxylase or a PEP carboxykinase; 2B) a pyruvate carboxylase; 2C) a malate dehydrogenase; 2D) a malic enzyme; 2E) a fumarase; and 2F) a fumarate reductase. Succinate production can be carried out by 2A, 2C, 2E and 2F; 2B, 2C, 2E and 2F; or 2D, 2E and 2F.

3. DETAILED DESCRIPTION OF THE INVENTION

3.1 Definitions

Figure 1:
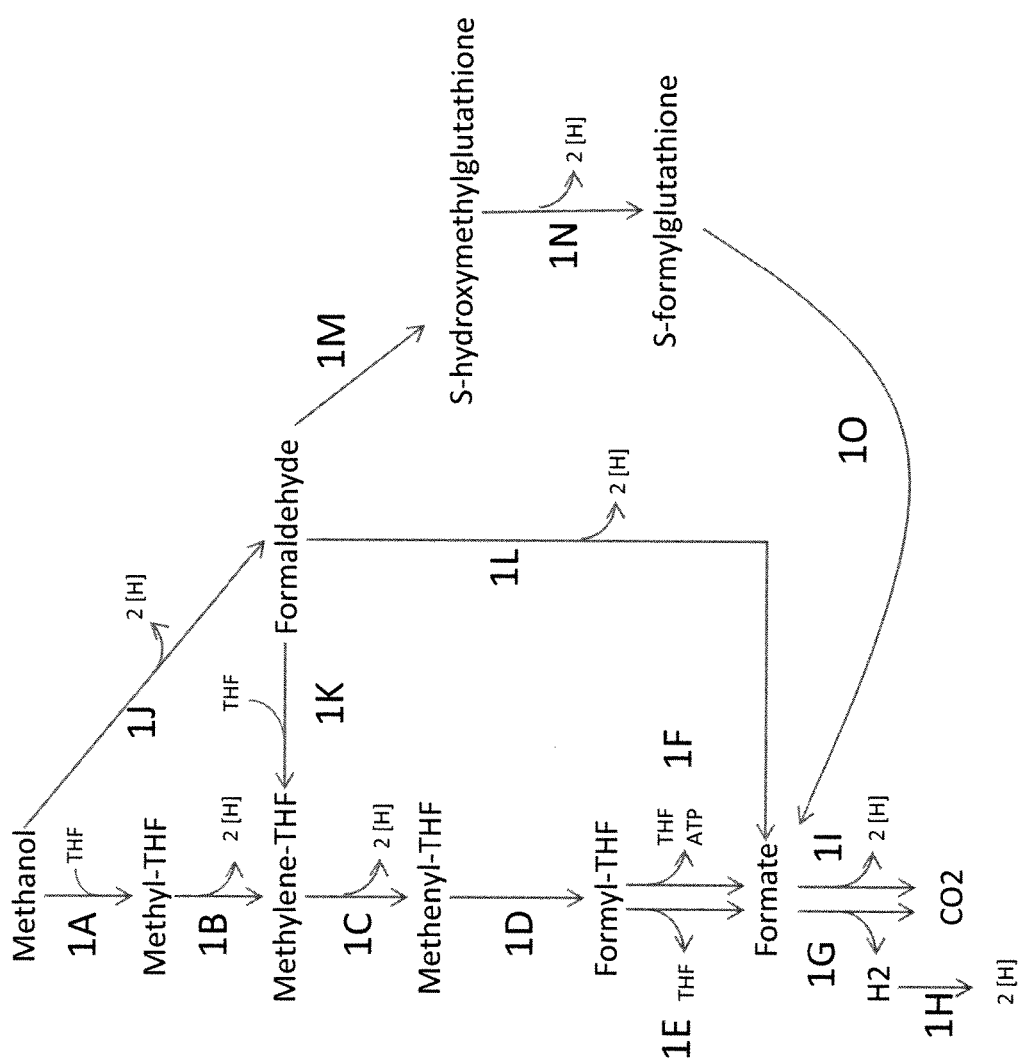

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a succinate biosynthetic pathway.

As used herein, "succinate" is the ionized form of succinic acid (IUPAC name butanedioic acid), and it is understood that succinate and succinic acid can be used interchangeably throughout to refer to the compound in any of its neutral or ionized forms, including any salt forms thereof. It is understood by those skilled understand that the specific form will depend on the pH. The chemical structure of succinic acid is shown below:

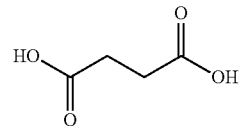

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

As used herein, the term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions in the non-naturally occurring microorganisms of the invention.

The phenotypic effect of a gene disruption can be a null mutation, which can arise from many types of mutations including inactivating point mutations, entire gene deletions, and deletions of chromosomal segments or entire chromosomes. Specific antisense nucleic acid compounds and enzyme inhibitors, such as antibiotics, can also produce null mutant phenotype, therefore being equivalent to gene disruption.

As used herein, the term "growth-coupled" when used in reference to the production of a biochemical product is intended to mean that the biosynthesis of the referenced biochemical product is produced during the growth phase of a microorganism. In a particular embodiment, the growth-coupled production can be obligatory, meaning that the biosynthesis of the referenced biochemical is an obligatory product produced during the growth phase of a microorganism. The term "growth-coupled" when used in reference to the consumption of a biochemical is intended to mean that the referenced biochemical is consumed during the growth phase of a microorganism.

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given pathway to function. However, the attenuation of the activity or amount of an enzyme or protein that mimics complete disruption for one pathway, can still be sufficient for a separate pathway to continue to function. For example, attenuation of an endogenous enzyme or protein can be sufficient to mimic the complete disruption of the same enzyme or protein for production of a fatty alcohol, fatty aldehyde or fatty acid product of the invention, but the remaining activity or amount of enzyme or protein can still be sufficient to maintain other pathways, such as a pathway that is critical for the host microbial organism to survive, reproduce or grow. Attenuation of an enzyme or protein can also be weakening, reducing or diminishing the activity or amount of the enzyme or protein in an amount that is sufficient to increase yield of a fatty alcohol, fatty aldehyde or fatty acid product of the invention, but does not necessarily mimic complete disruption of the enzyme or protein.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one nucleic acid is included in a microbial organism that the more than one nucleic acids refers to the referenced encoding nucleic acid or biosynthetic activity, as discussed above. In some embodiments, the nucleic acid is an exogenous nucleic acid. In other embodiments, the nucleic acid is an endogenous nucleic acid. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having succinate biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionally related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

3.2 Microbial Organisms that Utilize Reducing Equivalents Produced by the Metabolism of Methanol Provided herein are methanol metabolic pathways engineered to improve the availability of reducing equivalents, which can be used for the production of product molecules. Exemplary product molecules include, without limitation, succinate, although given the teachings and guidance provided herein, it will be recognized by one skilled in the art that any product molecule that utilizes reducing equivalents in its production can exhibit enhanced production through the biosynthetic pathways provided herein.

Methanol is a relatively inexpensive organic feedstock that can be derived from synthesis gas components, CO and $H_2$, via catalysis. Methanol can be used as a source of reducing equivalents to increase the molar yield of product molecules from carbohydrates.

Succinate is a compound of commercial interest due to its use as a precursor to commodity chemicals in the food, pharmaceutical, detergent and polymer industries. Biological succinate production is also a green process where the greenhouse gas $CO_2$ must be fixed into succinate during sugar fermentation.

Despite efforts to develop bacterial strains producing increased succinate yields, many approaches previously employed have several drawbacks which hinder applicability in commercial settings. For example, many such strains generally are unstable in commercial fermentation processes due to selective pressures favoring the unaltered or wild-type parental counterparts.

Thus, there exists a need for microorganisms having commercially beneficial characteristics of increased production of succinate. The present invention satisfies this need and provides related advantages as well.

Accordingly, provided herein is bioderived succinate produced according to the methods described herein and biobased products comprising or obtained using the bioderived succinate. The biobased product can comprise at least 5%, at least 10%, at least 20%, at least 30%, at least 40% or at least 50% bioderived succinate. The biobased product can comprises a portion of said bioderived succinate as a repeating unit. The biobased product can be a a molded product obtained by molding the biobased product.

Figure 2:
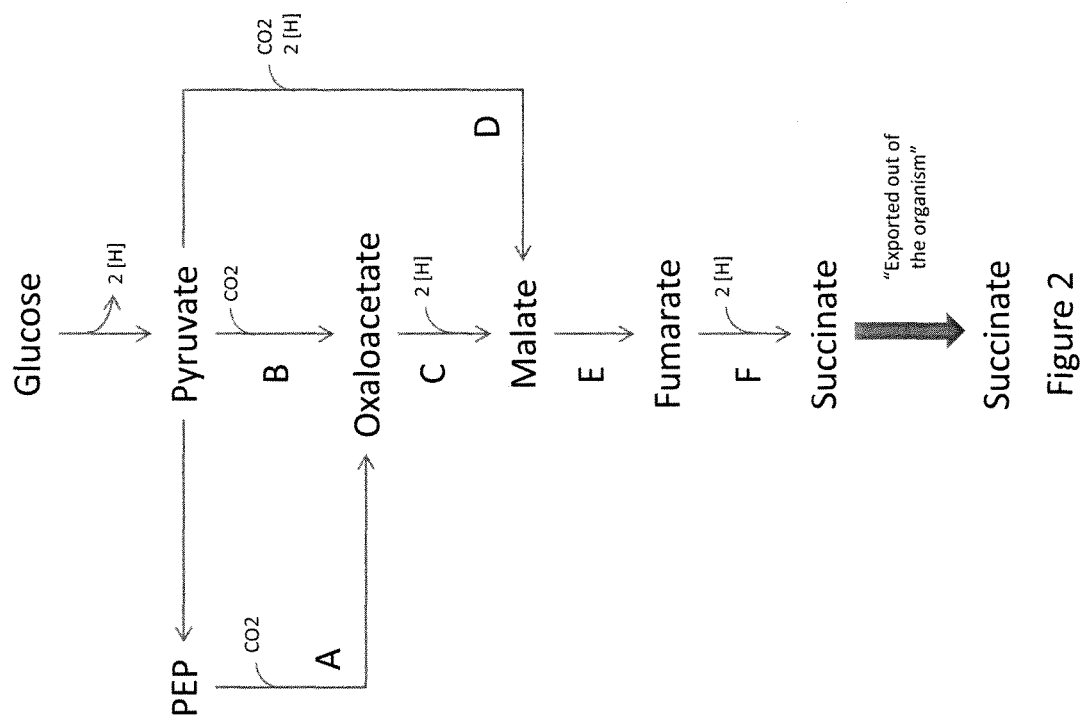

In numerous engineered pathways, realization of maximum product yields based on carbohydrate feedstock is hampered by insufficient reducing equivalents or by loss of reducing equivalents to byproducts. Methanol is a relatively inexpensive organic feedstock that can be used to generate reducing equivalents by employing one or more methanol metabolic enzymes as shown in FIG. 1. The reducing equivalents produced by the metabolism of methanol by one or more of the methanol metabolic pathways can then be used to power the glucose to succinate production pathways, for example, as shown in FIG. 2.

The product yields per C-mol of substrate of microbial cells synthesizing reduced fermentation products such as succinate are limited by insufficient reducing equivalents in the carbohydrate feedstock. Reducing equivalents, or electrons, can be extracted from methanol using one or more of the enzymes described in FIG. 1. The reducing equivalents are then passed to acceptors such as oxidized ferredoxins, oxidized quinones, oxidized cytochromes, NAD(P)+, water, or hydrogen peroxide to form reduced ferredoxin, reduced quinones, reduced cytochromes, NAD(P)H, $H_2$, or water, respectively. Reduced ferredoxin, reduced quinones and NAD(P)H are particularly useful as they can serve as redox carriers for various Wood-Ljungdahl pathway, reductive TCA cycle, or product pathway enzymes.

Specific examples of how additional redox availability from methanol can improve the yield of reduced products such as succinate are shown.

Succinate can be produced solely from sugars such as glucose and $CO_2$ with a maximum theoretical yield of 1.71 mol succinate/mol glucose or 1.12 g/g.

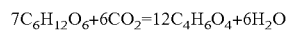

Identical or similar g/g yields are achievable on other carbohydrates (for example, xylose and arabinose).

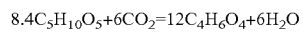

Alternatively, assuming that an ample source of reducing equivalents (for example, CO or $H_2$) is present, succinate can be produced completely from CO or $CO_2$ via the reductive TCA (rTCA) cycle, associated anapleurotic reactions, and enzymes for the extraction of reducing equivalents from CO and/or $H_2$.

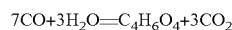

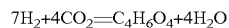

When both feedstocks of sugar and methanol are available, the methanol can be utilized to generate reducing equivalents by employing one or more of the enzymes shown in FIG. 1. The reducing equivalents generated from methanol can be utilized to power the glucose to succinate production pathways, e.g., as shown in FIG. 2. Theoretically, all carbons in glucose will be conserved, thus resulting in a maximal theoretical yield to produce succinate from glucose at 2 mol succinate per mol of glucose under either aerobic or anaerobic conditions as shown in FIG. 2:

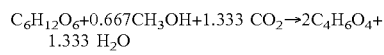

Supplementing carbohydrate feeds with external reducing equivalents is an attractive option for production of succinate through the reductive TCA cycle. A reductive TCA succinate pathway is particularly useful for the engineering of a eukaryotic organism (e.g., *Saccharomyces cerevisiae*) for the production of succinate, as reactions associated with the conversion of oxaloacetate to alpha-ketoglutarate or pyruvate to acetyl-CoA are not required. Eukaryotic organisms are advantaged over some bacterial species (e.g., *Escherichia coli*) in that they can tolerate lower pH conditions. Production of succinate at a pH lower than the pKa's of the acid groups ($pK_{a1}$=4.2, $pK_{a2}$=5.6) is desirable since a higher percentage of final product will be in the acid form (i.e., succinic acid) and not the salt form.

A major challenge associated with engineering a eukaryotic organism to achieve a high yield of succinate from carbohydrates alone is that several requisite enzymes are not exclusively localized to the cytosol. In fact, enzymes such as pyruvate dehydrogenase and citrate synthase are predominantly mitochondrial or peroxisomal. Thus, engineering a eukaryotic organism to achieve a high yield of succinate would require shuttling of metabolic precursors across cellular compartments or extensive strain engineering to localize several of the requisite enzymes to one compartment, preferably the cytosol. This embodiment provides a means of simplifying the pathway engineering by limiting the number of TCA cycle enzymes that are required to carry high flux. One can thus envision the development of a succinate producing microorganism in which most, if not all, of the enzymes in FIG. 1 are cytosolic.

In a first aspect, provided herein is a non-naturally occurring microbial organism having a methanol metabolic pathway, wherein said organism comprises at least one exogenous nucleic acid encoding a methanol metabolic pathway enzyme expressed in a sufficient amount to enhance the availability of reducing equivalents in the presence of methanol. In certain embodiments, the methanol metabolic pathway comprises one or more enzymes selected from the group consisting of a methanol methyltransferase; a methylenetetrahydrofolate reductase; a methylenetetrahydrofolate dehydrogenase; a methenyltetrahydrofolate cyclohydrolase; a formyltetrahydrofolate deformylase; a formyltetrahydrofolate synthetase; a formate hydrogen lyase; a hydrogenase; a formate dehydrogenase; a methanol dehydrogenase; a formaldehyde activating enzyme; a formaldehyde dehydrogenase; a S-(hydroxymethyl)glutathione synthase; a glutathione-dependent formaldehyde dehydrogenase; and an S-formylglutathione hydrolase. Such organisms advantageously allow for the production of reducing equivalents, which can then be used by the organism for the production of succinate using any one of the succinate pathways provided herein.

In certain embodiments, the methanol metabolic pathway comprises 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, and 1O, thereof, wherein 1A is a methanol methyltransferase; 1B is a methylenetetrahydrofolate reductase; 1C is a methylenetetrahydrofolate dehydrogenase; 1D is a methenyltetrahydrofolate cyclohydrolase; 1E is a formyltetrahydrofolate deformylase; 1F is a formyltetrahydrofolate synthetase; 1G is a formate hydrogen lyase; 1H is a hydrogenase, 1I is a formate dehydrogenase; 1J is a methanol dehydrogenase; 1K is a formaldehyde activating enzyme; 1L is a formaldehyde dehydrogenase; 1M is a S-(hydroxymethyl)glutathione synthase; 1N is glutathione-dependent formaldehyde dehydrogenase; and 1O is S-formylglutathione hydrolase. In some embodiments, 1K is spontaneous. In other embodiments, 1K is a formaldehyde activating enzyme. In some embodiments, 1M is spontaneous. In other embodiments, 1M is a S-(hydroxymethyl) glutathione synthase.

In one embodiment, the methanol metabolic pathway comprises 1A. In another embodiment, the methanol metabolic pathway comprises 1B. In another embodiment, the methanol metabolic pathway comprises 1C. In yet another embodiment, the methanol metabolic pathway comprises 1D. In one embodiment, the methanol metabolic pathway comprises 1E. In another embodiment, the methanol metabolic pathway comprises 1F. In another embodiment, the methanol metabolic pathway comprises 1G. In yet another embodiment, the methanol metabolic pathway comprises 1H. In one embodiment, the methanol metabolic pathway comprises 1I. In another embodiment, the methanol metabolic pathway comprises 1J. In another embodiment, the methanol metabolic pathway comprises 1K. In yet another embodiment, the methanol metabolic pathway comprises 1L. In yet another embodiment, the methanol metabolic pathway comprises 1M. In another embodiment, the methanol metabolic pathway comprises 1N. In yet another embodiment, the methanol metabolic pathway comprises 1O. Any combination of two, three, four, five, six, seven, eight, nine, ten, eleven, twelve, thirteen, fourteen or fifteen methanol metabolic pathway enzymes 1A, 1B, 1C, 1D, 1E, 1F, 1G, 1H, 1I, 1J, 1K, 1L, 1M, 1N, and 1O is also contemplated.

In some embodiments, the methanol metabolic pathway is a methanol metabolic pathway depicted in FIG. 1.

In one aspect, provided herein is a non-naturally occurring microbial organism having a methanol metabolic pathway, wherein said organism comprises at least one exogenous nucleic acid encoding a methanol metabolic pathway enzyme expressed in a sufficient amount to enhance the availability of reducing equivalents in the presence of methanol, wherein said methanol metabolic pathway comprises: (i) 1A and 1B, (ii) 1J; or (iii) 1J and 1K. In one embodiment, the methanol metabolic pathway comprises 1A and 1B. In another embodiment, the methanol metabolic pathway comprises 1J. In one embodiment, the methanol metabolic pathway comprises 1J and 1K. In certain embodiments, the methanol metabolic pathway comprises 1A, 1B, 1C, 1D, and 1E. In some embodiments. the methanol metabolic pathway comprises 1A, 1B, 1C, 1D and 1F. In some embodiments, the methanol metabolic pathway comprises 1J, 1C, 1D and 1E. In one embodiment, the methanol metabolic pathway comprises 1J, 1C, 1D and 1F. In another embodiment, the methanol metabolic pathway comprises 1J and 1L. In yet another embodiment, the methanol metabolic pathway comprises 1J, 1M, 1N and 1O. In certain embodiments, the methanol metabolic pathway comprises 1J, 1N and 1O. In some embodiments, the methanol metabolic pathway comprises 1J, 1K, 1C, 1D and 1E. In one embodiment, the methanol metabolic pathway comprises 1J, 1K, 1C, 1D and 1F. In some embodiments, 1K is spontaneous. In other embodiments, 1K is a formaldehyde activating enzyme. In some embodiments, 1M is spontaneous. In other embodiments, 1M is a S-(hydroxymethyl)glutathione synthase.

In certain embodiments, the methanol metabolic pathway comprises 1I. In certain embodiments, the methanol metabolic pathway comprises 1A, 1B, 1C, 1D, 1E and 1I. In some embodiments. the methanol metabolic pathway comprises 1A, 1B, 1C, 1D, 1F and 1I. In some embodiments, the methanol metabolic pathway comprises 1J, 1C, 1D, 1E and 1I. In one embodiment, the methanol metabolic pathway comprises 1J, 1C, 1D, 1F and 1I. In another embodiment, the methanol metabolic pathway comprises 1J, 1L and 1I. In yet another embodiment, the methanol metabolic pathway comprises 1J, 1M, 1N, 1O and 1I. In certain embodiments, the methanol metabolic pathway comprises 1J, 1N, 1O and 1I. In some embodiments, the methanol metabolic pathway comprises 1J, 1K, 1C, 1D, 1E and 1I. In one embodiment, the methanol metabolic pathway comprises 1J, 1K, 1C, 1D, 1F and 1I. In some embodiments, 1K is spontaneous. In other embodiments, 1K is a formaldehyde activating enzyme. In some embodiments, 1M is spontaneous. In other embodiments, 1M is a S-(hydroxymethyl)glutathione synthase.

In certain embodiments, the methanol metabolic pathway comprises 1G. In certain embodiments, the methanol metabolic pathway comprises 1A, 1B, 1C, 1D, 1E and 1G. In some embodiments. the methanol metabolic pathway comprises 1A, 1B, 1C, 1D, 1F and 1G. In some embodiments, the methanol metabolic pathway comprises 1J, 1C, 1D, 1E and 1G. In one embodiment, the methanol metabolic pathway comprises 1J, 1C, 1D, 1F and 1G. In another embodiment, the methanol metabolic pathway comprises 1 J, 1L and 1G. In yet another embodiment, the methanol metabolic pathway comprises 1J, 1M, 1N, 1O and 1G. In certain embodiments, the methanol metabolic pathway comprises 1J, 1N, 1O and 1G. In some embodiments, the methanol metabolic pathway comprises 1J, 1K, 1C, 1D, 1E and 1G. In one embodiment, the methanol metabolic pathway comprises 1J, 1K, 1C, 1D, 1F and 1G. In some embodiments, 1K is spontaneous. In other embodiments, 1K is a formaldehyde activating enzyme. In some embodiments, 1M is spontaneous. In other embodiments, 1M is a S-(hydroxymethyl) glutathione synthase.

In certain embodiments, the methanol metabolic pathway comprises 1G and 1H. In certain embodiments, the methanol metabolic pathway comprises 1A, 1B, 1C, 1D, 1E, 1G and 1H. In some embodiments. the methanol metabolic pathway comprises 1A, 1B, 1C, 1D, 1F, 1G and 1H. In some embodiments, the methanol metabolic pathway comprises 1J, 1C, 1D, 1E, 1G and 1H. In one embodiment, the methanol metabolic pathway comprises 1J, 1C, 1D, 1F, 1G and 1H. In another embodiment, the methanol metabolic pathway comprises 1J, 1L, 1G and 1H. In yet another embodiment, the methanol metabolic pathway comprises 1J, 1M, 1N, 1O, 1G and 1H. In certain embodiments, the methanol metabolic pathway comprises 1J, 1N, 1O, 1G and 1H. In some embodiments, the methanol metabolic pathway comprises 1J, 1K, 1C, 1D, 1E, 1G and 1H. In one embodiment, the methanol metabolic pathway comprises 1J, 1K, 1C, 1D, 1F, 1G and 1H. In some embodiments, 1K is spontaneous. In other embodiments, 1K is a formaldehyde activating enzyme. In some embodiments, 1M is spontaneous. In other embodiments, 1M is a S-(hydroxymethyl) glutathione synthase.

In certain embodiments, the formation of 5-hydroxymethylglutathione from formaldehyde is spontaneous (see, e.g., FIG. 1, step M). In some embodiments, the formation of 5-hydroxymethylglutathione from formaldehyde is catalyzed by a S-(hydroxymethyl)glutathione synthase (see, e.g., FIG. 1, step M). In certain embodiments, the formation of methylene-THF from formaldehyde is spontaneous (see, e.g., FIG. 1, step K). In certain embodiments, the formation of methylene-THF from formaldehyde is catalyzed by a formaldehyde activating enzyme (see, e.g., FIG. 1, step K).

In certain embodiments, the organism comprises two, three, four, five, six or seven exogenous nucleic acids, each encoding a methanol metabolic pathway enzyme. In certain embodiments, the organism comprises two exogenous nucleic acids, each encoding a methanol metabolic pathway enzyme. In certain embodiments, the organism comprises three exogenous nucleic acids, each encoding a methanol metabolic pathway enzyme. In certain embodiments, the organism comprises four exogenous nucleic acids, each encoding a methanol metabolic pathway enzyme. In certain embodiments, the organism comprises five exogenous nucleic acids, each encoding a methanol metabolic pathway enzyme. In certain embodiments, the organism comprises six exogenous nucleic acids, each encoding a methanol metabolic pathway enzyme. In certain embodiments, the organism comprises seven exogenous nucleic acids, each encoding a methanol metabolic pathway enzyme.

Any non-naturally occurring eukaryotic organism comprising a methanol metabolic pathway and engineered to comprise a methanol metabolic pathway enzyme, such as those provided herein, can be engineered to further comprise one or more succinate pathway enzymes.

In one embodiment, the non-naturally occurring microbial organism further comprises a succinate pathway. In some embodiments, the organism further comprises at least one nucleic acid encoding a succinate pathway enzyme expressed in a sufficient amount to produce succinate. In some embodiments, the nucleic acid is an exogenous nucleic acid. In other embodiments, the nucleic acid is an endogenous nucleic acid. In certain embodiments, the succinate pathway enzyme is selected from the group consisting of a PEP carboxylase or a PEP carboxykinase; a pyruvate carboxylase; a malate dehydrogenase; a malic enzyme; a fumarase; and a fumarate reductase.

In some embodiments, the non-naturally occurring microbial organisms having a succinate pathway includes a set of succinate pathway enzymes.

Enzymes, genes and methods for engineering pathways from glucose to various products, such as succinate, into a microorganism, are now known in the art (see, e.g., U.S. Publ. No. 2011/0201089, which is herein incorporated by reference in its entirety). A set of succinate pathway enzymes represents a group of enzymes that can convert pyruvate or phosphoenolpyruvate to succinate, for example, as shown in FIG. 2. The additional reducing equivalents obtained from the methanol metabolic pathways, as disclosed herein, improve the yields of all these products when utilizing carbohydrate-based feedstock.

Exemplary enzymes for the conversion glucose to succinate (e.g., via pyruvate) include a phosphoenolpyruvate (PEP) carboxylase or a PEP carboxykinase (FIG. 2, step A); a pyruvate carboxylase (FIG. 2, step B); a malate dehydrogenase (FIG. 2, step C); a malic enzyme (FIG. 2, step D); a fumarase (FIG. 2, step E); and a fumarate reductase (FIG. 2, step F).

In one aspect, provided herein is a non-naturally occurring microbial organism, comprising (1) a methanol metabolic pathway, wherein said organism comprises at least one exogenous nucleic acid encoding a methanol metabolic pathway enzyme in a sufficient amount to enhance the availability of reducing equivalents in the presence of methanol; and (2) a succinate pathway. In some embodiments, the organism further comprises at least one nucleic acid (e.g., an endogenous and/or exogenous nucleic acid) encoding a succinate pathway enzyme expressed in a sufficient amount to produce succinate. In one embodiment, the at least one exogenous nucleic acid encoding the methanol metabolic pathway enzyme enhances the availability of reducing equivalents in the presence of methanol in a sufficient amount to increase the amount of succinate produced by the non-naturally microbial organism. In some embodiments, the methanol metabolic pathway comprises any of the various combinations of methanol metabolic pathway enzymes described above or elsewhere herein.

In certain embodiments, (1) the methanol metabolic pathway comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is a methanol methyltransferase; 1B is a methylenetetrahydrofolate reductase; 1C is a methylenetetrahydrofolate dehydrogenase; 1D is a methenyltetrahydrofolate cyclohydrolase; 1E is a formyltetrahydrofolate deformylase; 1F is a formyltetrahydrofolate synthetase; 1G is a formate hydrogen lyase; 1H is a hydrogenase, 1I is a formate dehydrogenase; 1J is a methanol dehydrogenase; 1K is spontaneous or formaldehyde activating enzyme; 1L is a formaldehyde dehydrogenase; 1M is spontaneous or a S-(hydroxymethyl)glutathione synthase; 1N is glutathione-dependent formaldehyde dehydrogenase and 1O is S-formylglutathione hydrolase; and (2) the succinate pathway comprises 2A, 2B, 2C, 2D, 2E or 2F, or any combination thereof, wherein 2A is a PEP carboxylase or a PEP carboxykinase; 2B is a pyruvate carboxylase; 2C is a malate dehydrogenase; 2D is a malic enzyme; 2E is a fumarase; and 2F is a fumarate reductase. In some embodiments, 1K is spontaneous. In other embodiments, 1K is a formaldehyde activating enzyme. In some embodiments, 1M is spontaneous. In other embodiments, 1M is a S-(hydroxymethyl)glutathione synthase. In some embodiments, 2A is a PEP carboxylase. In other embodiments, 2A is a PEP carboxykinase.

In one embodiment, the succinate pathway comprises 2A. In another embodiment, the succinate pathway comprises 2B. In an embodiment, the succinate pathway comprises 2C. In another embodiment, the succinate pathway comprises 2D. In another embodiment, the succinate pathway comprises 2E. In an embodiment, the succinate pathway comprises 2F. Any combination of two, three, four, five or six succinate pathway enzymes 2A, 2B, 2C, 2D, 2E and 2F is also contemplated. In some embodiments, 2A is a PEP carboxylase. In other embodiments, 2A is a PEP carboxykinase.

In some embodiments, the methanol metabolic pathway is a methanol metabolic pathway depicted in FIG. 1, and the succinate pathway is a succinate pathway depicted in FIG. 2.

Exemplary sets of succinate pathway enzymes to convert glucose to succinate (e.g., via pyruvate or phosphoenolpyruvate) according to FIG. 2 include (i) 2A, 2C, 2E and 2F; (ii) 2B, 2C, 2E and 2F; and (iii) 2D, 2E and 2F. In some embodiments, 2A is a PEP carboxylase. In other embodiments, 2A is a PEP carboxykinase.

In one embodiment, (1) the methanol metabolic pathway comprises 1A and 1B; and (2) the succinate pathway comprises 2A, 2C, 2E and 2F. In another embodiment, (1) the methanol metabolic pathway comprises 1J; and (2) the succinate pathway comprises 2A, 2C, 2E and 2F. In one embodiment, (1) the methanol metabolic pathway comprises 1J and 1K; and (2) the succinate pathway comprises 2A, 2C, 2E and 2F. In certain embodiments, (1) the methanol metabolic pathway comprises 1A, 1B, 1C, 1D, and 1E; and (2) the succinate pathway comprises 2A, 2C, 2E and 2F. In some embodiments, (1) the methanol metabolic pathway comprises 1A, 1B, 1C, 1D and 1F; and (2) the succinate pathway comprises 2A, 2C, 2E and 2F. In some embodiments, (1) the methanol metabolic pathway comprises 1J, 1C, 1D and 1E; and (2) the succinate pathway comprises 2A, 2C, 2E and 2F. In one embodiment, (1) the methanol metabolic pathway comprises 1J, 1C, 1D and 1F; and (2) the succinate pathway comprises 2A, 2C, 2E and 2F. In another embodiment, (1) the methanol metabolic pathway comprises 1J and 1L; and (2) the succinate pathway comprises 2A, 2C, 2E and 2F. In yet another embodiment, (1) the methanol metabolic pathway comprises 1J, 1M, 1N and 1O; and (2) the succinate pathway comprises 2A, 2C, 2E and 2F. In certain embodiments, (1) the methanol metabolic pathway comprises 1J, 1N and 1O; and (2) the succinate pathway comprises 2A, 2C, 2E and 2F. In some embodiments, (1) the methanol metabolic pathway comprises 1J, 1K, 1C, 1D and 1E; and (2) the succinate pathway comprises 2A, 2C, 2E and 2F. In one embodiment, (1) the methanol metabolic pathway comprises 1J, 1K, 1C, 1D and 1F; and (2) the succinate pathway comprises 2A, 2C, 2E and 2F. In certain embodiments, (1) the methanol metabolic pathway comprises 1I; and (2) the succinate pathway comprises 2A, 2C, 2E and 2F. In certain embodiments, (1) the methanol metabolic pathway comprises 1A, 1B, 1C, 1D, 1E and 1I; and (2) the succinate pathway comprises 2A, 2C, 2E and 2F. In some embodiments, (1) the methanol metabolic pathway comprises 1A, 1B, 1C, 1D, 1F and 1I; and (2) the succinate pathway comprises 2A, 2C, 2E and 2F. In some embodiments, (1) the methanol metabolic pathway comprises 1J, 1C, 1D, 1E and 1I; and (2) the succinate pathway comprises 2A, 2C, 2E and 2F. In one embodiment, (1) the methanol metabolic pathway comprises 1J, 1C, 1D, 1F and 1I; and (2) the succinate pathway comprises 2A, 2C, 2E and 2F. In another embodiment, (1) the methanol metabolic pathway comprises 1J, 1L and 1I; and (2) the succinate pathway comprises 2A, 2C, 2E and 2F. In yet another embodiment, (1) the methanol metabolic pathway comprises 1J, 1M, 1N, 1O and 1I; and (2) the succinate pathway comprises 2A, 2C, 2E and 2F. In certain embodiments, (1) the methanol metabolic pathway comprises 1J, 1N, 1O and 1I; and (2) the succinate pathway comprises 2A, 2C, 2E and 2F. In some embodiments, (1) the methanol metabolic pathway comprises 1J, 1K, 1C, 1D, 1E and 1I; and (2) the succinate pathway comprises 2A, 2C, 2E and 2F. In one embodiment, (1) the methanol metabolic pathway comprises 1J, 1K, 1C, 1D, 1F and 1I; and (2) the succinate pathway comprises 2A, 2C, 2E and 2F. In certain embodiments, (1) the methanol metabolic pathway comprises 1G; and (2) the succinate pathway comprises 2A, 2C, 2E and 2F. In certain embodiments, (1) the methanol metabolic pathway comprises 1A, 1B, 1C, 1D, 1E and 1G; and (2) the succinate pathway comprises 2A, 2C, 2E and 2F. In some embodiments, (1) the methanol metabolic pathway comprises 1A, 1B, 1C, 1D, 1F and 1G; and (2) the succinate pathway comprises 2A, 2C, 2E and 2F. In some embodiments, (1) the methanol metabolic pathway comprises 1J, 1C, 1D, 1E and 1G; and (2) the succinate pathway comprises 2A, 2C, 2E and 2F. In one embodiment, (1) the methanol metabolic pathway comprises 1J, 1C, 1D, 1F and 1G; and (2) the succinate pathway comprises 2A, 2C, 2E and 2F. In another embodiment, (1) the methanol metabolic pathway comprises 1J, 1L and 1G; and (2) the succinate pathway comprises 2A, 2C, 2E and 2F. In yet another embodiment, (1) the methanol metabolic pathway comprises 1J, 1M, 1N, 1O and 1G; and (2) the succinate pathway comprises 2A, 2C, 2E and 2F. In certain embodiments, (1) the methanol metabolic pathway comprises 1J, 1N, 1O and 1G; and (2) the succinate pathway comprises 2A, 2C, 2E and 2F. In some embodiments, (1) the methanol metabolic pathway comprises 1J, 1K, 1C, 1D, 1E and 1G; and (2) the succinate pathway comprises 2A, 2C, 2E and 2F. In one embodiment, (1) the methanol metabolic pathway comprises 1J, 1K, 1C, 1D, 1F and 1G; and (2) the succinate pathway comprises 2A, 2C, 2E and 2F. In certain embodiments, (1) the methanol metabolic pathway comprises 1G and 1H; and (2) the succinate pathway comprises 2A, 2C, 2E and 2F. In certain embodiments, (1) the methanol metabolic pathway comprises 1A, 1B, 1C, 1D, 1E, 1G and 1H; and (2) the succinate pathway comprises 2A, 2C, 2E and 2F. In some embodiments, (1) the methanol metabolic pathway comprises 1A, 1B, 1C, 1D, 1F, 1G and 1H; and (2) the succinate pathway comprises 2A, 2C, 2E and 2F. In some embodiments, (1) the methanol metabolic pathway comprises 1J, 1C, 1D, 1E, 1G and 1H; and (2) the succinate pathway comprises 2A, 2C, 2E and 2F. In one embodiment, (1) the methanol metabolic pathway comprises 1J, 1C, 1D, 1F, 1G and 1H; and (2) the succinate pathway comprises 2A, 2C, 2E and 2F. In another embodiment, (1) the methanol metabolic pathway comprises 1J, 1L, 1G and 1H; and (2) the succinate pathway comprises 2A, 2C, 2E and 2F. In yet another embodiment, (1) the methanol metabolic pathway comprises 1J, 1M, 1N, 1O, 1G and 1H; and (2) the succinate pathway comprises 2A, 2C, 2E and 2F. In certain embodiments, (1) the methanol metabolic pathway comprises 1J, 1N, 1O, 1G and 1H; and (2) the succinate pathway comprises 2A, 2C, 2E and 2F. In some embodiments, (1) the methanol metabolic pathway comprises 1J, 1K, 1C, 1D, 1E, 1G and 1H; and (2) the succinate pathway comprises 2A, 2C, 2E and 2F. In one embodiment, (1) the methanol metabolic pathway comprises 1J, 1K, 1C, 1D, 1F, 1G and 1H; and (2) the succinate pathway comprises 2A, 2C, 2E and 2F. In some embodiments, 1K is spontaneous. In other embodiments, 1K is a formaldehyde activating enzyme. In some embodiments, 1M is spontaneous. In other embodiments, 1M is a S-(hydroxymethyl)glutathione synthase. In some embodiments, 2A is a PEP carboxylase. In other embodiments, 2A is a PEP carboxykinase.

In one embodiment, (1) the methanol metabolic pathway comprises 1A and 1B; and (2) the succinate pathway comprises 2B, 2C, 2E and 2F. In another embodiment, (1) the methanol metabolic pathway comprises 1J; and (2) the succinate pathway comprises 2B, 2C, 2E and 2F. In one embodiment, (1) the methanol metabolic pathway comprises 1J and 1K; and (2) the succinate pathway comprises 2B, 2C, 2E and 2F. In certain embodiments, (1) the methanol metabolic pathway comprises 1A, 1B, 1C, 1D, and 1E; and (2) the succinate pathway comprises 2B, 2C, 2E and 2F. In some embodiments, (1) the methanol metabolic pathway comprises 1A, 1B, 1C, 1D and 1F; and (2) the succinate pathway comprises 2B, 2C, 2E and 2F. In some embodiments, (1) the methanol metabolic pathway comprises 1J, 1C, 1D and 1E; and (2) the succinate pathway comprises 2B, 2C, 2E and 2F. In one embodiment, (1) the methanol metabolic pathway comprises 1J, 1C, 1D and 1F; and (2) the succinate pathway comprises 2B, 2C, 2E and 2F. In another embodiment, (1) the methanol metabolic pathway comprises 1J and 1L; and (2) the succinate pathway comprises 2B, 2C, 2E and 2F. In yet another embodiment, (1) the methanol metabolic pathway comprises 1J, 1M, 1N and 1O; and (2) the succinate pathway comprises 2B, 2C, 2E and 2F. In certain embodiments, (1) the methanol metabolic pathway comprises 1J, 1N and 1O; and (2) the succinate pathway comprises 2B, 2C, 2E and 2F. In some embodiments, (1) the methanol metabolic pathway comprises 1J, 1K, 1C, 1D and 1E; and (2) the succinate pathway comprises 2B, 2C, 2E and 2F. In one embodiment, (1) the methanol metabolic pathway comprises 1J, 1K, 1C, 1D and 1F; and (2) the succinate pathway comprises 2B, 2C, 2E and 2F. In certain embodiments, (1) the methanol metabolic pathway comprises 1I; and (2) the succinate pathway comprises 2B, 2C, 2E and 2F. In certain embodiments, (1) the methanol metabolic pathway comprises 1A, 1B, 1C, 1D, 1E and 1I; and (2) the succinate pathway comprises 2B, 2C, 2E and 2F. In some embodiments, (1) the methanol metabolic pathway comprises 1A, 1B, 1C, 1D, 1F and 1I; and (2) the succinate pathway comprises 2B, 2C, 2E and 2F. In some embodiments, (1) the methanol metabolic pathway comprises 1J, 1C, 1D, 1E and 1I; and (2) the succinate pathway comprises 2B, 2C, 2E and 2F. In one embodiment, (1) the methanol metabolic pathway comprises 1J, 1C, 1D, 1F and 1I; and (2) the succinate pathway comprises 2B, 2C, 2E and 2F. In another embodiment, (1) the methanol metabolic pathway comprises 1J, 1L and 1I; and (2) the succinate pathway comprises 2B, 2C, 2E and 2F. In yet another embodiment, (1) the methanol metabolic pathway comprises 1J, 1M, 1N, 1O and 1I; and (2) the succinate pathway comprises 2B, 2C, 2E and 2F. In certain embodiments, (1) the methanol metabolic pathway comprises 1J, 1N, 1O and 1I; and (2) the succinate pathway comprises 2B, 2C, 2E and 2F. In some embodiments, (1) the methanol metabolic pathway comprises 1J, 1K, 1C, 1D, 1E and 1I; and (2) the succinate pathway comprises 2B, 2C, 2E and 2F. In one embodiment, (1) the methanol metabolic pathway comprises 1J, 1K, 1C, 1D, 1F and 1I; and (2) the succinate pathway comprises 2B, 2C, 2E and 2F. In certain embodiments, (1) the methanol metabolic pathway comprises 1G; and (2) the succinate pathway comprises 2B, 2C, 2E and 2F. In certain embodiments, (1) the methanol metabolic pathway comprises 1A, 1B, 1C, 1D, 1E and 1G; and (2) the succinate pathway comprises 2B, 2C, 2E and 2F. In some embodiments, (1) the methanol metabolic pathway comprises 1A, 1B, 1C, 1D, 1F and 1G; and (2) the succinate pathway comprises 2B, 2C, 2E and 2F. In some embodiments, (1) the methanol metabolic pathway comprises 1J, 1C, 1D, 1E and 1G; and (2) the succinate pathway comprises 2B, 2C, 2E and 2F. In one embodiment, (1) the methanol metabolic pathway comprises 1J, 1C, 1D, 1F and 1G; and (2) the succinate pathway comprises 2B, 2C, 2E and 2F. In another embodiment, (1) the methanol metabolic pathway comprises 1J, 1L and 1G; and (2) the succinate pathway comprises 2B, 2C, 2E and 2F. In yet another embodiment, (1) the methanol metabolic pathway comprises 1J, 1M, 1N, 1O and 1G; and (2) the succinate pathway comprises 2B, 2C, 2E and 2F. In certain embodiments, (1) the methanol metabolic pathway comprises 1J, 1N, 1O and 1G; and (2) the succinate pathway comprises 2B, 2C, 2E and 2F. In some embodiments, (1) the methanol metabolic pathway comprises 1J, 1K, 1C, 1D, 1E and 1G; and (2) the succinate pathway comprises 2B, 2C, 2E and 2F. In one embodiment, (1) the methanol metabolic pathway comprises 1J, 1K, 1C, 1D, 1F and 1G; and (2) the succinate pathway comprises 2B, 2C, 2E and 2F. In certain embodiments, (1) the methanol metabolic pathway comprises 1G and 1H; and (2) the succinate pathway comprises 2B, 2C, 2E and 2F. In certain embodiments, (1) the methanol metabolic pathway comprises 1A, 1B, 1C, 1D, 1E, 1G and 1H; and (2) the succinate pathway comprises 2B, 2C, 2E and 2F. In some embodiments, (1) the methanol metabolic pathway comprises 1A, 1B, 1C, 1D, 1F, 1G and 1H; and (2) the succinate pathway comprises 2B, 2C, 2E and 2F. In some embodiments, (1) the methanol metabolic pathway comprises 1J, 1C, 1D, 1E, 1G and 1H; and (2) the succinate pathway comprises 2B, 2C, 2E and 2F. In one embodiment, (1) the methanol metabolic pathway comprises 1J, 1C, 1D, 1F, 1G and 1H; and (2) the succinate pathway comprises 2B, 2C, 2E and 2F. In another embodiment, (1) the methanol metabolic pathway comprises 1J, 1L, 1G and 1H; and (2) the succinate pathway comprises 2B, 2C, 2E and 2F. In yet another embodiment, (1) the methanol metabolic pathway comprises 1J, 1M, 1N, 1O, 1G and 1H; and (2) the succinate pathway comprises 2B, 2C, 2E and 2F. In certain embodiments, (1) the methanol metabolic pathway comprises 1J, 1N, 1O, 1G and 1H; and (2) the succinate pathway comprises 2B, 2C, 2E and 2F. In some embodiments, (1) the methanol metabolic pathway comprises 1J, 1K, 1C, 1D, 1E, 1G and 1H; and (2) the succinate pathway comprises 2B, 2C, 2E and 2F. In one embodiment, (1) the methanol metabolic pathway comprises 1J, 1K, 1C, 1D, 1F, 1G and 1H; and (2) the succinate pathway comprises 2B, 2C, 2E and 2F. In some embodiments, 1K is spontaneous. In other embodiments, 1K is a formaldehyde activating enzyme. In some embodiments, 1M is spontaneous. In other embodiments, 1M is a S-(hydroxymethyl)glutathione synthase.

In one embodiment, (1) the methanol metabolic pathway comprises 1A and 1B; and (2) the succinate pathway comprises 2D, 2E and 2F. In another embodiment, (1) the methanol metabolic pathway comprises 1J; and (2) the succinate pathway comprises 2D, 2E and 2F. In one embodiment, (1) the methanol metabolic pathway comprises 1J and 1K; and (2) the succinate pathway comprises 2D, 2E and 2F. In certain embodiments, (1) the methanol metabolic pathway comprises 1A, 1B, 1C, 1D, and 1E; and (2) the succinate pathway comprises 2D, 2E and 2F. In some embodiments, (1) the methanol metabolic pathway comprises 1A, 1B, 1C, 1D and 1F; and (2) the succinate pathway comprises 2D, 2E and 2F. In some embodiments, (1) the methanol metabolic pathway comprises 1J, 1C, 1D and 1E;

and (2) the succinate pathway comprises 2D, 2E and 2F. In one embodiment, (1) the methanol metabolic pathway comprises 1J, 1C, 1D and 1F; and (2) the succinate pathway comprises 2D, 2E and 2F. In another embodiment, (1) the methanol metabolic pathway comprises 1J and 1L; and (2) the succinate pathway comprises 2D, 2E and 2F. In yet another embodiment, (1) the methanol metabolic pathway comprises 1J, 1M, 1N and 1O; and (2) the succinate pathway comprises 2D, 2E and 2F. In certain embodiments, (1) the methanol metabolic pathway comprises 1J, 1N and 1O; and (2) the succinate pathway comprises 2D, 2E and 2F. In some embodiments, (1) the methanol metabolic pathway comprises 1J, 1K, 1C, 1D and 1E; and (2) the succinate pathway comprises 2D, 2E and 2F. In one embodiment, (1) the methanol metabolic pathway comprises 1J, 1K, 1C, 1D and 1F; and (2) the succinate pathway comprises 2D, 2E and 2F. In certain embodiments, (1) the methanol metabolic pathway comprises 1I; and (2) the succinate pathway comprises 2D, 2E and 2F. In certain embodiments, (1) the methanol metabolic pathway comprises 1A, 1B, 1C, 1D, 1E and 1I; and (2) the succinate pathway comprises 2D, 2E and 2F. In some embodiments, (1) the methanol metabolic pathway comprises 1A, 1B, 1C, 1D, 1F and 1I; and (2) the succinate pathway comprises 2D, 2E and 2F. In some embodiments, (1) the methanol metabolic pathway comprises 1J, 1C, 1D, 1E and 1I; and (2) the succinate pathway comprises 2D, 2E and 2F. In one embodiment, (1) the methanol metabolic pathway comprises 1J, 1C, 1D, 1F and 1I; and (2) the succinate pathway comprises 2D, 2E and 2F. In another embodiment, (1) the methanol metabolic pathway comprises 1J, 1L and 1I; and (2) the succinate pathway comprises 2D, 2E and 2F. In yet another embodiment, (1) the methanol metabolic pathway comprises 1J, 1M, 1N, 1O and 1I; and (2) the succinate pathway comprises 2D, 2E and 2F. In certain embodiments, (1) the methanol metabolic pathway comprises 1J, 1N, 1O and 1I; and (2) the succinate pathway comprises 2D, 2E and 2F. In some embodiments, (1) the methanol metabolic pathway comprises 1J, 1K, 1C, 1D, 1E and 1I; and (2) the succinate pathway comprises 2D, 2E and 2F. In one embodiment, (1) the methanol metabolic pathway comprises 1J, 1K, 1C, 1D, 1F and 1I; and (2) the succinate pathway comprises 2D, 2E and 2F. In certain embodiments, (1) the methanol metabolic pathway comprises 1G; and (2) the succinate pathway comprises 2D, 2E and 2F. In certain embodiments, (1) the methanol metabolic pathway comprises 1A, 1B, 1C, 1D, 1E and 1G; and (2) the succinate pathway comprises 2D, 2E and 2F. In some embodiments, (1) the methanol metabolic pathway comprises 1A, 1B, 1C, 1D, 1F and 1G; and (2) the succinate pathway comprises 2D, 2E and 2F. In some embodiments, (1) the methanol metabolic pathway comprises 1J, 1C, 1D, 1E and 1G; and (2) the succinate pathway comprises 2D, 2E and 2F. In one embodiment, (1) the methanol metabolic pathway comprises 1J, 1C, 1D, 1F and 1G; and (2) the succinate pathway comprises 2D, 2E and 2F. In another embodiment, (1) the methanol metabolic pathway comprises 1J, 1L and 1G; and (2) the succinate pathway comprises 2D, 2E and 2F. In yet another embodiment, (1) the methanol metabolic pathway comprises 1J, 1M, 1N, 1O and 1G; and (2) the succinate pathway comprises 2D, 2E and 2F. In certain embodiments, (1) the methanol metabolic pathway comprises 1J, 1N, 1O and 1G; and (2) the succinate pathway comprises 2D, 2E and 2F. In some embodiments, (1) the methanol metabolic pathway comprises 1J, 1K, 1C, 1D, 1E and 1G; and (2) the succinate pathway comprises 2D, 2E and 2F. In one embodiment, (1) the methanol metabolic pathway comprises 1J, 1K, 1C, 1D, 1F and 1G; and (2) the succinate pathway comprises 2D, 2E and 2F. In certain embodiments, (1) the methanol metabolic pathway comprises 1G and 1H; and (2) the succinate pathway comprises 2D, 2E and 2F. In certain embodiments, (1) the methanol metabolic pathway comprises 1A, 1B, 1C, 1D, 1E, 1G and 1H; and (2) the succinate pathway comprises 2D, 2E and 2F. In some embodiments, (1) the methanol metabolic pathway comprises 1A, 1B, 1C, 1D, 1F, 1G and 1H; and (2) the succinate pathway comprises 2D, 2E and 2F. In some embodiments, (1) the methanol metabolic pathway comprises 1J, 1C, 1D, 1E, 1G and 1H; and (2) the succinate pathway comprises 2D, 2E and 2F. In one embodiment, (1) the methanol metabolic pathway comprises 1J, 1C, 1D, 1F, 1G and 1H; and (2) the succinate pathway comprises 2D, 2E and 2F. In another embodiment, (1) the methanol metabolic pathway comprises 1J, 1L, 1G and 1H; and (2) the succinate pathway comprises 2D, 2E and 2F. In yet another embodiment, (1) the methanol metabolic pathway comprises 1J, 1M, 1N, 1O, 1G and 1H; and (2) the succinate pathway comprises 2D, 2E and 2F. In certain embodiments, (1) the methanol metabolic pathway comprises 1J, 1N, 1O, 1G and 1H; and (2) the succinate pathway comprises 2D, 2E and 2F. In some embodiments, (1) the methanol metabolic pathway comprises 1J, 1K, 1C, 1D, 1E, 1G and 1H; and (2) the succinate pathway comprises 2D, 2E and 2F. In one embodiment, (1) the methanol metabolic pathway comprises 1J, 1K, 1C, 1D, 1F, 1G and 1H; and (2) the succinate pathway comprises 2D, 2E and 2F. In some embodiments, 1K is spontaneous. In other embodiments, 1K is a formaldehyde activating enzyme. In some embodiments, 1M is spontaneous. In other embodiments, 1M is a S-(hydroxymethyl) glutathione synthase.

In one embodiment, the non-naturally occurring microbial organism comprises (1) a methanol metabolic pathway comprising 1A and 1B; 1J; 1J and 1K; 1A, 1B, 1C, 1D, and 1E; 1A, 1B, 1C, 1D and 1F; 1J, 1C, 1D and 1E; 1J, 1C, 1D and 1F; 1J and 1L; 1J, 1M, 1N and 1O; 1J, 1N and 1O; 1J, 1K, 1C, 1D and 1E; 1J, 1K, 1C, 1D and 1F; 1I; 1A, 1B, 1C, 1D, 1E and 1I; 1A, 1B, 1C, 1D, 1F and 1I; 1J, 1C, 1D, 1E and 1I; 1J, 1C, 1D, 1F and 1I; 1J, 1L and 1I; 1J, 1M, 1N, 1O and 1I; 1J, 1N, 1O and 1I; 1J, 1K, 1C, 1D, 1E and 1I; 1J, 1K, 1C, 1D, 1F and 1I; 1G; 1A, 1B, 1C, 1D, 1E and 1G; 1A, 1B, 1C, 1D, 1F and 1G; 1J, 1C, 1D, 1E and 1G; 1J, 1C, 1D, 1F and 1G; 1J, 1L and 1G; 1J, 1M, 1N, 1O and 1G; 1J, 1N, 1O and 1G; 1J, 1K, 1C, 1D, 1E and 1G; 1J, 1K, 1C, 1D, 1F and 1G; 1G and 1H; 1A, 1B, 1C, 1D, 1E, 1G and 1H; 1A, 1B, 1C, 1D, 1F, 1G and 1H; 1J, 1C, 1D, 1E, 1G and 1H; 1J, 1C, 1D, 1F, 1G and 1H; 1J, 1L, 1G and 1H; 1J, 1M, 1N, 1O, 1G and 1H; 1J, 1N, 1O, 1G and 1H; 1J, 1K, 1C, 1D, 1E, 1G and 1H; or 1J, 1K, 1C, 1D, 1F, 1G and 1H; and (2) a succinate pathway. In some embodiments, 1K is spontaneous. In other embodiments, 1K is a formaldehyde activating enzyme. In some embodiments, 1M is spontaneous. In other embodiments, 1M is a S-(hydroxymethyl)glutathione synthase.

Any methanol metabolic pathway provided herein can be combined with any succinate pathway provided herein.

Figure 3:
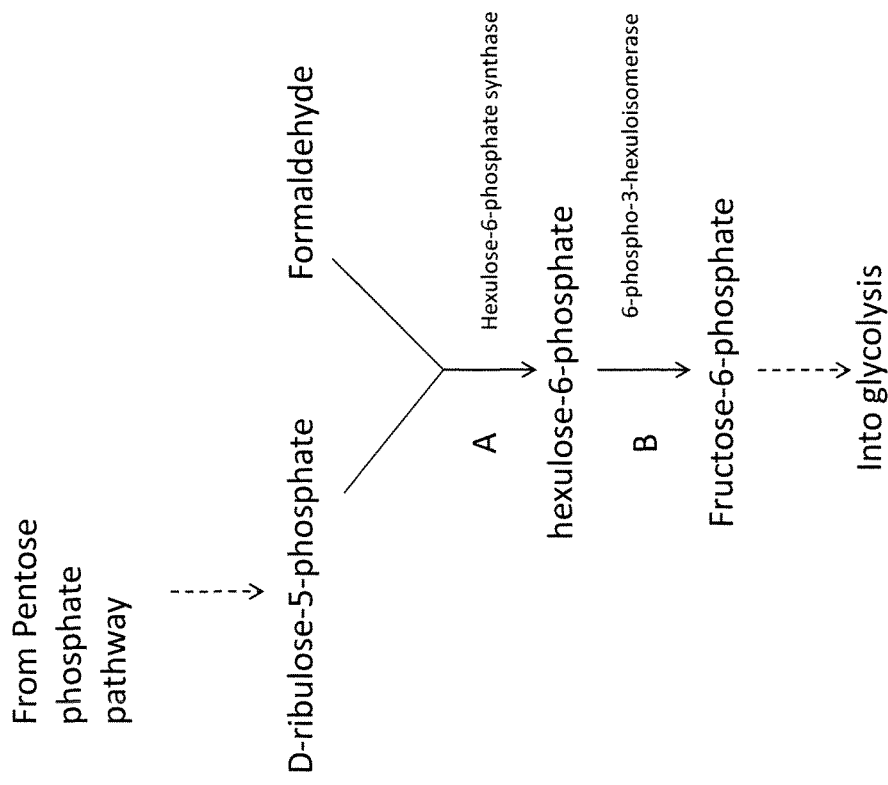
FIG. 3 shows an exemplary formaldehyde assimilation pathway. The enzymatic transformations are carried out by the following enzymes: 3A) a hexylose-6-phosphate synthase, and 3B) a 6-phospho-3-hexyloisomerase.
Figure 4:
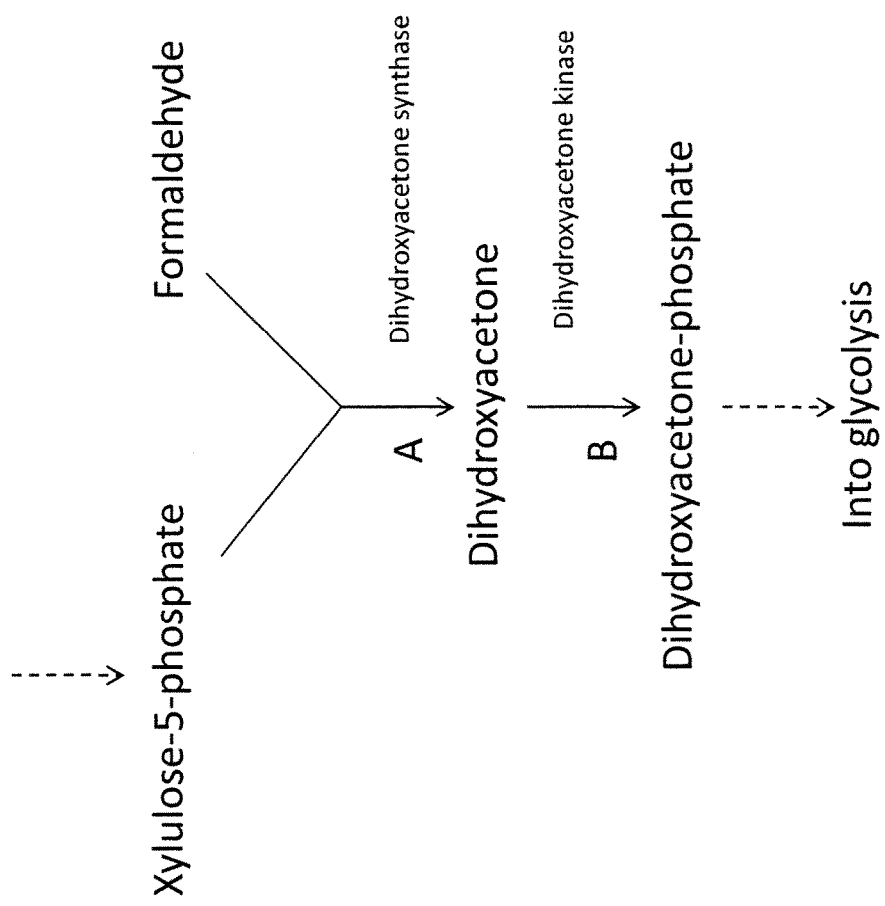
FIG. 4 shows an exemplary formaldehyde assimilation pathway. The enzymatic transformations are carried out by the following enzymes: 4A) a dihydroxyacetone synthase, and 4B) a dihydroxyacetone kinase.

Also provided herein are exemplary pathways, which utilize formaldehyde produced from the oxidation of methanol (e.g., as provided in FIG. 1, step J) in the formation of intermediates of certain central metabolic pathways that can be used for the formation of biomass. One exemplary formaldehyde assimilation pathway that can utilize formaldehyde produced from the oxidation of methanol (e.g., as provided in FIG. 1) is shown in FIG. 3, which involves condensation of formaldehyde and D-ribulose-5-phosphate to form hexylose-6-phosphate (h6p) by hexylose-6-phosphate synthase (FIG. 3, step A). The enzyme can use $Mg^{2+}$ or $Mn^{2+}$ for maximal activity, although other metal ions are useful, and even non-metal-ion-dependent mechanisms are contemplated. H6p is converted into fructose-6-phosphate by 6-phospho-3-hexyloisomerase (FIG. 3, step B). Another exemplary pathway that involves the detoxification and assimilation of formaldehyde produced from the oxidation of methanol (e.g., as provided in FIG. 1) is shown in FIG. 4 and proceeds through dihydroxyacetone. Dihydroxyacetone synthase is a special transketolase that first transfers a glycoaldehyde group from xylulose-5-phosphate to formaldehyde, resulting in the formation of dihydroxyacetone (DHA) and glyceraldehyde-3-phosphate (G3P), which is an intermediate in glycolysis (FIG. 4, step A). The DHA obtained from DHA synthase is then further phosphorylated to form DHA phosphate by a DHA kinase (FIG. 4, step B). DHAP can be assimilated into glycolysis and several other pathways. Rather than converting formaldehyde to formate and on to $CO_2$ off-gassed, the pathways provided in FIGS. 3 and 4 show that carbon is assimilated, going into the final product.

Thus, in one embodiment, an organism having a methanol metabolic pathway, either alone or in combination with a succinate pathway, as provided herein, further comprises a formaldehyde assimilation pathway that utilizes formaldehyde, e.g., obtained from the oxidation of methanol, in the formation of intermediates of certain central metabolic pathways that can be used, for example, in the formation of biomass. In some of embodiments, the formaldehyde assimilation pathway comprises 3A or 3B, wherein 3A is a hexylose-6-phosphate synthase and 3B is a 6-phospho-3-hexyloisomerase In other embodiments, the formaldehyde assimilation pathway comprises 4A or 4B, wherein 4A is a dihydroxyacetone synthase and 4B is a dihydroxyacetone kinase.

In certain embodiments, provided herein is a non-naturally occurring microbial organism having a methanol metabolic pathway, wherein said organism comprises at least one exogenous nucleic acid encoding a methanol dehydrogenase (1J) expressed in a sufficient amount to enhance the availability of reducing equivalents in the presence of methanol and/or expressed in a sufficient amount to convert methanol to formaldehyde. In some embodiments, the microbial organism further comprises a formaldehyde assimilation pathway. In certain embodiments, the organism further comprises at least one exogenous nucleic acid encoding a formaldehyde assimilation pathway enzyme expressed in a sufficient amount to produce an intermediate of glycolysis and/or a metabolic pathway that can be used, for example, in the formation of biomass. In certain embodiments, the formaldehyde assimilation pathway enzyme is selected from the group consisting of a hexylose-6-phosphate synthase (3A), 6-phospho-3-hexyloisomerase (3B), dihydroxyacetone synthase (4A) and dihydroxyacetone kinase (4B).

In one aspect, provided herein is a non-naturally occurring microbial organism, comprising (1) a methanol metabolic pathway, wherein said organism comprises at least one exogenous nucleic acid encoding a methanol metabolic pathway enzyme in a sufficient amount to enhance the availability of reducing equivalents in the presence of methanol and/or expressed in a sufficient amount to convert methanol to formaldehyde; and (2) a formaldehyde assimilation pathway, wherein said organism comprises at least one exogenous nucleic acid encoding a formaldehyde assimilation pathway enzyme expressed in a sufficient amount to produce an intermediate of glycolysis and/or a metabolic pathway that can be used, for example, in the formation of biomass. In specific embodiments, the methanol metabolic pathway comprises a methanol dehydrogenase (1J). In certain embodiments, the formaldehyde assimilation pathway enzyme is 3A, and the intermediate is a hexylose-6-phosphate, a fructose-6-phosphate, or a combination thereof. In other embodiments, the formaldehyde assimilation pathway enzyme is 3B, and the intermediate is a hexylose-6-phosphate, a fructose-6-phosphate, or a combination thereof. In yet other embodiments, the formaldehyde assimilation pathway enzyme is 3A and 3B, and the intermediate is a hexylose-6-phosphate, a fructose-6-phosphate, or a combination thereof. In some embodiments, the formaldehyde assimilation pathway enzyme is 4A, and the intermediate is a dihydroxyacetone (DHA), a dihydroxyacetone phosphate, or a combination thereof. In other embodiments, the formaldehyde assimilation pathway enzyme is 4B, and the intermediate is a DHA, a dihydroxyacetone phosphate, or a combination thereof. In yet other embodiments, the formaldehyde assimilation pathway enzyme is 4A and 4B, and the intermediate is a DHA, a dihydroxyacetone phosphate, or a combination thereof. In one embodiment, the at least one exogenous nucleic acid encoding the methanol metabolic pathway enzyme, in the presence of methanol, sufficiently enhances the availability of reducing equivalents and sufficiently increases formaldehyde assimilation to increase the production of succinate or other products described herein by the non-naturally microbial organism. In some embodiments, the methanol metabolic pathway comprises any of the various combinations of methanol metabolic pathway enzymes described above or elsewhere herein.

In certain embodiments, (1) the methanol metabolic pathway comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is a methanol methyltransferase; 1B is a methylenetetrahydrofolate reductase; 1C is a methylenetetrahydrofolate dehydrogenase; 1D is a methenyltetrahydrofolate cyclohydrolase; 1E is a formyltetrahydrofolate deformylase; 1F is a formyltetrahydrofolate synthetase; 1G is a formate hydrogen lyase; 1H is a hydrogenase, 1I is a formate dehydrogenase; 1J is a methanol dehydrogenase; 1K is spontaneous or formaldehyde activating enzyme; 1L is a formaldehyde dehydrogenase; 1M is spontaneous or a S-(hydroxymethyl)glutathione synthase; 1N is glutathione-dependent formaldehyde dehydrogenase and 1O is S-formylglutathione hydrolase; and (2) the formaldehyde assimilation pathway comprises 3A, 3B or a combination thereof, wherein 3A is a hexylose-6-phosphate synthase, and 3B is a 6-phospho-3-hexyloisomerase. In some embodiments, 1K is spontaneous. In other embodiments, 1K is a formaldehyde activating enzyme. In some embodiments, 1M is spontaneous. In other embodiments, 1M is a S-(hydroxymethyl)glutathione synthase. In some embodiments, the intermediate is a hexylose-6-phosphate. In other embodiments, the intermediate is a fructose-6-phosphate. In yet other embodiments, the intermediate is a hexylose-6-phosphate and a fructose-6-phosphate.

In one embodiment, the formaldehyde assimilation pathway comprises 3A. In another embodiment, the formaldehyde assimilation pathway comprises 3B. In one embodiment, the formaldehyde assimilation pathway comprises 3A and 3B.

In some embodiments, the methanol metabolic pathway is a methanol metabolic pathway depicted in FIG. 1, and a formaldehyde assimilation pathway depicted in FIG. 3. An exemplary set of formaldehyde assimilation pathway enzymes to convert D-ribulose-5-phosphate and formaldehyde to fructose-6-phosphate (via hexylose-6-phosphate) according to FIG. 3 include 3A and 3B.

In a specific embodiment, (1) the methanol metabolic pathway comprises 1J; and (2) the formaldehyde assimilation pathway comprises 3A and 3B. In other embodiments, (1) the methanol metabolic pathway comprises 1J and 1K; and (2) the formaldehyde assimilation pathway comprises 3A and 3B. In some embodiments, (1) the methanol metabolic pathway comprises 1J, 1C, 1D and 1E; and (2) the formaldehyde assimilation pathway comprises 3A and 3B. In one embodiment, (1) the methanol metabolic pathway comprises 1J, 1C, 1D and 1F; and (2) the formaldehyde assimilation pathway comprises 3A and 3B. In another embodiment, (1) the methanol metabolic pathway comprises 1J and 1L; and (2) the formaldehyde assimilation pathway comprises 3A and 3B. In yet another embodiment, (1) the methanol metabolic pathway comprises 1J, 1M, 1N and 1O; and (2) the formaldehyde assimilation pathway comprises 3A and 3B. In certain embodiments, (1) the methanol metabolic pathway comprises 1J, 1N and 1O; and (2) the formaldehyde assimilation pathway comprises 3A and 3B. In some embodiments, (1) the methanol metabolic pathway comprises 1J, 1K, 1C, 1D and 1E; and (2) the formaldehyde assimilation pathway comprises 3A and 3B. In one embodiment, (1) the methanol metabolic pathway comprises 1J, 1K, 1C, 1D and 1F; and (2) the formaldehyde assimilation pathway comprises 3A and 3B. In some embodiments, (1) the methanol metabolic pathway comprises 1J, 1C, 1D, 1E and 1I; and (2) the formaldehyde assimilation pathway comprises 3A and 3B. In one embodiment, (1) the methanol metabolic pathway comprises 1J, 1C, 1D, 1F and 1I; and (2) the formaldehyde assimilation pathway comprises 3A and 3B. In another embodiment, (1) the methanol metabolic pathway comprises 1J, 1L and 1I; and (2) the formaldehyde assimilation pathway comprises 3A and 3B. In yet another embodiment, (1) the methanol metabolic pathway comprises 1J, 1M, 1N, 1O and 1I; and (2) the formaldehyde assimilation pathway comprises 3A and 3B. In certain embodiments, (1) the methanol metabolic pathway comprises 1J, 1N, 1O and 1I; and (2) the formaldehyde assimilation pathway comprises 3A and 3B. In some embodiments, (1) the methanol metabolic pathway comprises 1J, 1K, 1C, 1D, 1E and 1I; and (2) the formaldehyde assimilation pathway comprises 3A and 3B. In one embodiment, (1) the methanol metabolic pathway comprises 1J, 1K, 1C, 1D, 1F and 1I; and (2) the formaldehyde assimilation pathway comprises 3A and 3B. In some embodiments, (1) the methanol metabolic pathway comprises 1J, 1C, 1D, 1E and 1G; and (2) the formaldehyde assimilation pathway comprises 3A and 3B. In one embodiment, (1) the methanol metabolic pathway comprises 1J, 1C, 1D, 1F and 1G; and (2) the formaldehyde assimilation pathway comprises 3A and 3B. In another embodiment, (1) the methanol metabolic pathway comprises 1J, 1L and 1G; and (2) the formaldehyde assimilation pathway comprises 3A and 3B. In yet another embodiment, (1) the methanol metabolic pathway comprises 1J, 1M, 1N, 1O and 1G; and (2) the formaldehyde assimilation pathway comprises 3A and 3B. In certain embodiments, (1) the methanol metabolic pathway comprises 1J, 1N, 1O and 1G; and (2) the formaldehyde assimilation pathway comprises 3A and 3B. In some embodiments, (1) the methanol metabolic pathway comprises 1J, 1K, 1C, 1D, 1E and 1G; and (2) the formaldehyde assimilation pathway comprises 3A and 3B. In one embodiment, (1) the methanol metabolic pathway comprises 1J, 1K, 1C, 1D, 1F and 1G; and (2) the formaldehyde assimilation pathway comprises 3A and 3B. In some embodiments, (1) the methanol metabolic pathway comprises 1J, 1C, 1D, 1E, 1G and 1H; and (2) the formaldehyde assimilation pathway comprises 3A and 3B. In one embodiment, (1) the methanol metabolic pathway comprises 1J, 1C, 1D, 1F, 1G and 1H; and (2) the formaldehyde assimilation pathway comprises 3A and 3B. In another embodiment, (1) the methanol metabolic pathway comprises 1J, 1L, 1G and 1H; and (2) the formaldehyde assimilation pathway comprises 3A and 3B. In yet another embodiment, (1) the methanol metabolic pathway comprises 1J, 1M, 1N, 1O, 1G and 1H; and (2) the formaldehyde assimilation pathway comprises 3A and 3B. In certain embodiments, (1) the methanol metabolic pathway comprises 1J, 1N, 1O, 1G and 1H; and (2) the formaldehyde assimilation pathway comprises 3A and 3B. In some embodiments, (1) the methanol metabolic pathway comprises 1J, 1K, 1C, 1D, 1E, 1G and 1H; and (2) the formaldehyde assimilation pathway comprises 3A and 3B. In one embodiment, (1) the methanol metabolic pathway comprises 1J, 1K, 1C, 1D, 1F, 1G and 1H; and (2) the formaldehyde assimilation pathway comprises 3A and 3B. In some embodiments, 1K is spontaneous. In other embodiments, 1K is a formaldehyde activating enzyme. In some embodiments, 1M is spontaneous. In some embodiments, the intermediate is a hexylose-6-phosphate. In other embodiments, the intermediate is a fructose-6-phosphate. In yet other embodiments, the intermediate is a hexylose-6-phosphate and a fructose-6-phosphate.

In certain embodiments, (1) the methanol metabolic pathway comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is a methanol methyltransferase; 1B is a methylenetetrahydrofolate reductase; 1C is a methylenetetrahydrofolate dehydrogenase; 1D is a methenyltetrahydrofolate cyclohydrolase; 1E is a formyltetrahydrofolate deformylase; 1F is a formyltetrahydrofolate synthetase; 1G is a formate hydrogen lyase; 1H is a hydrogenase, 1I is a formate dehydrogenase; 1J is a methanol dehydrogenase; 1K is spontaneous or formaldehyde activating enzyme; 1L is a formaldehyde dehydrogenase; 1M is spontaneous or a S-(hydroxymethyl)glutathione synthase; 1N is glutathione-dependent formaldehyde dehydrogenase and 1O is S-formylglutathione hydrolase; and (2) the formaldehyde assimilation pathway comprises 4A, 4B or a combination thereof, wherein 4A is a dihydroxyacetone synthase and 4B is a dihydroxyacetone kinase. In some embodiments, 1K is spontaneous. In other embodiments, 1K is a formaldehyde activating enzyme. In some embodiments, 1M is spontaneous. In other embodiments, 1M is a S-(hydroxymethyl) glutathione synthase. In some embodiments, the intermediate is a DHA. In other embodiments, the intermediate is a dihydroxyacetone phosphate. In yet other embodiments, the intermediate is a DHA and a dihydroxyacetone phosphate.

In one embodiment, the formaldehyde assimilation pathway comprises 4A. In another embodiment, the formaldehyde assimilation pathway comprises 4B. In one embodiment, the formaldehyde assimilation pathway comprises 4A and 4B.

In some embodiments, the methanol metabolic pathway is a methanol metabolic pathway depicted in FIG. 1, and a formaldehyde assimilation pathway depicted in FIG. 4. An exemplary set of formaldehyde assimilation pathway enzymes to convert xyulose-5-phosphate and formaldehyde to dihydroxyacetone-phosphate (via DHA) according to FIG. 4 include 4A and 4B.

In a specific embodiment, (1) the methanol metabolic pathway comprises 1J; and (2) the formaldehyde assimilation pathway comprises 4A and 4B. In other embodiments, (1) the methanol metabolic pathway comprises 1J and 1K; and (2) the formaldehyde assimilation pathway comprises 4A and 4B. In some embodiments, (1) the methanol metabolic pathway comprises 1J, 1C, 1D and 1E; and (2) the formaldehyde assimilation pathway comprises 4A and 4B. In one embodiment, (1) the methanol metabolic pathway comprises 1J, 1C, 1D and 1F; and (2) the formaldehyde assimilation pathway comprises 4A and 4B. In another embodiment, (1) the methanol metabolic pathway comprises 1J and 1L; and (2) the formaldehyde assimilation pathway comprises 4A and 4B. In yet another embodiment, (1) the methanol metabolic pathway comprises 1J, 1M, 1N and 1O; and (2) the formaldehyde assimilation pathway comprises 4A and 4B. In certain embodiments, (1) the methanol metabolic pathway comprises 1J, 1N and 1O; and (2) the formaldehyde assimilation pathway comprises 4A and 4B. In some embodiments, (1) the methanol metabolic pathway comprises 1J, 1K, 1C, 1D and 1E; and (2) the formaldehyde assimilation pathway comprises 4A and 4B. In one embodiment, (1) the methanol metabolic pathway comprises 1J, 1K, 1C, 1D and 1F; and (2) the formaldehyde assimilation pathway comprises 4A and 4B. In some embodiments, (1) the methanol metabolic pathway comprises 1J, 1C, 1D, 1E and 1I; and (2) the formaldehyde assimilation pathway comprises 4A and 4B. In one embodiment, (1) the methanol metabolic pathway comprises 1J, 1C, 1D, 1F and 1I; and (2) the formaldehyde assimilation pathway comprises 4A and 4B. In another embodiment, (1) the methanol metabolic pathway comprises 1J, 1L and 1I; and (2) the formaldehyde assimilation pathway comprises 4A and 4B. In yet another embodiment, (1) the methanol metabolic pathway comprises 1J, 1M, 1N, 1O and 1I; and (2) the formaldehyde assimilation pathway comprises 4A and 4B. In certain embodiments, (1) the methanol metabolic pathway comprises 1J, 1N, 1O and 1I; and (2) the formaldehyde assimilation pathway comprises 4A and 4B. In some embodiments, (1) the methanol metabolic pathway comprises 1J, 1K, 1C, 1D, 1E and 1I; and (2) the formaldehyde assimilation pathway comprises 4A and 4B. In one embodiment, (1) the methanol metabolic pathway comprises 1J, 1K, 1C, 1D, 1F and 1I; and (2) the formaldehyde assimilation pathway comprises 4A and 4B. In some embodiments, (1) the methanol metabolic pathway comprises 1J, 1C, 1D, 1E and 1G; and (2) the formaldehyde assimilation pathway comprises 4A and 4B. In one embodiment, (1) the methanol metabolic pathway comprises 1J, 1C, 1D, 1F and 1G; and (2) the formaldehyde assimilation pathway comprises 4A and 4B. In another embodiment, (1) the methanol metabolic pathway comprises 1J, 1L and 1G; and (2) the formaldehyde assimilation pathway comprises 4A and 4B. In yet another embodiment, (1) the methanol metabolic pathway comprises 1J, 1M, 1N, 1O and 1G; and (2) the formaldehyde assimilation pathway comprises 4A and 4B. In certain embodiments, (1) the methanol metabolic pathway comprises 1J, 1N, 1O and 1G; and (2) the formaldehyde assimilation pathway comprises 4A and 4B. In some embodiments, (1) the methanol metabolic pathway comprises 1J, 1K, 1C, 1D, 1E and 1G; and (2) the formaldehyde assimilation pathway comprises 4A and 4B. In one embodiment, (1) the methanol metabolic pathway comprises 1J, 1K, 1C, 1D, 1F and 1G; and (2) the formaldehyde assimilation pathway comprises 4A and 4B. In some embodiments, (1) the methanol metabolic pathway comprises 1J, 1C, 1D, 1E, 1G and 1H; and (2) the formaldehyde assimilation pathway comprises 4A and 4B. In one embodiment, (1) the methanol metabolic pathway comprises 1J, 1C, 1D, 1F, 1G and 1H; and (2) the formaldehyde assimilation pathway comprises 4A and 4B. In another embodiment, (1) the methanol metabolic pathway comprises 1J, 1L, 1G and 1H; and (2) the formaldehyde assimilation pathway comprises 4A and 4B. In yet another embodiment, (1) the methanol metabolic pathway comprises 1J, 1M, 1N, 1O, 1G and 1H; and (2) the formaldehyde assimilation pathway comprises 4A and 4B. In certain embodiments, (1) the methanol metabolic pathway comprises 1J, 1N, 1O, 1G and 1H; and (2) the formaldehyde assimilation pathway comprises 4A and 4B. In some embodiments, (1) the methanol metabolic pathway comprises 1J, 1K, 1C, 1D, 1E, 1G and 1H; and (2) the formaldehyde assimilation pathway comprises 4A and 4B. In one embodiment, (1) the methanol metabolic pathway comprises 1J, 1K, 1C, 1D, 1F, 1G and 1H; and (2) the formaldehyde assimilation pathway comprises 4A and 4B. In some embodiments, 1K is spontaneous. In other embodiments, 1K is a formaldehyde activating enzyme. In some embodiments, 1M is spontaneous. In some embodiments, the intermediate is a DHA. In other embodiments, the intermediate is a dihydroxyacetone phosphate. In yet other embodiments, the intermediate is a DHA and a dihydroxyacetone phosphate.

Any methanol metabolic pathway provided herein can be combined with any formaldehyde assimilation pathway provided herein. In addition, any methanol metabolic pathway provided herein can be combined with any succinate pathway and any formaldehyde pathway provided herein.

Also provided herein are methods of producing formaldehyde comprising culturing a non-naturally occurring microbial organism having a methanol metabolic pathway provided herein. In some embodiments, the methanol metabolic pathway comprises 1J. In certain embodiments, the organism is cultured in a substantially anaerobic culture medium. In specific embodiments, the formaldehyde is an intermediate that is consumed (assimilated) in the production of succinate and other products described herein.

Also provided herein are methods of producing an intermediate of glycolysis and/or a metabolic pathway that can be used, for example, in the formation of biomass, comprising culturing a non-naturally occurring microbial organism having a methanol metabolic pathway and a formaldehyde assimilation pathway, as provided herein, under conditions and for a sufficient period of time to produce the intermediate. In some embodiments, the intermediate is a hexylose-6-phosphate. In other embodiments, the intermediate is a fructose-6-phosphate. In yet other embodiments, the intermediate is a hexylose-6-phosphate and a fructose-6-phosphate. In some embodiments, the intermediate is a DHA. In other embodiments, the intermediate is a dihydroxyacetone phosphate. In yet other embodiments, the intermediate is a DHA and a dihydroxyacetone phosphate. In some embodiments, the methanol metabolic pathway comprises 1J. In certain embodiments, the organism is cultured in a substantially anaerobic culture medium. Such biomass can also be used in methods of producing any of the products, such as the biobased products, provided elsewhere herein.

In certain embodiments, the organism comprises two, three, four or five nucleic acids, each encoding a succinate pathway enzyme. In some embodiments, the organism comprises two nucleic acids, each encoding a succinate pathway enzyme. In some embodiments, the organism comprises three nucleic acids, each encoding a succinate pathway enzyme. In some embodiments, the organism comprises four nucleic acids, each encoding a succinate pathway enzyme. In other embodiments, the organism comprises five nucleic acids, each encoding a succinate pathway enzyme. In some embodiments, the nucleic acid encoding a succinate pathway enzyme is an exogenous nucleic acid. In other embodiments, the nucleic acid encoding an succinate pathway enzyme is an endogenous nucleic acid. In certain embodiments, the organism comprises two, three, four, five, six or seven nucleic acids, each encoding a succinate pathway enzyme; and the organism further comprises two, three, four, five, six or seven exogenous nucleic acids, each encoding a methanol metabolic pathway enzyme. In certain embodiments, the organism further comprises two exogenous nucleic acids, each encoding a methanol metabolic pathway enzyme. In certain embodiments, the organism further comprises three exogenous nucleic acids, each encoding a methanol metabolic pathway enzyme. In certain embodiments, the organism comprises further four exogenous nucleic acids, each encoding a methanol metabolic pathway enzyme. In certain embodiments, the organism further comprises five exogenous nucleic acids, each encoding a methanol metabolic pathway enzyme. In certain embodiments, the organism further comprises six exogenous nucleic acids, each encoding a methanol metabolic pathway enzyme. In certain embodiments, the organism further comprises seven exogenous nucleic acids, each encoding a methanol metabolic pathway enzyme.

In some embodiments, the organism comprises two or more exogenous nucleic acids, each encoding a formaldehyde assimilation pathway enzyme. In some embodiments, the organism comprises two exogenous nucleic acids, each encoding a formaldehyde assimilation pathway enzyme. In certain embodiments, the organism comprises two exogenous nucleic acids, each encoding a formaldehyde assimilation pathway enzyme; and the organism further comprises two, three, four, five, six or seven exogenous nucleic acids, each encoding a methanol metabolic pathway enzyme. In certain embodiments, the organism further comprises two exogenous nucleic acids, each encoding a methanol metabolic pathway enzyme. In certain embodiments, the organism further comprises three exogenous nucleic acids, each encoding a methanol metabolic pathway enzyme. In certain embodiments, the organism comprises further four exogenous nucleic acids, each encoding a methanol metabolic pathway enzyme. In certain embodiments, the organism further comprises five exogenous nucleic acids, each encoding a methanol metabolic pathway enzyme. In certain embodiments, the organism further comprises six exogenous nucleic acids, each encoding a methanol metabolic pathway enzyme. In certain embodiments, the organism further comprises seven exogenous nucleic acids, each encoding a methanol metabolic pathway enzyme.

In some embodiments, the at least one exogenous nucleic acid encoding a methanol metabolic pathway enzyme is a heterologous nucleic acid. In other embodiments, the at least one exogenous nucleic acid encoding a formaldehyde assimilation pathway enzyme is a heterologous nucleic acid. In other embodiments, the at least one nucleic acid encoding a succinate pathway enzyme is a heterologous nucleic acid. In certain embodiments, the at least one exogenous nucleic acid encoding a methanol metabolic pathway enzyme is a heterologous nucleic acid, and the at least one nucleic acid encoding a succinate pathway enzyme is a heterologous nucleic acid. In other embodiments, the at least one exogenous nucleic acid encoding a methanol metabolic pathway enzyme is a heterologous nucleic acid, and the at least one exogenous nucleic acid encoding a formaldehyde assimilation pathway enzyme is a heterologous nucleic acid.

In certain embodiments, the organism is in a substantially anaerobic culture medium.

It is understood that any of the pathways disclosed herein, as described in the Examples and exemplified in the figures, including the pathways of FIGS. 1, 2, 3 and 4, can be utilized to generate a non-naturally occurring microbial organism that produces any pathway intermediate or product, as desired. A non-limiting example of such an intermediate or product is succinate. As disclosed herein, such a microbial organism that produces an intermediate can be used in combination with another microbial organism expressing downstream pathway enzymes to produce a desired product. However, it is understood that a non-naturally occurring eukaryotic organism that produces a succinate pathway intermediate can be utilized to produce the intermediate as a desired product.

In certain embodiments, a non-naturally occurring microbial organism comprising a methanol metabolic pathway and a succinate pathway provided herein, further comprises one or more gene disruptions. In certain embodiments, the one or more gene disruptions confer increased production of succinate in the organism. In other embodiments, a non-naturally occurring microbial organism comprising a methanol metabolic pathway and a formaldehyde assimilation pathway provided herein, further comprises one or more gene disruptions. In some embodiments, the gene disruption is in an endogenous gene encoding a protein and/or enzyme involved in native production of ethanol, glycerol, acetate, lactate, formate, $CO_2$, amino acids, or any combination thereof, by said microbial organism. In one embodiment, the gene disruption is in an endogenous gene encoding a protein and/or enzyme involved in native production of ethanol. In another embodiment, the gene disruption is in an endogenous gene encoding a protein and/or enzyme involved in native production of glycerol. In other embodiments, the gene disruption is in an endogenous gene encoding a protein and/or enzyme involved in native production of acetate. In another embodiment, the gene disruption is in an endogenous gene encoding a protein and/or enzyme involved in native production of lactate. In one embodiment, the gene disruption is in an endogenous gene encoding a protein and/or enzyme involved in native production of formate. In another embodiment, the gene disruption is in an endogenous gene encoding a protein and/or enzyme involved in native production of $CO_2$. In other embodiments, the gene disruption is in an endogenous gene encoding a protein and/or enzyme involved in native production of amino acids by said microbial organism. The protein or enzyme is a pyruvate decarboxylase, an ethanol dehydrogenase, a glycerol dehydrogenase, a glycerol-3-phosphatase, a glycerol-3-phosphate dehydrogenase, a lactate dehydrogenase, an acetate kinase, a phosphotransacetylase, a pyruvate oxidase, a pyruvate:quinone oxidoreductase, a pyruvate formate lyase, an alcohol dehydrogenase, a lactate dehydrogenase, a pyruvate dehydrogenase, a pyruvate formate-lyase-2-ketobutyrate formate-lyase, a pyruvate transporter, a monocarboxylate transporter, a NADH dehydrogenase, a cytochrome oxidase, a pyruvate kinase, or any combination thereof. Non-limiting exemplary genes encoding these proteins or enzymes are provided in Example IV below. In certain embodiments, the organism comprises from one to twenty-five gene disruptions. In other embodiments, the organism comprises from one to twenty gene disruptions. In some embodiments, the organism comprises from one to fifteen gene disrutions. In other embodiments, the organism comprises from one to ten gene disruptions. In some embodiments, the organism comprises from one to five gene disruptions. In certain embodiments, the organism comprises 1, 2, 3, 4, 5, 6, 7, 8, 9, 10, 11, 12, 13, 14, 15, 16, 17, 18, 19, 20, 21, 22, 23, 24 or 25 gene disruptions or more.

In other embodiments, a non-naturally occurring microbial organism comprising a methanol metabolic pathway and a succinate pathway provided herein, further comprises one or more endogenous proteins or enzymes involved in native production of ethanol, glycerol, acetate, lactate, formate, $CO_2$ and/or amino acids by said microbial organism, wherein said one or more endogenous proteins or enzymes has attenuated protein or enzyme activity and/or expression levels. In some embodiments, a non-naturally occurring microbial organism comprising a methanol metabolic pathway and a formaldehyde assimilation pathway provided herein, further comprises one or more endogenous proteins or enzymes involved in native production of ethanol, glycerol, acetate, lactate, formate, CO2 and/or amino acids by said microbial organism, wherein said one or more endogenous proteins or enzymes has attenuated protein or enzyme activity and/or expression levels. In one embodiment the endogenous protein or enzyme is a pyruvate decarboxylase, an ethanol dehydrogenase, a glycerol dehydrogenase, a glycerol-3-phosphatase, a glycerol-3-phosphate dehydrogenase, a lactate dehydrogenase, an acetate kinase, a phosphotransacetylase, a pyruvate oxidase, a pyruvate:quinone oxidoreductase, a pyruvate formate lyase, an alcohol dehydrogenase, a lactate dehydrogenase, a pyruvate dehydrogenase, a pyruvate formate-lyase-2-ketobutyrate formate-lyase, a pyruvate transporter, a monocarboxylate transporter, a NADH dehydrogenase, a cytochrome oxidase, a pyruvate kinase, or any combination thereof. Non-limiting exemplary genes encoding these proteins or enzymes are provided in Example IV below.

Each of the non-naturally occurring alterations provided herein (see, e.g., Example IV) result in increased production and an enhanced level of succinate, for example, during the exponential growth phase of the microbial organism, compared to a strain that does not contain such metabolic alterations, under appropriate culture conditions. Appropriate conditions include, for example, those disclosed herein, including conditions such as particular carbon sources or reactant availabilities and/or adaptive evolution.

Given the teachings and guidance provided herein (see, e.g., Example IV), those skilled in the art will understand that to introduce a metabolic alteration, such as attenuation of an enzyme, it can be necessary to disrupt the catalytic activity of the one or more enzymes involved in the reaction. Alternatively, a metabolic alteration can include disrupting expression of a regulatory protein or cofactor necessary for enzyme activity or maximal activity. Furthermore, genetic loss of a cofactor necessary for an enzymatic reaction can also have the same effect as a disruption of the gene encoding the enzyme. Disruption can occur by a variety of methods including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity, disruption can occur by a genetic alteration that reduces or eliminates the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits required to form an active complex, by destruction of the catalytic subunit of the multimeric complex or by both. Other functions of multimeric protein association and activity also can be targeted in order to disrupt a metabolic reaction of the invention. Such other functions are well known to those skilled in the art. Similarly, a target enzyme activity can be reduced or eliminated by disrupting expression of a protein or enzyme that modifies and/or activates the target enzyme, for example, a molecule required to convert an apoenzyme to a holoenzyme. Further, some or all of the functions of a single polypeptide or multimeric complex can be disrupted according to the invention in order to reduce or abolish the catalytic activity of one or more enzymes involved in a reaction or metabolic modification of the invention. Similarly, some or all of enzymes involved in a reaction or metabolic modification of the invention can be disrupted so long as the targeted reaction is reduced or eliminated.

Given the teachings and guidance provided herein (see, e.g., Example IV), those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding a enzyme of a targeted metabolic reaction can be practiced in the methods of the invention and incorporated into the non-naturally occurring microbial organisms of the invention in order to achieve the increased production of fatty alcohol, fatty aldehyde or fatty acid or growth-coupled product production.

Given the teachings and guidance provided herein (see, e.g., Example IV), those skilled in the art also will understand that enzymatic activity or expression can be attenuated using well known methods. Reduction of the activity or amount of an enzyme can mimic complete disruption if the reduction causes activity of the enzyme to fall below a critical level that is normally required for the pathway to function. Reduction of enzymatic activity by various techniques rather than disruption can be important for an organism's viability. Methods of reducing enzymatic activity that result in similar or identical effects of a gene disruption include, but are not limited to: reducing gene transcription or translation; destabilizing mRNA, protein or catalytic RNA; and mutating a gene that affects enzyme kinetics. Natural or imposed regulatory controls can also accomplish enzyme attenuation including: promoter replacement; loss or alteration of transcription factors; introduction of inhibitory RNAs or peptides such as siRNA, antisense RNA, RNA or peptide/small-molecule binding aptamers, ribozymes, aptazymes and riboswitches; and addition of drugs and other chemicals that reduce or disrupt enzymatic activity such as gene splicing.

One of ordinary skill in the art will also recognize that attenuation of an enzyme (e.g., as provided in Example IV) can be done at various levels. For example, at the gene level, mutations causing a partial or complete null phenotype or epistatic genetic effects that mask the activity of a gene product can be used to attenuate an enzyme. At the gene expression level, methods for attenuation include: coupling transcription to an endogenous or exogenous inducer such as IPTG, then adding low or 0 levels of inducer during the production phase; introducing or modifying positive or negative regulators; modify histone acetylation/deacetylation in region where gene is integrated; introducing a transposition to disrupt a promoter or a regulatory gene; flipping of a transposable element or promoter region; deleting one allele resulting in loss of heterozygosity in a diploid organism; introducing nucleic acids that increase RNA degradation; or in bacteria, for example, introduction of a tmRNA tag, which can lead to RNA degradation and ribosomal stalling. At the translational level, attenuation can include: introducing rare codons to limit translation; introducing RNA interference molecules that block translation; modifying regions outside the coding sequence, such as introducing secondary structure into UTR regions to block translation or reduce efficiency of translation; adding RNAase sites for rapid transcript degradation; introducing antisense RNA oligomers or antisense transcripts; introducing RNA or peptide aptamers, ribozymes, aptazymes, riboswitches; or introducing translational regulatory elements involving RNA structure that can prevent or reduce translation that can be controlled by the presence or absence of small molecules. At the level of enzyme localization and/or longevity, enzyme attenuation can include: adding a degradation tag for faster protein turnover; or adding a localization tag that results in the enzyme being localized to a compartment where it would not be able to react normally. At the level of post-translational regulation, enzyme attenuation can include: increasing intracellular concentration of known inhibitors; or modifying post-translational modified sites. At the level of enzyme activity, enzyme attenuation can include: adding endogenous or exogenous inhibitor, such as a target-specific drug, to reduce enzyme activity; limiting availability of essential cofactors, such as B12, for an enzyme that require it; chelating a metal ion that is required for activity; or introducing a dominant negative mutation.

In some embodiments, microaerobic designs can be used based on the growth-coupled formation of the desired product. To examine this, production cones can be constructed for each strategy by first maximizing and, subsequently minimizing the product yields at different rates of biomass formation feasible in the network. If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the product in the calculated range, including the lowest amount at the bottommost point of the vertical line. Such designs are given a low priority.

The succinate-production strategies identified in the various tables disclosed herein (e.g., Example IV) can be disrupted to increase production of succinate. Accordingly, also provided herein is a non-naturally occurring microbial organism having metabolic modifications coupling succinate production to growth of the organism, where the metabolic modifications includes disruption of one or more genes selected from the genes encoding proteins and/or enzymes shown in the various tables disclosed herein.

Each of the strains can be supplemented with additional deletions if it is determined that the strain designs do not sufficiently increase the production of succinate and/or couple the formation of the product with biomass formation. Alternatively, some other enzymes not known to possess significant activity under the growth conditions can become active due to adaptive evolution or random mutagenesis. Such activities can also be knocked out. However, the list of gene deletion disclosed herein allows the construction of strains exhibiting high-yield production of succinate, including growth-coupled production of succinate.

In another aspect, provided herein is a method for producing succinate, comprising culturing any one of the non-naturally occurring microbial organisms comprising a methanol metabolic pathway and a succinate pathway provided herein under conditions and for a sufficient period of time to produce succinate. In certain embodiments, the organism is cultured in a substantially anaerobic culture medium.

In one embodiment, provided herein are methods for producing succinate, comprising culturing an organism provided herein (e.g., a non-naturally occurring microbial organisms comprising a methanol metabolic pathway and a succinate pathway) under conditions and for a sufficient period of time to produce succinate. In some embodiments, the method comprises culturing, for a sufficient period of time to produce succinate, a non-naturally occurring microbial organism, comprising (1) a methanol metabolic pathway, wherein said organism comprises at least one exogenous nucleic acid encoding a methanol metabolic pathway enzyme in a sufficient amount to enhance the availability of reducing equivalents in the presence of methanol; and (2) a succinate pathway.

In certain embodiments of the methods provided herein, the organism further comprises at least one nucleic acid encoding a succinate pathway enzyme expressed in a sufficient amount to produce succinate. In some embodiments, the nucleic acid encoding a succinate pathway enzyme is an exogenous nucleic acid. In other embodiments, the nucleic acid encoding an succinate pathway enzyme is an endogenous nucleic acid. In some embodiments, the organism further comprises one or more gene disruptions provided herein that confer increased production of succinate in the organism. In certain embodiments, the one or more gene disruptions occurs in an endogenous gene encoding a protein or enzyme involved in native production of ethanol, glycerol, acetate, lactate, formate, $CO_2$ and/or amino acids by said microbial organism. In other embodiments, the organism further comprises one or more endogenous proteins or enzymes involved in native production of ethanol, glycerol, acetate, lactate, formate, $CO_2$ and/or amino acids by said microbial organism, wherein said one or more endogenous proteins or enzymes has attenuated protein or enzyme activity and/or expression levels. In certain embodiments, the organism is a Crabtree positive, eukaryotic organism, and the organism is cultured in a culture medium comprising glucose. In certain embodiments, the organism comprises from one to twenty-five gene disruptions. In other embodiments, the organism comprises from one to twenty gene disruptions. In some embodiments, the organism comprises from one to fifteen gene disrutions. In other embodiments, the organism comprises from one to ten gene disruptions. In some embodiments, the organism comprises from one to five gene disruptions. In certain embodiments, the organism comprises 1, 2, 3, 4, 5, 6, 7, 8, 9, 10, 11, 12, 13, 14, 15, 16, 17, 18, 19, 20, 21, 22, 23, 24 or 25 gene disruptions or more.

In an additional embodiment, the invention provides a non-naturally occurring microbial organism having a succinate pathway, formaldehyde assimilation pathway and/or methanol metabolic pathway, wherein the non-naturally occurring microbial organism comprises at least one exogenous nucleic acid encoding an enzyme or protein that converts a substrate to a product. By way of example, in FIG. 1, the substrate of 1J is methanol, and the product is formaldehyde; the substrate of 1L is formaldehyde, and the product is formate; and so forth. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, provided herein are non-naturally occurring microbial organisms containing at least one exogenous nucleic acid encoding an enzyme or protein, where the enzyme or protein converts the substrates and products of a methanol metabolic pathway, such as that shown in FIG. 1; a succinate pathway, such as that shown in FIG. 2; and/or a formaldehyde assimilation pathway, such as that shown in FIG. 3 or 4.

While generally described herein as a microbial organism that contains a succinate pathway, formaldehyde assimilation pathway, and/or a methanol metabolic pathway, it is understood that provided herein are also non-naturally occurring microbial organism comprising at least one nucleic acid encoding a succinate pathway, formaldehyde assimilation pathway, and/or a methanol metabolic pathway enzyme expressed in a sufficient amount to produce an intermediate of a succinate pathway, formaldehyde assimilation pathway, and/or a methanol metabolic pathway intermediate. For example, as disclosed herein, a succinate pathway is exemplified in FIG. 2. Therefore, in addition to a microbial organism containing a succinate pathway that produces succinate, also provided herein is a non-naturally occurring microbial organism comprising at least one nucleic acid encoding a succinate pathway enzyme, where the microbial organism produces a succinate pathway intermediate. In some embodiments, the nucleic acid encoding a succinate pathway enzyme is an exogenous nucleic acid. In other embodiments, the nucleic acid encoding an succinate pathway enzyme is an endogenous nucleic acid.

In some embodiments, the carbon feedstock and other cellular uptake sources such as phosphate, ammonia, sulfate, chloride and other halogens can be chosen to alter the isotopic distribution of the atoms present in succinate or any succinate pathway intermediate. The various carbon feedstock and other uptake sources enumerated above will be referred to herein, collectively, as "uptake sources." Uptake sources can provide isotopic enrichment for any atom present in the product succinate, and/or succinate pathway intermediate, or for side products generated in reactions diverging away from a succinate pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target isotopic ratio of an uptake source can be obtained by selecting a desired origin of the uptake source as found in nature For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

Isotopic enrichment is readily assessed by mass spectrometry using techniques known in the art such as Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC) and/or high performance liquid chromatography (HPLC).

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=–19 per mil (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=–19 per mil. This is equivalent to an absolute (AD 1950) $^{14}C/^{12}C$ ratio of 1.176±0.010×10$^{-12}$ (Karlen et al., *Arkiv Geofysik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is –17.8 per mille. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable BDO and renewable terephthalic acid resulted in bio-based content exceeding 90% (Colonna et al., supra, 2011).

Accordingly, in some embodiments, the present invention provides succinate, or a succinate pathway intermediate thereof, that has a carbon-12, carbon-13, and carbon-14 ratio that reflects an atmospheric carbon, also referred to as environmental carbon, uptake source. For example, in some aspects, the succinate, or a succinate intermediate thereof can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides succinate, or a succinate intermediate thereof, that has a carbon-12, carbon-13, and carbon-14 ratio that reflects petroleum-based carbon uptake source. In this aspect, the a succinate, or a succinate intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides a succinate, or a succinate intermediate thereof, that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to biologically produced succinate, or a succinate intermediate thereof, as disclosed herein, and to the products derived therefrom, wherein the a succinate, or an intermediate thereof, has a carbon-12, carbon-13, and carbon-14 isotope ratio of about the same value as the $CO_2$ that occurs in the environment. For example, in some aspects the invention provides bio-derived succinate, or an intermediate thereof, having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived succinate, or an intermediate thereof, as disclosed herein, wherein the bio-derived product is chemically modified to generate a final product. Methods of chemically modifying a bioderived product of succinate, or an intermediate thereof, to generate a desired product are well known to those skilled in the art, as described herein. The invention further provides products made or derived from succinate, including but not limited to butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as polypropylene (PP), polystyrene (PS) and polycarbonate (PC), and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, having a carbon-12 versus carbon-13 versus carbon-14 isotope ratio of about the same value as the $CO_2$ that occurs in the environment, wherein the invention further provides products made or derived from succinate, including but not limited to butanediol, tetrahydrofuran, pyrrolidone, solvents, paints, deicers, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, are generated directly from or in combination with bioderived succinate or a bioderived intermediate thereof, as disclosed herein.

Succinate, as well as intermediates thereof, are chemicals used in commercial and industrial applications. Non-limiting examples of such applications include production of butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like. Moreover, succinate are also used as a raw material in the production of a wide range of products including butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like. Accordingly, in some embodiments, the invention provides biobased butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, comprising one or more of bioderived succinate, or a bioderived intermediate thereof, produced by a non-naturally occurring microorganism of the invention or produced using a method disclosed herein.

As used herein, the term "bioderived" means derived from or synthesized by a biological organism and can be considered a renewable resource since it can be generated by a biological organism. Such a biological organism, in particular the microbial organisms of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, comprising bioderived succinate, or a bioderived intermediate thereof, wherein the bioderived succinate, or bioderived intermediate thereof, includes all or part of the a succinate, or an intermediate thereof, used in the production of butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like. Thus, in some aspects, the invention provides a biobased butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived succinate, or a bioderived succinate intermediate, as disclosed herein. Additionally, in some aspects, the invention provides biobased butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, wherein the a succinate, or a succinate intermediate, used in its production is a combination of bioderived and petroleum derived succinate, or a succinate intermediate thereof. For example, biobased butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, can be produced using 50% bioderived succinate and 50% petroleum derived succinate or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, using the bioderived succinate, or a bioderived succinate intermediate thereof, of the invention are well known in the art.

In one embodiment, the product is a butanediol. In one embodiment, the product is a tetrahydrofuran. In one embodiment, the product is a pyrrolidone. In one embodiment, the product is a solvent. In one embodiment, the product is a paint. In one embodiment, the product is a deicer. In one embodiment, the product is a plastic. In one embodiment, the product is a fuel additive. In one embodiment, the product is a fabric. In one embodiment, the product is a carpet. In one embodiment, the product is a pigment. In one embodiment, the product is a detergent. In one embodiment, the product is a metal plating. In one embodiment, the product is a polymer. In one embodiment, the product is a polybutylene succinate polymer. In one embodiment, the product is a biodegradable plastic. In one embodiment, the product is a flexible packaging. In one embodiment, the product is an agricultural film. In one embodiment, the product is a compostable bag. In one embodiment, the product is a combination of polybutylene succinate with polymers such as PP, PS and PC, and with plastics such as polylactic acid, polyhydroxyalkanoate, and poly-3-hydroxy butyrateco-valerate. In one embodiment, the product is a combination of polybutylene succinate with fibers or fillers for applications such as automotive interiors, nonwovens, construction materials and consumer goods.

In some embodiments, provided herein is a culture medium comprising bioderived succinate. In some embodiments, the bioderived succinate is produced by culturing a non-naturally occurring microbial organism having a methanol metabolic pathway and succinate pathway, as provided herein. In certain embodiments, the bioderived succinate has a carbon-12, carbon-13 and carbon-14 isotope ratio that reflects an atmospheric carbon dioxide uptake source. In one embodiment, the culture medium is separated from a non-naturally occurring microbial organism having a methanol metabolic pathway and succinate pathway.

In other embodiments, provided herein is a bioderived succinate. In some embodiments, the bioderived succinate is produced by culturing a non-naturally occurring microbial organism having a methanol metabolic pathway and succinate pathway, as provided herein. In certain embodiments, the bioderived succinate has a carbon-12, carbon-13 and carbon-14 isotope ratio that reflects an atmospheric carbon dioxide uptake source. In some embodiments, the bioderived succinate has an Fm value of at least 80%, at least 85%, at least 90%, at least 95% or at least 98%. In certain embodiments, the bioderived succinate is a component of culture medium.

In certain embodiments, provided herein is a composition comprising a bioderived succinate provided herein, for example, a bioderived succinate produced by culturing a non-naturally occurring microbial organism having a methanol metabolic pathway and succinate pathway, as provided herein. In some embodiments, the composition further comprises a compound other than said bioderived succinate. In certain embodiments, the compound other than said bioderived succinate is a trace amount of a cellular portion of a non-naturally occurring microbial organism having a methanol metabolic pathway and a succinate pathway, as provided herein.

In some embodiments, provided herein is a biobased product comprising a bioderived succinate provided herein. In certain embodiments, the biobased product is a butanediol, tetrahydrofuran, pyrrolidone, solvent, paint, deicer, plastic, fuel additive, fabric, carpet, pigment, detergent, metal plating, polymer, polybutylene succinate polymer, biodegradable plastic, flexible packaging, agricultural film, compostable bag; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like. In certain embodiments, the biobased product comprises at least 5% bioderived succinate. In certain embodiments, the biobased product comprises at least 10% bioderived succinate. In some embodiments, the biobased product comprises at least 20% bioderived succinate. In other embodiments, the biobased product comprises at least 30% bioderived succinate. In some embodiments, the biobased product comprises at least 40% bioderived succinate. In other embodiments, the biobased product comprises at least 50% bioderived succinate. In one embodiment, the biobased product comprises a portion of said bioderived succinate as a repeating unit. In another embodiment, provided herein is a molded product obtained by molding the biobased product provided herein. In other embodiments, provided herein is a process for producing a biobased product provided herein, comprising chemically reacting said bioderived succinate with itself or another compound in a reaction that produces said biobased product. In certain embodiments, provided herein is a polymer comprising or obtained by converting the bioderived succinate. In other embodiments, provided herein is a method for producing a polymer, comprising chemically of enzymatically converting the bioderived succinate to the polymer. In yet other embodiments, provided herein is a composition comprising the bioderived succinate, or a cell lysate or culture supernatant thereof.

The invention is described herein with general reference to the metabolic reaction, reactant or product thereof, or with specific reference to one or more nucleic acids or genes encoding an enzyme associated with or catalyzing the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these metabolic constitutes also references the gene or genes encoding the enzymes that catalyze the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes, or a protein associated with the reaction, as well as the reactants and products of the reaction.

Microbial organisms generally lack the capacity to synthesize succinate, and therefore any of the compounds disclosed herein to be within the succinate family of compounds, or otherwise known by those in the art to be within the succinate family of compounds. Moreover, organisms having all of the requisite metabolic enzymatic capabilities are not known to produce succinate from the enzymes described and biochemical pathways exemplified herein. In contrast, the non-naturally occurring microbial organisms of the invention can generate succinate as a product, as well as intermediates thereof. The biosynthesis of succinate, as well as intermediates thereof, is particularly useful in chemical synthesis of succinate family of compounds, it also allows for the further biosynthesis of succinate family compounds and avoids altogether chemical synthesis procedures.

The non-naturally occurring microbial organisms of the invention that can produce succinate are produced by ensuring that a host microbial organism includes functional capabilities for the complete biochemical synthesis of at least one succinate biosynthetic pathway of the invention. Ensuring at least one requisite succinate biosynthetic pathway confers succinate biosynthesis capability onto the host microbial organism.

The organisms and methods are described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The non-naturally occurring microbial organisms described herein can be produced by introducing expressible nucleic acids encoding one or more of the enzymes or proteins participating in one or more methanol metabolic, formaldehyde assimilation, and/or succinate biosynthetic pathways. Depending on the host microbial organism chosen for biosynthesis, nucleic acids for some or all of a particular methanol metabolic, formaldehyde assimilation, and/or succinate biosynthetic pathway can be expressed. For example, if a chosen host is deficient in one or more enzymes or proteins for a desired metabolic, assimilation, or biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve succinate biosynthesis and/or methanol metabolism. Thus, a non-naturally occurring microbial organism described herein can be produced by introducing exogenous enzyme or protein activities to obtain a desired metabolic pathway and/or a desired biosynthetic pathway can be obtained by introducing one or more exogenous enzyme or protein activities that, together with one or more endogenous enzymes or proteins, produces a desired product such as succinate.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Exemplary yeasts or fungi include species selected from *Saccharomyces cerevisiae, Schizosaccharomyces pombe, Kluyveromyces lactis, Kluyveromyces marxianus, Aspergil-*

*lus terreus, Aspergillus niger, Pichia pastoris, Rhizopus arrhizus, Rhizobus oryzae*, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the succinate biosynthetic, methanol metabolic and/or formaldehyde assimilation pathway constituents of a selected host microbial organism, the non-naturally occurring microbial organisms provided herein will, in some embodiments, include at least one exogenously expressed succinate, formaldehyde assimilation and/or methanol metabolic pathway-encoding nucleic acid and up to all encoding nucleic acids for one or more succinate biosynthetic pathways, formaldehyde assimilation pathways and/or methanol metabolic pathways. For example, succinate biosynthesis can be established in a host deficient in a pathway enzyme or protein through exogenous expression of the corresponding encoding nucleic acid. In a host deficient in all enzymes or proteins of a succinate pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of succinate can be included. The same holds true for the methanol metabolic pathways and formaldehyde assimilation pathways provided herein. In some embodiments, the nucleic acid encoding a succinate pathway enzyme is an exogenous nucleic acid. In other embodiments, the nucleic acid encoding an succinate pathway enzyme is an endogenous nucleic acid.

In certain embodiments, the non-naturally occurring microbial organism comprises (1) a methanol metabolic pathway, wherein said organism comprises one or more exogenous nucleic acids encoding a methanol metabolic pathway enzyme provided herein, and (2) a succinate pathway, but the microbial organism does not further comprise one or more exogenous nucleic acids encoding a succinate pathway enzyme provided herein. In some embodiments, succinate pathway enzyme(s) provided herein are endogenous to the microbial organism and the nucleic acid encoding an succinate pathway enzyme is an endogenous nucleic acid. In other embodiments, only a single succinate pathway enzyme is encoded by an exogenous nucleic acid, e.g., a malic enzyme (FIG. 2, step G), whereas the remaining succinate pathway enzymes are encoded by one or more endogenous nucleic acids.

Given the teachings and guidance provided herein, those skilled in the art will understand that the number of encoding nucleic acids to introduce in an expressible form will, at least, parallel the succinate pathway, formaldehyde assimilation pathway, and methanol metabolic pathway deficiencies of the selected host microbial organism. Therefore, a non-naturally occurring microbial organism of the invention can have one, two, three, four, five, six, seven, eight, nine, or up to all nucleic acids encoding the enzymes or proteins constituting a methanol metabolic pathway, formaldehyde assimilation pathway, and/or succinate biosynthetic pathway disclosed herein. In some embodiments, the non-naturally occurring microbial organisms also can include other genetic modifications that facilitate or optimize succinate biosynthesis, formaldehyde assimilation, and/or methanol metabolism or that confer other useful functions onto the host microbial organism. One such other functionality can include, for example, augmentation of the synthesis of one or more of the succinate pathway precursors.

Generally, a host microbial organism is selected such that it produces the precursor of a succinate pathway, either as a naturally produced molecule or as an engineered product that either provides de novo production of a desired precursor or increased production of a precursor naturally produced by the host microbial organism. A host organism can be engineered to increase production of a precursor, as disclosed herein. In addition, a microbial organism that has been engineered to produce a desired precursor can be used as a host organism and further engineered to express enzymes or proteins of a succinate pathway.

In some embodiments, a non-naturally occurring microbial organism provided herein is generated from a host that contains the enzymatic capability to synthesize succinate, assimilate formaldehyde and/or metabolize methanol. In this specific embodiment it can be useful to increase the synthesis or accumulation of a succinate pathway product, formaldehyde assimilation pathway product and/or methanol metabolic pathway product (e.g., reducing equivalents and/or formaldehyde) to, for example, drive succinate pathway reactions toward succinate production. Increased synthesis or accumulation can be accomplished by, for example, overexpression of nucleic acids encoding one or more of the above-described succinate, formaldehyde assimilation and/or methanol metabolic pathway enzymes or proteins. Over expression the enzyme(s) and/or protein(s) of the succinate pathway, formaldehyde assimilation, and/or methanol metabolic pathway can occur, for example, through exogenous expression of the endogenous gene(s), or through exogenous expression of the heterologous gene(s). Therefore, naturally occurring organisms can be readily generated to be non-naturally occurring microbial organisms, for example, producing succinate through overexpression of one, two, three, four, five, six, seven, eight, up to all nucleic acids encoding succinate biosynthetic pathway, and/or methanol metabolic pathway enzymes or proteins. Naturally occurring organisms can also be readily generated to be non-naturally occurring microbial organisms, for example, assimilating formaldehyde, through overexpression of one, two, three, four, five, six, seven, eight, up to all nucleic acids encoding formaldehyde assimilation pathway, and/or methanol metabolic pathway enzymes or proteins. In addition, a non-naturally occurring organism can be generated by mutagenesis of an endogenous gene that results in an increase in activity of an enzyme in the succinate, formaldehyde assimilation and/or methanol metabolic pathway biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods provided herein, any of the one or more exogenous nucleic acids can be introduced into a microbial organism to produce a non-naturally occurring microbial organism provided herein. The nucleic acids can be introduced so as to confer, for example, a succinate biosynthetic, formaldehyde assimilation and/or methanol metabolic pathway onto the microbial organism. Alternatively, encoding nucleic acids can be introduced to produce an intermediate microbial organism having the biosynthetic capability to catalyze some of the required reactions to confer succinate biosynthetic, formaldehyde assimilation and/or methanol metabolic capability. For example, a non-naturally occurring microbial organism having a succinate biosynthetic pathway, formaldehyde assimilation pathway and/or methanol metabolic pathway can comprise at least two exogenous nucleic acids encoding desired enzymes or proteins. Thus, it is understood that any combination of two or more enzymes or proteins of a biosynthetic pathway, formaldehyde assimilation pathway and/or metabolic pathway can be included in a non-naturally occurring microbial organism provided herein. Similarly, it is understood that any combination of three or more enzymes or proteins of a biosynthetic pathway, formaldehyde assimilation pathway and/or metabolic pathway can be included in a non-naturally occurring microbial organism of the invention, as desired, so long as the combination of enzymes and/or proteins of the desired biosynthetic pathway, formaldehyde assimilation pathway and/or metabolic pathway results in production of the corresponding desired product. Similarly, any combination of four or more enzymes or proteins of a biosynthetic pathway, formaldehyde assimilation pathway and/or methanol metabolic pathway as disclosed herein can be included in a non-naturally occurring microbial organism provided herein, as desired, so long as the combination of enzymes and/or proteins of the desired biosynthetic, assimilation and/or metabolic pathway results in production of the corresponding desired product.

In addition to the metabolism of methanol, assimilation of formaldehyde, and biosynthesis of succinate, as described herein, the non-naturally occurring microbial organisms and methods provided also can be utilized in various combinations with each other and with other microbial organisms and methods well known in the art to achieve product biosynthesis by other routes. For example, one alternative to produce succinate, other than use of the succinate producers is through addition of another microbial organism capable of converting a succinate pathway intermediate to succinate. One such procedure includes, for example, the fermentation of a microbial organism that produces a succinate pathway intermediate. The succinate pathway intermediate can then be used as a substrate for a second microbial organism that converts the succinate pathway intermediate to succinate. The succinate pathway intermediate can be added directly to another culture of the second organism or the original culture of the succinate pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, succinate. In these embodiments, biosynthetic pathways for a desired product can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of succinate can be accomplished by constructing a microbial organism that contains biosynthetic pathways for conversion of one pathway intermediate to another pathway intermediate or the product. Alternatively, succinate also can be biosynthetically produced from microbial organisms through co-culture or co-fermentation using two organisms in the same vessel, where the first microbial organism produces a succinate intermediate and the second microbial organism converts the intermediate to succinate.

Given the teachings and guidance provided herein, those skilled in the art will understand that a wide variety of combinations and permutations exist for the non-naturally occurring microbial organisms and methods together with other microbial organisms, with the co-culture of other non-naturally occurring microbial organisms having subpathways and with combinations of other chemical and/or biochemical procedures well known in the art to produce succinate and/or metabolize methanol.

Sources of encoding nucleic acids for a succinate, formaldehyde assimilation, or methanol metabolic pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Saccharomyces cerevisiae, Saccharomyces kluyveri, Candida boidinii, Clostridium kluyveri, Clostridium acetobutylicum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pediococcus pentosaceus, Zymomonas mobilus, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium*

*nuleatum, Penicillium chrysogenum*, marine gamma proteobacterium, butyrate-producing bacterium, *Nocardia iowensis, Nocardia farcinica, Streptomyces griseus, Schizosaccharomyces pombe, Geobacillus thermoglucosidasius, Salmonella typhimurium, Vibrio cholera, Heliobacter pylori, Nicotiana tabacum, Oryza sativa, Haloferax mediterranei, Agrobacterium tumefaciens, Achromobacter denitrificans, Fusobacterium nucleatum, Streptomyces clavuligenus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnificus, Selenomonas ruminantium, Vibrio parahaemolyticus, Archaeoglobus fulgidus, Haloarcula marismortui, Pyrobaculum aerophilum, Mycobacterium smegmatis* MC2 155, *Mycobacterium avium* subsp. *paratuberculosis* K-10, *Mycobacterium marinum* M, *Tsukamurella paurometabola* DSM 20162, *Cyanobium* PCC7001, *Dictyostelium discoideum* AX4, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite succinate biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of succinate, metabolism of methanol and/or assimilation of formaldehyde described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative succinate biosynthetic, formaldehyde assimilation and/or methanol metabolic pathway exists in an unrelated species, succinate biosynthesis, formaldehyde assimilation and/or methanol metabolism can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods provided herein can be applied to all microbial organisms using the cognate metabolic alterations to those exemplified herein to construct a microbial organism in a species of interest that will synthesize succinate, assimilate formaldehyde, and/or metabolize methanol.

Methods for constructing and testing the expression levels of a non-naturally occurring succinate-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for metabolism of methanol, assimilation of formaldehyde and/or production of succinate can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more succinate biosynthetic, formaldehyde assimilation and/or methanol metabolic pathway encoding nucleic acids as exemplified herein operably linked to expression control sequences functional in the host organism. Expression vectors applicable for use in the microbial host organisms provided include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

Suitable purification and/or assays to test, e.g., for the production of succinate can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme or protein activities from the exogenous DNA sequences can also be assayed using methods well known in the art.

The succinate can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products, or intermediates thereof. For example, the succinate producers can be cultured for the biosynthetic production of succinate. Accordingly, in some embodiments, the invention provides culture medium having a succinate, formaldehyde assimilation and/or methanol metabolic pathway intermediate described herein. In some aspects, the culture medium can also be separated from the non-naturally occurring microbial organisms provided herein that produced the succinate, formaldehyde assimilation and/or methanol metabolic pathway intermediate. Methods for separating a microbial organism from culture medium are well known in the art. Exemplary methods include filtration, flocculation, precipitation, centrifugation, sedimentation, and the like.

In certain embodiments, for example, for the production of the production of succinate, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in U.S. Publ. No. 2009/0047719. Fermentations can be performed in a batch, fed-batch or continuous manner, as disclosed herein. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high succinate yields.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium, can include, for example, any carbohydrate source which can supply a source of carbon to the non-naturally occurring microorganism. Such sources include, for example, sugars such as glucose, xylose, arabinose, galactose, mannose, fructose, sucrose and starch; or glycerol, alone as the sole source of carbon or in combination with other carbon sources described herein or known in the art. In one embodiment, the carbon source is a sugar. In one embodiment, the carbon source is a sugar-containing biomass. In some embodiments, the sugar is glucose. In one embodiment, the sugar is xylose. In another embodiment, the sugar is arabinose. In one embodiment, the sugar is galactose. In another embodiment, the sugar is fructose. In other embodiments, the sugar is sucrose. In one embodiment, the sugar is starch. In certain embodiments, the carbon source is glycerol. In some embodiments, the carbon source is crude glycerol. In one embodiment, the carbon source is crude glycerol without treatment. In other embodiments, the carbon source is glycerol and glucose. In another embodiment, the carbon source is methanol and glycerol. In one embodiment, the carbon source is carbon dioxide. In one embodiment, the carbon source is formate. In one embodiment, the carbon source is methane. In one embodiment, the carbon source is methanol. In one embodiment, the carbon source is chemoelectro-generated carbon (see, e.g., Liao et al. (2012) Science 335:1596). In one embodiment, the chemoelectro-generated carbon is methanol. In one embodiment, the chemoelectro-generated carbon is formate. In one embodiment, the chemoelectro-generated carbon is formate and methanol. In one embodiment, the carbon source is a sugar and methanol. In another embodiment, the carbon source is a sugar and glycerol. In other embodiments, the carbon source is a sugar and crude glycerol. In yet other embodiments, the carbon source is a sugar and crude glycerol without treatment. In one embodiment, the carbon source is a sugar-containing biomass and methanol. In another embodiment, the carbon source is a sugar-containing biomass and glycerol. In other embodiments, the carbon source is a sugar-containing biomass and crude glycerol. In yet other embodiments, the carbon source is a sugar-containing biomass and crude glycerol without treatment. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms provided herein for the production of succinate and other pathway intermediates.

In one embodiment, the carbon source is glycerol. In certain embodiments, the glycerol carbon source is crude glycerol or crude glycerol without further treatment. In a further embodiment, the carbon source comprises glycerol or crude glycerol, and also sugar or a sugar-containing biomass, such as glucose. In a specific embodiment, the concentration of glycerol in the fermentation broth is maintained by feeding crude glycerol, or a mixture of crude glycerol and sugar (e.g., glucose). In certain embodiments, sugar is provided for sufficient strain growth. In some embodiments, the sugar (e.g., glucose) is provided at a molar concentration ratio of glycerol to sugar of from 200:1 to 1:200. In some embodiments, the sugar (e.g., glucose) is provided at a molar concentration ratio of glycerol to sugar of from 100:1 to 1:100. In some embodiments, the sugar (e.g., glucose) is provided at a molar concentration ratio of glycerol to sugar of from 100:1 to 5:1. In some embodiments, the sugar (e.g., glucose) is provided at a molar concentration ratio of glycerol to sugar of from 50:1 to 5:1. In certain embodiments, the sugar (e.g., glucose) is provided at a molar concentration ratio of glycerol to sugar of 100:1. In one embodiment, the sugar (e.g., glucose) is provided at a molar concentration ratio of glycerol to sugar of 90:1. In one embodiment, the sugar (e.g., glucose) is provided at a molar concentration ratio of glycerol to sugar of 80:1. In one embodiment, the sugar (e.g., glucose) is provided at a molar concentration ratio of glycerol to sugar of 70:1. In one embodiment, the sugar (e.g., glucose) is provided at a molar concentration ratio of glycerol to sugar of 60:1. In one embodiment, the sugar (e.g., glucose) is provided at a molar concentration ratio of glycerol to sugar of 50:1. In one embodiment, the sugar (e.g., glucose) is provided at a molar concentration ratio of glycerol to sugar of 40:1. In one embodiment, the sugar (e.g., glucose) is provided at a molar concentration ratio of glycerol to sugar of 30:1. In one embodiment, the sugar (e.g., glucose) is provided at a molar concentration ratio of glycerol to sugar of 20:1. In one embodiment, the sugar (e.g., glucose) is provided at a molar concentration ratio of glycerol to sugar of 10:1. In one embodiment, the sugar (e.g., glucose) is provided at a molar concentration ratio of glycerol to sugar of 5:1. In one embodiment, the sugar (e.g., glucose) is provided at a molar concentration ratio of glycerol to sugar of 2:1. In one embodiment, the sugar (e.g., glucose) is provided at a molar concentration ratio of glycerol to sugar of 1:1. In certain embodiments, the sugar (e.g., glucose) is provided at a molar concentration ratio of glycerol to sugar of 1:100. In one embodiment, the sugar (e.g., glucose) is provided at a molar concentration ratio of glycerol to sugar of 1:90. In one embodiment, the sugar (e.g., glucose) is provided at a molar concentration ratio of glycerol to sugar of 1:80. In one embodiment, the sugar (e.g., glucose) is provided at a molar concentration ratio of glycerol to sugar of 1:70. In one embodiment, the sugar (e.g., glucose) is provided at a molar concentration ratio of glycerol to sugar of 1:60. In one embodiment, the sugar (e.g., glucose) is provided at a molar concentration ratio of glycerol to sugar of 1:50. In one embodiment, the sugar (e.g., glucose) is provided at a molar concentration ratio of glycerol to sugar of 1:40. In one embodiment, the sugar (e.g., glucose) is provided at a molar concentration ratio of glycerol to sugar of 1:30. In one embodiment, the sugar (e.g., glucose) is provided at a molar concentration ratio of glycerol to sugar of 1:20. In one embodiment, the sugar (e.g., glucose) is provided at a molar concentration ratio of glycerol to sugar of 1:10. In one embodiment, the sugar (e.g., glucose) is provided at a molar concentration ratio of glycerol to sugar of 1:5. In one embodiment, the sugar (e.g., glucose) is provided at a molar concentration ratio of glycerol to sugar of 1:2. In certain embodiments of the ratios provided above, the sugar is a sugar-containing biomass. In certain other embodiments of the ratios provided above, the glycerol is a crude glycerol or a crude glycerol without further treatment. In other embodiments of the ratios provided above, the sugar is a sugar-containing biomass, and the glycerol is a crude glycerol or a crude glycerol without further treatment.

Crude glycerol can be a by-product produced in the production of biodiesel, and can be used for fermentation without any further treatment. Biodiesel production methods include (1) a chemical method wherein the glycerol-group of vegetable oils or animal oils is substituted by low-carbon alcohols such as methanol or ethanol to produce a corresponding fatty acid methyl esters or fatty acid ethyl esters by transesterification in the presence of acidic or basic catalysts; (2) a biological method where biological enzymes or cells are used to catalyze transesterification reaction and the corresponding fatty acid methyl esters or fatty acid ethyl esters are produced; and (3) a supercritical method, wherein transesterification reaction is carried out in a supercritical solvent system without any catalysts. The chemical composition of crude glycerol can vary with the process used to produce biodiesel, the transesterification efficiency, recovery efficiency of the biodiesel, other impurities in the feedstock, and whether methanol and catalysts were recovered. For example, the chemical compositions of eleven crude glycerol collected from seven Australian biodiesel producers reported that glycerol content ranged between 38% and 96%, with some samples including more than 14% methanol and 29% ash. In certain embodiments, the crude glycerol comprises from 5% to 99% glycerol. In some embodiments, the crude glycerol comprises from 10% to 90% glycerol. In some embodiments, the crude glycerol comprises from 10% to 80% glycerol. In some embodiments, the crude glycerol comprises from 10% to 70% glycerol. In some embodiments, the crude glycerol comprises from 10% to 60% glycerol. In some embodiments, the crude glycerol comprises from 10% to 50% glycerol. In some embodiments, the crude glycerol comprises from 10% to 40% glycerol. In some embodiments, the crude glycerol comprises from 10% to 30% glycerol. In some embodiments, the crude glycerol comprises from 10% to 20% glycerol. In some embodiments, the crude glycerol comprises from 80% to 90% glycerol. In some embodiments, the crude glycerol comprises from 70% to 90% glycerol. In some embodiments, the crude glycerol comprises from 60% to 90% glycerol. In some embodiments, the crude glycerol comprises from 50% to 90% glycerol. In some embodiments, the crude glycerol comprises from 40% to 90% glycerol. In some embodiments, the crude glycerol comprises from 30% to 90% glycerol. In some embodiments, the crude glycerol comprises from 20% to 90% glycerol. In some embodiments, the crude glycerol comprises from 20% to 40% glycerol. In some embodiments, the crude glycerol comprises from 40% to 60% glycerol. In some embodiments, the crude glycerol comprises from 60% to 80% glycerol. In some embodiments, the crude glycerol comprises from 50% to 70% glycerol. In one embodiment, the glycerol comprises 5% glycerol. In one embodiment, the glycerol comprises 10% glycerol. In one embodiment, the glycerol comprises 15% glycerol. In one embodiment, the glycerol comprises 20% glycerol. In one embodiment, the glycerol comprises 25% glycerol. In one embodiment, the glycerol comprises 30% glycerol. In one embodiment, the glycerol comprises 35% glycerol. In one embodiment, the glycerol comprises 40% glycerol. In one embodiment, the glycerol comprises 45% glycerol. In one embodiment, the glycerol comprises 50% glycerol. In one embodiment, the glycerol comprises 55% glycerol. In one embodiment, the glycerol comprises 60% glycerol. In one embodiment, the glycerol comprises 65% glycerol. In one embodiment, the glycerol comprises 70% glycerol. In one embodiment, the glycerol comprises 75% glycerol. In one embodiment, the glycerol comprises 80% glycerol. In one embodiment, the glycerol comprises 85% glycerol. In one embodiment, the glycerol comprises 90% glycerol. In one embodiment, the glycerol comprises 95% glycerol. In one embodiment, the glycerol comprises 99% glycerol.

In one embodiment, the carbon source is methanol or formate. In certain embodiments, methanol is used as a carbon source in the formaldehyde assimilation pathways provided herein. In one embodiment, the carbon source is methanol or formate. In other embodiments, formate is used as a carbon source in the formaldehyde assimilation pathways provided herein. In specific embodiments, methanol is used as a carbon source in the methanol metabolic pathways provided herein, either alone or in combination with the product pathways provided herein.

In one embodiment, the carbon source comprises methanol, and sugar (e.g., glucose) or a sugar-containing biomass. In another embodiment, the carbon source comprises formate, and sugar (e.g., glucose) or a sugar-containing biomass. In one embodiment, the carbon source comprises methanol, formate, and sugar (e.g., glucose) or a sugar-containing biomass. In specific embodiments, the methanol or formate, or both, in the fermentation feed is provided as a mixture with sugar (e.g., glucose) or sugar-comprising biomass. In certain embodiments, sugar is provided for sufficient strain growth.

In certain embodiments, the carbon source comprises methanol and a sugar (e.g., glucose). In some embodiments, the sugar (e.g., glucose) is provided at a molar concentration ratio of methanol to sugar of from 200:1 to 1:200. In some embodiments, the sugar (e.g., glucose) is provided at a molar concentration ratio of methanol to sugar of from 100:1 to 1:100. In some embodiments, the sugar (e.g., glucose) is provided at a molar concentration ratio of methanol to sugar of from 100:1 to 5:1. In some embodiments, the sugar (e.g., glucose) is provided at a molar concentration ratio of methanol to sugar of from 50:1 to 5:1. In certain embodiments, the sugar (e.g., glucose) is provided at a molar concentration ratio of methanol to sugar of 100:1. In one embodiment, the sugar (e.g., glucose) is provided at a molar concentration ratio of methanol to sugar of 90:1. In one embodiment, the sugar (e.g., glucose) is provided at a molar concentration ratio of methanol to sugar of 80:1. In one embodiment, the sugar (e.g., glucose) is provided at a molar concentration ratio of methanol to sugar of 70:1. In one embodiment, the sugar (e.g., glucose) is provided at a molar concentration ratio of methanol to sugar of 60:1. In one embodiment, the sugar (e.g., glucose) is provided at a molar concentration ratio of methanol to sugar of 50:1. In one embodiment, the sugar (e.g., glucose) is provided at a molar concentration ratio of methanol to sugar of 40:1. In one embodiment, the sugar (e.g., glucose) is provided at a molar concentration ratio of methanol to sugar of 30:1. In one embodiment, the sugar (e.g., glucose) is provided at a molar concentration ratio of methanol to sugar of 20:1. In one embodiment, the sugar (e.g., glucose) is provided at a molar concentration ratio of methanol to sugar of 10:1. In one embodiment, the sugar (e.g., glucose) is provided at a molar concentration ratio of methanol to sugar of 5:1. In one embodiment, the sugar (e.g., glucose) is provided at a molar concentration ratio of methanol to sugar of 2:1. In one embodiment, the sugar (e.g., glucose) is provided at a molar concentration ratio of methanol to sugar of 1:1. In certain embodiments, the sugar (e.g., glucose) is provided at a molar concentration ratio of methanol to sugar of 1:100. In one embodiment, the sugar (e.g., glucose) is provided at a molar concentration ratio of methanol to sugar of 1:90. In one embodiment, the sugar (e.g., glucose) is provided at a molar concentration ratio of methanol to sugar of 1:80. In one embodiment, the sugar (e.g., glucose) is provided at a molar concentration ratio of methanol to sugar of 1:70. In one embodiment, the sugar (e.g., glucose) is provided at a molar concentration ratio of methanol to sugar of 1:60. In one embodiment, the sugar (e.g., glucose) is provided at a molar concentration ratio of methanol to sugar of 1:50. In one embodiment, the sugar (e.g., glucose) is provided at a molar concentration ratio of methanol to sugar of 1:40. In one embodiment, the sugar (e.g., glucose) is provided at a molar concentration ratio of methanol to sugar of 1:30. In one embodiment, the sugar (e.g., glucose) is provided at a molar concentration ratio of methanol to sugar of 1:20. In one embodiment, the sugar (e.g., glucose) is provided at a molar concentration ratio of methanol to sugar of 1:10. In one embodiment, the sugar (e.g., glucose) is provided at a molar concentration ratio of methanol to sugar of 1:5. In one embodiment, the sugar (e.g., glucose) is provided at a molar concentration ratio of methanol to sugar of 1:2. In certain embodiments of the ratios provided above, the sugar is a sugar-containing biomass.

In certain embodiments, the carbon source comprises formate and a sugar (e.g., glucose). In some embodiments, the sugar (e.g., glucose) is provided at a molar concentration ratio of formate to sugar of from 200:1 to 1:200. In some embodiments, the sugar (e.g., glucose) is provided at a molar concentration ratio of formate to sugar of from 100:1 to 1:100. In some embodiments, the sugar (e.g., glucose) is provided at a molar concentration ratio of formate to sugar of from 100:1 to 5:1. In some embodiments, the sugar (e.g., glucose) is provided at a molar concentration ratio of formate to sugar of from 50:1 to 5:1. In certain embodiments, the sugar (e.g., glucose) is provided at a molar concentration ratio of formate to sugar of 100:1. In one embodiment, the sugar (e.g., glucose) is provided at a molar concentration ratio of formate to sugar of 90:1. In one embodiment, the sugar (e.g., glucose) is provided at a molar concentration ratio of formate to sugar of 80:1. In one embodiment, the sugar (e.g., glucose) is provided at a molar concentration ratio of formate to sugar of 70:1. In one embodiment, the sugar (e.g., glucose) is provided at a molar concentration ratio of formate to sugar of 60:1. In one embodiment, the sugar (e.g., glucose) is provided at a molar concentration ratio of formate to sugar of 50:1. In one embodiment, the sugar (e.g., glucose) is provided at a molar concentration ratio of formate to sugar of 40:1. In one embodiment, the sugar (e.g., glucose) is provided at a molar concentration ratio of formate to sugar of 30:1. In one embodiment, the sugar (e.g., glucose) is provided at a molar concentration ratio of formate to sugar of 20:1. In one embodiment, the sugar (e.g., glucose) is provided at a molar concentration ratio of formate to sugar of 10:1. In one embodiment, the sugar (e.g., glucose) is provided at a molar concentration ratio of formate to sugar of 5:1. In one embodiment, the sugar (e.g., glucose) is provided at a molar concentration ratio of formate to sugar of 2:1. In one embodiment, the sugar (e.g., glucose) is provided at a molar concentration ratio of formate to sugar of 1:1. In certain embodiments, the sugar (e.g., glucose) is provided at a molar concentration ratio of formate to sugar of 1:100. In one embodiment, the sugar (e.g., glucose) is provided at a molar concentration ratio of formate to sugar of 1:90. In one embodiment, the sugar (e.g., glucose) is provided at a molar concentration ratio of formate to sugar of 1:80. In one embodiment, the sugar (e.g., glucose) is provided at a molar concentration ratio of formate to sugar of 1:70. In one embodiment, the sugar (e.g., glucose) is provided at a molar concentration ratio of formate to sugar of 1:60. In one embodiment, the sugar (e.g., glucose) is provided at a molar concentration ratio of formate to sugar of 1:50. In one embodiment, the sugar (e.g., glucose) is provided at a molar concentration ratio of formate to sugar of 1:40. In one embodiment, the sugar (e.g., glucose) is provided at a molar concentration ratio of formate to sugar of 1:30. In one embodiment, the sugar (e.g., glucose) is provided at a molar concentration ratio of formate to sugar of 1:20. In one embodiment, the sugar (e.g., glucose) is provided at a molar concentration ratio of formate to sugar of 1:10. In one embodiment, the sugar (e.g., glucose) is provided at a molar concentration ratio of formate to sugar of 1:5. In one embodiment, the sugar (e.g., glucose) is provided at a molar concentration ratio of formate to sugar of 1:2. In certain embodiments of the ratios provided above, the sugar is a sugar-containing biomass.

In certain embodiments, the carbon source comprises a mixture of methanol and formate, and a sugar (e.g., glucose). In certain embodiments, sugar is provided for sufficient strain growth. In some embodiments, the sugar (e.g., glucose) is provided at a molar concentration ratio of methanol and formate to sugar of from 200:1 to 1:200. In some embodiments, the sugar (e.g., glucose) is provided at a molar concentration ratio of methanol and formate to sugar of from 100:1 to 1:100. In some embodiments, the sugar (e.g., glucose) is provided at a molar concentration ratio of methanol and formate to sugar of from 100:1 to 5:1. In some embodiments, the sugar (e.g., glucose) is provided at a molar concentration ratio of methanol and formate to sugar of from 50:1 to 5:1. In certain embodiments, the sugar (e.g., glucose) is provided at a molar concentration ratio of methanol and formate to sugar of 100:1. In one embodiment, the sugar (e.g., glucose) is provided at a molar concentration ratio of methanol and formate to sugar of 90:1. In one embodiment, the sugar (e.g., glucose) is provided at a molar concentration ratio of methanol and formate to sugar of 80:1. In one embodiment, the sugar (e.g., glucose) is provided at a molar concentration ratio of methanol and formate to sugar of 70:1. In one embodiment, the sugar (e.g., glucose) is provided at a molar concentration ratio of methanol and formate to sugar of 60:1. In one embodiment, the sugar (e.g., glucose) is provided at a molar concentration ratio of methanol and formate to sugar of 50:1. In one embodiment, the sugar (e.g., glucose) is provided at a molar concentration ratio of methanol and formate to sugar of 40:1. In one embodiment, the sugar (e.g., glucose) is provided at a molar concentration ratio of methanol and formate to sugar of 30:1. In one embodiment, the sugar (e.g., glucose) is provided at a molar concentration ratio of methanol and formate to sugar of 20:1. In one embodiment, the sugar (e.g., glucose) is provided at a molar concentration ratio of methanol and formate to sugar of 10:1. In one embodiment, the sugar (e.g., glucose) is provided at a molar concentration ratio of methanol and formate to sugar of 5:1. In one embodiment, the sugar (e.g., glucose) is provided at a molar concentration ratio of methanol and formate to sugar of 2:1. In one embodiment, the sugar (e.g., glucose) is provided at a molar concentration ratio of methanol and formate to sugar of 1:1. In certain embodiments, the sugar (e.g., glucose) is provided at a molar concentration ratio of methanol and formate to sugar of 1:100. In one embodiment, the sugar (e.g., glucose) is provided at a molar concentration ratio of methanol and formate to sugar of 1:90. In one embodiment, the sugar (e.g., glucose) is provided at a molar concentration ratio of methanol and formate to sugar of 1:80. In one embodiment, the sugar (e.g., glucose) is provided at a molar concentration ratio of methanol and formate to sugar of 1:70. In one embodiment, the sugar (e.g., glucose) is provided at a molar concentration ratio of methanol and formate to sugar of 1:60. In one embodiment, the sugar (e.g., glucose) is provided at a molar concentration ratio of methanol and formate to sugar of 1:50. In one embodiment, the sugar (e.g., glucose) is provided at a molar concentration ratio of methanol and formate to sugar of 1:40. In one embodiment, the sugar (e.g., glucose) is provided at a molar concentration ratio of methanol and formate to sugar of 1:30. In one embodiment, the sugar (e.g., glucose) is provided at a molar concentration ratio of methanol and formate to sugar of 1:20. In one embodiment, the sugar (e.g., glucose) is provided at a molar concentration ratio of methanol and formate to sugar of 1:10. In one embodiment, the sugar (e.g., glucose) is provided at a molar concentration ratio of methanol and formate to sugar of 1:5. In one embodiment, the sugar (e.g., glucose) is provided at a molar concentration ratio of methanol and formate to sugar of 1:2. In certain embodiments of the ratios provided above, the sugar is a sugar-containing biomass.

Given the teachings and guidance provided herein, those skilled in the art will understand that a non-naturally occurring microbial organism can be produced that secretes the biosynthesized compounds when grown on a carbon source such as a carbohydrate. Such compounds include, for example, succinate and any of the intermediate metabolites in the succinate pathway. All that is required is to engineer in one or more of the required enzyme or protein activities to achieve biosynthesis of the desired compound or intermediate including, for example, inclusion of some or all of the succinate biosynthetic pathways. Accordingly, provided herein is a non-naturally occurring microbial organism that produces and/or secretes succinate when grown on a carbohydrate or other carbon source and produces and/or secretes any of the intermediate metabolites shown in the succinate pathway when grown on a carbohydrate or other carbon source. The succinate-producing microbial organisms provided herein can initiate synthesis from an intermediate. The same holds true for intermediates in the formaldehyde assimilation and methanol metabolic pathways.

The non-naturally occurring microbial organisms provided herein are constructed using methods well known in the art as exemplified herein to endogenously or exogenously express at least one nucleic acid encoding a succinate biosynthetic pathway and/or exogenously express a methanol metabolic pathway enzyme or protein in sufficient amounts to produce succinate. It is understood that the microbial organisms are cultured under conditions sufficient to produce succinate. Following the teachings and guidance provided herein, the non-naturally occurring microbial organisms can achieve biosynthesis of succinate, resulting in intracellular concentrations between about 0.1-500 mM or more. Generally, the intracellular concentration of succinate is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms provided herein.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. Publ. No. 2009/0047719. Any of these conditions can be employed with the non-naturally occurring microbial organisms as well as other anaerobic conditions well known in the art. Under such anaerobic or substantially anaerobic conditions, the succinate producers can synthesize succinate at intracellular concentrations of 5-100 mM or more as well as all other concentrations exemplified herein. It is understood that, even though the above description refers to intracellular concentrations, succinate can produce succinate intracellularly and/or secrete the product into the culture medium.

Exemplary fermentation processes include, but are not limited to, fed-batch fermentation and batch separation; fed-batch fermentation and continuous separation; and continuous fermentation and continuous separation. In an exemplary batch fermentation protocol, the production organism is grown in a suitably sized bioreactor sparged with an appropriate gas. Under anaerobic conditions, the culture is sparged with an inert gas or combination of gases, for example, nitrogen, N2/CO2 mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the growth characteristics of the production organism and/or desired conditions for the fermentation process. Growth continues for a desired period of time to achieve desired characteristics of the culture in the fermenter, for example, cell density, product concentration, and the like. In a batch fermentation process, the time period for the fermentation is generally in the range of several hours to several days, for example, 8 to 24 hours, or 1, 2, 3, 4 or 5 days, or up to a week, depending on the desired culture conditions. The pH can be controlled or not, as desired, in which case a culture in which pH is not controlled will typically decrease to pH 3-6 by the end of the run. Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermenation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

In addition to the culturing and fermentation conditions disclosed herein, growth condition for achieving biosynthesis of succinate can include the addition of an osmoprotectant to the culturing conditions. In certain embodiments, the non-naturally occurring microbial organisms provided herein can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropronate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of succinate, as well as other pathway intermediates, includes anaerobic culture or fermentation conditions. In certain embodiments, the non-naturally occurring microbial organisms provided can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of succinate. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of succinate. Generally, and as with non-continuous culture procedures, the continuous and/or near-continuous production of succinate will include culturing a non-naturally occurring succinate producing organism of the invention in sufficient nutrients and medium to sustain and/or nearly sustain growth in an exponential phase. Continuous culture under such conditions can be included, for example, growth for 1 day, 2, 3, 4, 5, 6 or 7 days or more. Additionally, continuous culture can include longer time periods of 1 week, 2, 3, 4 or 5 or more weeks and up to several months. Alternatively, organisms provided can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of succinate can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the succinate producers for continuous production of substantial quantities of succinate, the succinate producers also can be, for example, simultaneously subjected to chemical synthesis procedures to convert the product to other compounds or the product can be separated from the fermentation culture and sequentially subjected to chemical conversion to convert the product to other compounds, if desired.

To generate better producers, metabolic modeling can be utilized to optimize growth conditions. Modeling can also be used to design gene knockouts that additionally optimize utilization of the pathway (see, for example, U.S. Publ. Nos. 2002/0012939, 2003/0224363, 2004/0029149, 2004/0072723, 2003/0059792, 2002/0168654 and 2004/0009466, and U.S. Pat. No. 7,127,379). Modeling analysis allows reliable predictions of the effects on cell growth of shifting the metabolism towards more efficient production of succinate.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. Publ. No. 2002/0168654, International Patent Application No. PCT/US02/00660, and U.S. Publ. No. 2009/0047719.

Another computational method for identifying and designing metabolic alterations favoring biosynthetic production of a product is a metabolic modeling and simulation system termed SimPheny®. This computational method and system is described in, for example, U.S. Publ. No. 2003/0233218, and International Patent Application No. PCT/US03/18838. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. Publ. Nos. 2002/0012939, 2003/0224363, 2004/0029149, 2004/0072723, 2003/0059792, 2002/0168654 and 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a succinate pathway, formaldehyde assimilation pathway, and/or methanol metabolic pathway can be introduced into a host organism. In some cases, it can be desirable to modify an activity of a succinate pathway or methanol metabolic pathway enzyme or protein to increase production of succinate; formaldehyde, and/or reducing equivalents. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >10$^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng.* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng.* 22:1-9 (2005); and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a succinate pathway and/or a methanol metabolic pathway enzyme or protein. Such methods include, but are not limited to EpPCR, which introduces random point mutations by reducing the fidelity of DNA polymerase in PCR reactions (Pritchard et al., *J. Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protocols* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc. Natl. Acad. Sci. U.S.A.* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res.* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol.* 352:191-204 (2007); Bergquist et al., *Biomol. Eng.* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. U.S.A.* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res.* 29:E16 (2001)); SCRATCHY, which combines two methods for recombining genes, ITCHY and DNA shuffling (Lutz et al., *Proc. Natl. Acad. Sci. U.S.A.* 98:11248-11253 (2001)); Random Drift Mutagenesis (RNDM), in which mutations made via epPCR are followed by screening/selection for those retaining usable activity (Bergquist et al., *Biomol. Eng.* 22:61-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional is mutator plasmids, utilizing the mutD5 gene, which encodes a mutant subunit of DNA polymerase III, to allow increases of 20 to 4000-× in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. U.S.A.* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. U.S.A.* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., *Nat. Protocols* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

It is understood that modifications which do not substantially affect the activity of the various embodiments of this invention are also included within the definition of the invention provided herein. Accordingly, the following examples are intended to illustrate but not limit the present invention.

4. EXAMPLES

4.1 Example I

Production of Reducing Equivalents Via a Methanol Metabolic Pathway

Exemplary methanol metabolic pathways are provided in FIG. 1.

FIG. 1, Step A—Methanol Methyltransferase

A complex of 3-methyltransferase proteins, denoted MtaA, MtaB, and MtaC, perform the desired methanol methyltransferase activity (Sauer et al., *Eur. J. Biochem.* 243:670-677 (1997); Naidu and Ragsdale, *J. Bacteriol.* 183:3276-3281 (2001); Tallant and Krzycki, *J. Biol. Chem.* 276:4485-4493 (2001); Tallant and Krzycki, *J. Bacteriol.* 179:6902-6911 (1997); Tallant and Krzycki, *J. Bacteriol.* 178:1295-1301 (1996); Ragsdale, S. W., *Crit. Rev. Biochem. Mol. Biol.* 39:165-195 (2004)).

MtaB is a zinc protein that can catalyze the transfer of a methyl group from methanol to MtaC, a corrinoid protein. Exemplary genes encoding MtaB and MtaC can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoacetica* (Das et al., *Proteins* 67:167-176 (2007). In general, the MtaB and MtaC genes are adjacent to one another on the chromosome as their activities are tightly interdependent. The protein sequences of various MtaB and MtaC encoding genes in *M. barkeri*, *M. acetivorans*, and *M. thermoaceticum* can be identified by their following GenBank accession numbers.

| Protein | GenBank ID | GI number | Organism |
| --- | --- | --- | --- |
| MtaB1 | YP_304299 | 73668284 | Methanosarcina barkeri |
| MtaC1 | YP_304298 | 73668283 | Methanosarcina barkeri |
| MtaB2 | YP_307082 | 73671067 | Methanosarcina barkeri |
| MtaC2 | YP_307081 | 73671066 | Methanosarcina barkeri |
| MtaB3 | YP_304612 | 73668597 | Methanosarcina barkeri |
| MtaC3 | YP_304611 | 73668596 | Methanosarcina barkeri |
| MtaB1 | NP_615421 | 20089346 | Methanosarcina acetivorans |
| MtaB1 | NP_615422 | 20089347 | Methanosarcina acetivorans |
| MtaB2 | NP_619254 | 20093179 | Methanosarcina acetivorans |
| MtaC2 | NP_619253 | 20093178 | Methanosarcina acetivorans |
| MtaB3 | NP_616549 | 20090474 | Methanosarcina acetivorans |
| MtaC3 | NP_616550 | 20090475 | Methanosarcina acetivorans |
| MtaB | YP_430066 | 83590057 | Moorella thermoacetica |
| MtaC | YP_430065 | 83590056 | Moorella thermoacetica |
| MtaA | YP_430064 | 83590056 | Moorella thermoacetica |

MtaB is a zinc protein that can catalyze the transfer of a methyl group from methanol to MtaC, a corrinoid protein. Exemplary genes encoding MtaB and MtaC can be found in methanogenic archaea such as *Methanosarcina barkeri* (Maeder et al., *J. Bacteriol.* 188:7922-7931 (2006) and Methanosarcina acetivorans (Galagan et al., *Genome Res.* 12:532-542 (2002), as well as the acetogen, *Moorella thermoacetica* (Das et al., *Proteins* 67:167-176 (2007). In general, the MtaB and MtaC genes are adjacent to one another on the chromosome as their activities are tightly interdependent. The protein sequences of various MtaB and MtaC encoding genes in *M. barkeri*, *M. acetivorans*, and *M. thermoaceticum* can be identified by their following GenBank accession numbers.

The MtaB1 and MtaC1 genes, YP_304299 and YP_304298, from *M. barkeri* were cloned into *E. coli* and sequenced (Sauer et al., *Eur. J. Biochem.* 243:670-677 (1997)). The crystal structure of this methanol-cobalamin methyltransferase complex is also available (Hagemeier et al., *Proc. Natl. Acad. Sci. U.S.A.* 103:18917-18922 (2006)). The MtaB genes, YP_307082 and YP_304612, in *M. barkeri* were identified by sequence homology to YP_304299. In general, homology searches are an effective means of identifying methanol methyltransferases because MtaB encoding genes show little or no similarity to methyltransferases that act on alternative substrates such as trimethylamine, dimethylamine, monomethylamine, or dimethylsulfide. The MtaC genes, YP_307081 and YP_304611 were identified based on their proximity to the MtaB genes and also their homology to YP_304298. The three sets of MtaB and MtaC genes from *M. acetivorans* have been genetically, physiologically, and biochemically characterized (Pritchett and Metcalf, *Mol. Microbiol.* 56:1183-1194 (2005)). Mutant strains lacking two of the sets were able to grow on methanol, whereas a strain lacking all three sets of MtaB and MtaC genes sets could not grow on methanol. This suggests that each set of genes plays a role in methanol utilization. The *M. thermoacetica* MtaB gene was identified based on homology to the methanogenic MtaB genes and also by its adjacent chromosomal proximity to the methanol-induced corrinoid protein, MtaC, which has been crystallized (Zhou et al., *Acta Crystallogr. Sect. F. Struct. Biol. Cyrst. Commun.* 61:537-540 (2005) and further characterized by Northern hybridization and Western Blotting ((Das et al., *Proteins* 67:167-176 (2007)).

MtaA is zinc protein that catalyzes the transfer of the methyl group from MtaC to either Coenzyme M in methanogens or methyltetrahydrofolate in acetogens. MtaA can also utilize methylcobalamin as the methyl donor. Exemplary genes encoding MtaA can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoacetica* ((Das et al., *Proteins* 67:167-176 (2007)). In general, MtaA proteins that catalyze the transfer of the methyl group from $CH_3$-MtaC are difficult to identify bioinformatically as they share similarity to other corrinoid protein methyltransferases and are not oriented adjacent to the MtaB and MtaC genes on the chromosomes. Nevertheless, a number of MtaA encoding genes have been characterized. The protein sequences of these genes in *M. barkeri* and *M. acetivorans* can be identified by the following GenBank accession numbers.

| Protein | GenBank ID | GI number | Organism |
|---|---|---|---|
| MtaA | YP_304602 | 73668587 | *Methanosarcina barkeri* |
| MtaA1 | NP_619241 | 20093166 | *Methanosarcina acetivorans* |
| MtaA2 | NP_616548 | 20090473 | *Methanosarcina acetivorans* |

MtaA is zinc protein that catalyzes the transfer of the methyl group from MtaC to either Coenzyme M in methanogens or methyltetrahydrofolate in acetogens. MtaA can also utilize methylcobalamin as the methyl donor. Exemplary genes encoding MtaA can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoacetica* ((Das et al., *Proteins* 67:167-176 (2007)). In general, MtaA proteins that catalyze the transfer of the methyl group from $CH_3$-MtaC are difficult to identify bioinformatically as they share similarity to other corrinoid protein methyltransferases and are not oriented adjacent to the MtaB and MtaC genes on the chromosomes. Nevertheless, a number of MtaA encoding genes have been characterized. The protein sequences of these genes in *M. barkeri* and *M. acetivorans* can be identified by the following GenBank accession numbers.

The MtaA gene, YP_304602, from *M. barkeri* was cloned, sequenced, and functionally overexpressed in *E. coli* (Harms and Thauer, *Eur. J. Biochem.* 235:653-659 (1996)). In *M. acetivorans*, MtaA1 is required for growth on methanol, whereas MtaA2 is dispensable even though methane production from methanol is reduced in MtaA2 mutants (Bose et al., *J. Bacteriol.* 190:4017-4026 (2008)). There are multiple additional MtaA homologs in *M. barkeri* and *M. acetivorans* that are as yet uncharacterized, but may also catalyze corrinoid protein methyltransferase activity.

Putative MtaA encoding genes in *M. thermoacetica* were identified by their sequence similarity to the characterized methanogenic MtaA genes. Specifically, three *M. thermoacetica* genes show high homology (>30% sequence identity) to YP_304602 from *M. barkeri*. Unlike methanogenic MtaA proteins that naturally catalyze the transfer of the methyl group from $CH_3$-MtaC to Coenzyme M, an *M. thermoacetica* MtaA is likely to transfer the methyl group to methyltetrahydrofolate given the similar roles of methyltetrahydrofolate and Coenzyme M in methanogens and acetogens, respectively. The protein sequences of putative MtaA encoding genes from *M. thermoacetica* can be identified by the following GenBank accession numbers.

| Protein | GenBank ID | GI number | Organism |
|---|---|---|---|
| MtaA | YP_430937 | 83590928 | *Moorella thermoacetica* |
| MtaA | YP_431175 | 83591166 | *Moorella thermoacetica* |
| MtaA | YP_430935 | 83590926 | *Moorella thermoacetica* |
| MtaA | YP_430064 | 83590056 | *Moorella thermoacetica* |

FIG. 1, Step B—Methylenetetrahydrofolate Reductase

The conversion of methyl-THF to methylenetetrahydrofolate is catalyzed by methylenetetrahydrofolate reductase. In *M. thermoacetica*, this enzyme is oxygen-sensitive and contains an iron-sulfur cluster (Clark and Ljungdahl, *J. Biol. Chem.* 259:10845-10849 (1984). This enzyme is encoded by metF in *E. coli* (Sheppard et al., *J. Bacteriol.* 181:718-725 (1999) and CHY_1233 in *C. hydrogenoformans* (Wu et al., *PLoS Genet.* 1:e65 (2005). The *M. thermoacetica* genes, and its *C. hydrogenoformans* counterpart, are located near the CODH/ACS gene cluster, separated by putative hydrogenase and heterodisulfide reductase genes. Some additional gene candidates found bioinformatically are listed below. In *Acetobacterium woodii* metF is coupled to the Rnf complex through RnfC2 (Poehlein et al, *PLoS One.* 7:e33439). Homologs of RnfC are found in other organisms by blast search. The Rnf complex is known to be a reversible complex (Fuchs (2011) *Annu. Rev. Microbiol.* 65:631-658).

| Protein | GenBank ID | GI number | Organism |
|---|---|---|---|
| Moth_1191 | YP_430048.1 | 83590039 | Moorella thermoacetica |
| Moth_1192 | YP_430049.1 | 83590040 | Moorella thermoacetica |
| metF | NP_418376.1 | 16131779 | Escherichia coli |
| CHY_1233 | YP_360071.1 | 78044792 | Carboxydothermus hydrogenoformans |
| CLJU_c37610 | YP_003781889.1 | 300856905 | Clostridium ljungdahlii DSM13528 |
| DesfrDRAFT_3717 | ZP_07335241.1 | 303248996 | Desulfovibrio fructosovorans JJ |
| CcarbDRAFT_2950 | ZP_05392950.1 | 255526026 | Clostridium carboxidivorans P7 |
| Cce174_010100023124 | ZP_07633513.1 | 307691067 | Clostridium cellulovorans 743B |
| Cphy_3110 | YP_001560205.1 | 160881237 | Clostridium phytofermentans ISDg |

FIG. 1, Steps C and D—Methylenetetrahydrofolate Dehydrogenase, Methenyltetrahydrofolate Cyclohydrolase In *M. thermoacetica, E. coli*, and *C. hydrogenoformans*, methenyltetrahydrofolate cyclohydrolase and methylenetetrahydrofolate dehydrogenase are carried out by the bifunctional gene products of Moth_1516, folD, and CHY_1878, respectively (Pierce et al., *Environ. Microbiol.* 10:2550-2573 (2008); Wu et al., *PLoS Genet.* 1:e65 (2005); D'Ari and Rabinowitz, *J. Biol. Chem.* 266:23953-23958 (1991)). A homolog exists in *C. carboxidivorans* P7. Several other organisms also encode for this bifunctional protein as tabulated below.

*Bacteriol.* 170:3255-3261 (1988), and CHY_2385 in *C. hydrogenoformans* (Wu et al., *PLoS Genet.* 1:e65 (2005). Homologs exist in *C. carboxidivorans* P7. This enzyme is found in several other organisms as listed below.

| Protein | GenBank ID | GI number | Organism |
|---|---|---|---|
| Moth_0109 | YP_428991.1 | 83588982 | Moorella thermoacetica |
| CHY_2385 | YP_361182.1 | 78045024 | Carboxydothermus hydrogenoformans |

| Protein | GenBank ID | GI number | Organism |
|---|---|---|---|
| Moth_1516 | YP_430368.1 | 83590359 | Moorella thermoacetica |
| folD | NP_415062.1 | 16128513 | Escherichia coli |
| CHY_1878 | YP_360698.1 | 78044829 | Carboxydothermus hydrogenoformans |
| CcarbDRAFT_2948 | ZP_05392948.1 | 255526024 | Clostridium carboxidivorans P7 |
| folD | ADK16789.1 | 300437022 | Clostridium ljungdahlii DSM13528 |
| folD-2 | NP_951919.1 | 39995968 | Geobacter sulfurreducens PCA |
| folD | YP_725874.1 | 113867385 | Ralstonia eutropha H16 |
| folD | NP_348702.1 | 15895353 | Clostridium acetobutylicum ATCC 824 |
| folD | YP_696506.1 | 110800457 | Clostridium perfringens |
| MGA3_09460 | EIJ83438.1 | 387591119 | Bacillus methanolicus MGA3 |
| PB1_14689 | ZP_10132349.1 | 387929672 | Bacillus methanolicus PB1 |

FIG. 1, Step E—Formyltetrahydrofolate Deformylase

This enzyme catalyzes the hydrolysis of 10-formyltetrahydrofolate (formyl-THF) to THF and formate. In *E. coli*, this enzyme is encoded by purU and has been overproduced, purified, and characterized (Nagy, et al., *J. Bacteria* 3:1292-1298 (1995)). Homologs exist in *Corynebacterium* sp. U-96 (Suzuki, et al., *Biosci. Biotechnol. Biochem.* 69(5):952-956 (2005)), *Corynebacterium glutamicum* ATCC 14067, *Salmonella enterica*, and several additional organisms.

| Protein | GenBank ID | GI number | Organism |
|---|---|---|---|
| purU | AAC74314.1 | 1787483 | Escherichia coli K-12 MG1655 |
| purU | BAD97821.1 | 63002616 | Corynebacterium sp. U-96 |
| purU | EHE84645.1 | 354511740 | Corynebacterium glutamicum ATCC 14067 |
| purU | NP_460715.1 | 16765100 | Salmonella enterica subsp. enterica serovar Typhimurium str. LT2 |

FIG. 1, Step F—Formyltetrahydrofolate Synthetase

Formyltetrahydrofolate synthetase ligates formate to tetrahydrofolate at the expense of one ATP. This reaction is catalyzed by the gene product of Moth_0109 in *M. thermoacetica* (O'brien et al., *Experientia Suppl.* 26:249-262 (1976); Lovell et al., *Arch. Microbiol.* 149:280-285 (1988); Lovell et al., *Biochemistry* 29:5687-5694 (1990)), FHS in *Clostridium acidurici* (Whitehead and Rabinowitz, *J. Bacteriol.* 167:203-209 (1986); Whitehead and Rabinowitz, *J.*

-continued

| Protein | GenBank ID | GI number | Organism |
|---|---|---|---|
| FHS | P13419.1 | 120562 | Clostridium acidurici |
| CcarbDRAFT_1913 | ZP_05391913.1 | 255524966 | Clostridium carboxidivorans P7 |
| CcarbDRAFT_2946 | ZP_05392946.1 | 255526022 | Clostridium carboxidivorans P7 |
| Dhaf_0555 | ACL18622.1 | 219536883 | Desulfitobacterium hafniense |
| Fhs | YP_001393842.1 | 153953077 | Clostridium kluyveri DSM 555 |
| Fhs | YP_003781893.1 | 300856909 | Clostridium ljungdahlii DSM 13528 |
| MGA3_08300 | EIJ83208.1 | 387590889 | Bacillus methanolicus MGA3 |
| PB1_13509 | ZP_10132113.1 | 387929436 | Bacillus methanolicus PB1 |

FIG. 1, Step G—Formate Hydrogen Lyase

A formate hydrogen lyase enzyme can be employed to convert formate to carbon dioxide and hydrogen. An exemplary formate hydrogen lyase enzyme can be found in *Escherichia coli*. The *E. coli* formate hydrogen lyase consists of hydrogenase 3 and formate dehydrogenase-H (Maeda et al., *Appl Microbiol Biotechnol* 77:879-890 (2007)). It is activated by the gene product of fhlA. (Maeda et al., *Appl Microbiol Biotechnol* 77:879-890 (2007)). The addition of the trace elements, selenium, nickel and molybdenum, to a fermentation broth has been shown to enhance formate hydrogen lyase activity (Soini et al., *Microb. Cell Fact.* 7:26 (2008)). Various hydrogenase 3, formate dehydrogenase and transcriptional activator genes are shown below.

| Protein | GenBank ID | GI number | Organism |
|---|---|---|---|
| hycA | NP_417205 | 16130632 | *Escherichia coli* K-12 MG1655 |
| hycB | NP_417204 | 16130631 | *Escherichia coli* K-12 MG1655 |
| hycC | NP_417203 | 16130630 | *Escherichia coli* K-12 MG1655 |
| hycD | NP_417202 | 16130629 | *Escherichia coli* K-12 MG1655 |
| hycE | NP_417201 | 16130628 | *Escherichia coli* K-12 MG1655 |
| hycF | NP_417200 | 16130627 | *Escherichia coli* K-12 MG1655 |
| hycG | NP_417199 | 16130626 | *Escherichia coli* K-12 MG1655 |
| hycH | NP_417198 | 16130625 | *Escherichia coli* K-12 MG1655 |
| hycI | NP_417197 | 16130624 | *Escherichia coli* K-12 MG1655 |
| fdhF | NP_418503 | 16131905 | *Escherichia coli* K-12 MG1655 |
| fhlA | NP_417211 | 16130638 | *Escherichia coli* K-12 MG1655 |

A formate hydrogen lyase enzyme also exists in the hyperthermophilic archaeon, *Thermococcus litoralis* (Takacs et al., *BMC. Microbiol* 8:88 (2008)).

| Protein | GenBank ID | GI number | Organism |
|---|---|---|---|
| mhyC | ABW05543 | 157954626 | *Thermococcus litoralis* |
| mhyD | ABW05544 | 157954627 | *Thermococcus litoralis* |
| mhyE | ABW05545 | 157954628 | *Thermococcus litoralis* |
| myhF | ABW05546 | 157954629 | *Thermococcus litoralis* |
| myhG | ABW05547 | 157954630 | *Thermococcus litoralis* |
| myhH | ABW05548 | 157954631 | *Thermococcus litoralis* |
| fdhA | AAB94932 | 2746736 | *Thermococcus litoralis* |
| fdhB | AAB94931 | 157954625 | *Thermococcus litoralis* |

Additional formate hydrogen lyase systems have been found in *Salmonella typhimurium, Klebsiella pneumoniae, Rhodospirillum rubrum, Methanobacterium formicicum* (Vardar-Schara et al., Microbial Biotechnology 1:107-125 (2008)).

FIG. 1, Step H—Hydrogenase

Hydrogenase enzymes can convert hydrogen gas to protons and transfer electrons to acceptors such as ferredoxins, NAD+, or NADP+. *Ralstonia eutropha* H16 uses hydrogen as an energy source with oxygen as a terminal electron acceptor. Its membrane-bound uptake [NiFe]-hydrogenase is an "O2-tolerant" hydrogenase (Cracknell, et al. Proc Nat Acad Sci, 106(49) 20681-20686 (2009)) that is periplasmically-oriented and connected to the respiratory chain via a b-type cytochrome (Schink and Schlegel, *Biochim. Biophys. Acta*, 567, 315-324 (1979); Bernhard et al., *Eur. J. Biochem.* 248, 179-186 (1997)). *R. eutropha* also contains an $O_2$-tolerant soluble hydrogenase encoded by the Hox operon which is cytoplasmic and directly reduces NAD+ at the expense of hydrogen (Schneider and Schlegel, *Biochim. Biophys. Acta* 452, 66-80 (1976); Burgdorf, *J Bact.* 187(9) 3122-3132 (2005)). Soluble hydrogenase enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.*, 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from *Nostoc* sp. PCC 7120 led to increased hydrogenase activity compared to expression of the Hox genes alone (Germer, *J. Biol. Chem.* 284(52), 36462-36472 (2009)).

| Protein | GenBank ID | GI Number | Organism |
|---|---|---|---|
| HoxF | NP_942727.1 | 38637753 | *Ralstonia eutropha* H16 |
| HoxU | NP_942728.1 | 38637754 | *Ralstonia eutropha* H16 |
| HoxY | NP_942729.1 | 38637755 | *Ralstonia eutropha* H16 |
| HoxH | NP_942730.1 | 38637756 | *Ralstonia eutropha* H16 |
| HoxW | NP_942731.1 | 38637757 | *Ralstonia eutropha* H16 |
| HoxI | NP_942732.1 | 38637758 | *Ralstonia eutropha* H16 |
| HoxE | NP_953767.1 | 39997816 | *Geobacter sulfurreducens* |
| HoxF | NP_953766.1 | 39997815 | *Geobacter sulfurreducens* |
| HoxU | NP_953765.1 | 39997814 | *Geobacter sulfurreducens* |
| HoxY | NP_953764.1 | 39997813 | *Geobacter sulfurreducens* |
| HoxH | NP_953763.1 | 39997812 | *Geobacter sulfurreducens* |
| GSU2717 | NP_953762.1 | 39997811 | *Geobacter sulfurreducens* |
| HoxE | NP_441418.1 | 16330690 | *Synechocystis* str. PCC 6803 |
| HoxF | NP_441417.1 | 16330689 | *Synechocystis* str. PCC 6803 |
| Unknown function | NP_441416.1 | 16330688 | *Synechocystis* str. PCC 6803 |
| HoxU | NP_441415.1 | 16330687 | *Synechocystis* str. PCC 6803 |
| HoxY | NP_441414.1 | 16330686 | *Synechocystis* str. PCC 6803 |
| Unknown function | NP_441413.1 | 16330685 | *Synechocystis* str. PCC 6803 |
| Unknown function | NP_441412.1 | 16330684 | *Synechocystis* str. PCC 6803 |
| HoxH | NP_441411.1 | 16330683 | *Synechocystis* str. PCC 6803 |
| HypF | NP_484737.1 | 17228189 | *Nostoc* sp. PCC 7120 |
| HypC | NP_484738.1 | 17228190 | *Nostoc* sp. PCC 7120 |
| HypD | NP_484739.1 | 17228191 | *Nostoc* sp. PCC 7120 |
| Unknown function | NP_484740.1 | 17228192 | *Nostoc* sp. PCC 7120 |
| HypE | NP_484741.1 | 17228193 | *Nostoc* sp. PCC 7120 |
| HypA | NP_484742.1 | 17228194 | *Nostoc* sp. PCC 7120 |
| HypB | NP_484743.1 | 17228195 | *Nostoc* sp. PCC 7120 |
| Hox1E | AAP50519.1 | 37787351 | *Thiocapsa roseopersicina* |
| Hox1F | AAP50520.1 | 37787352 | *Thiocapsa roseopersicina* |
| Hox1U | AAP50521.1 | 37787353 | *Thiocapsa roseopersicina* |
| Hox1Y | AAP50522.1 | 37787354 | *Thiocapsa roseopersicina* |
| Hox1H | AAP50523.1 | 37787355 | *Thiocapsa roseopersicina* |

The genomes of *E. coli* and other enteric bacteria encode up to four hydrogenase enzymes (Sawers, G., *Antonie Van Leeuwenhoek* 66:57-88 (1994); Sawers et al., *J Bacteria* 164:1324-1331 (1985); Sawers and Boxer, *Eur. J Biochem.* 156:265-275 (1986); Sawers et al., *J. Bacteriol.* 168:398-404 (1986)). Given the multiplicity of enzyme activities *E. coli* or another host organism can provide sufficient hydrogenase activity to split incoming molecular hydrogen and reduce the corresponding acceptor. Endogenous hydrogen-lyase enzymes of *E. coli* include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. Hydrogenase activity in *E. coli* is also dependent upon the expression of the hyp genes whose corresponding proteins are involved in the assembly of the hydrogenase complexes (Jacobi et al., *Arch. Microbiol* 158: 444-451 (1992); Rangarajan et al., *J Bacteria* 190:1447-1458 (2008)). The *M. thermoacetica* and *Clostridium ljungdahii* hydrogenases are suitable for a host that lacks sufficient endogenous hydrogenase activity. *M. thermoacetica* and *C. ljungdahli* can grow with $CO_2$ as the exclusive carbon source indicating that reducing equivalents are extracted from $H_2$ to enable acetyl-CoA synthesis via the Wood-Ljungdahl pathway (Drake, H. L., *J Bacteriol.* 150: 702-709 (1982); Drake and Daniel, *Res Microbiol* 155:869-883 (2004); Kellum and Drake, *J Bacteriol.* 160:466-469 (1984)). *M. thermoacetica* has homologs to several hyp, hyc, and hyf genes from *E. coli*. These protein sequences encoded for by these genes are identified by the following GenBank accession numbers. In addition, several gene clusters encoding hydrogenase functionality are present in *M. thermoacetica* and *C. ljungdahli* (see for example US 2012/0003652).

| Protein | GenBank ID | GI Number | Organism |
|---|---|---|---|
| HypA | NP_417206 | 16130633 | *Escherichia coli* |
| HypB | NP_417207 | 16130634 | *Escherichia coli* |
| HypC | NP_417208 | 16130635 | *Escherichia coli* |
| HypD | NP_417209 | 16130636 | *Escherichia coli* |
| HypE | NP_417210 | 226524740 | *Escherichia coli* |
| HypF | NP_417192 | 16130619 | *Escherichia coli* |
| HycA | NP_417205 | 16130632 | *Escherichia coli* |
| HycB | NP_417204 | 16130631 | *Escherichia coli* |
| HycC | NP_417203 | 16130630 | *Escherichia coli* |
| HycD | NP_417202 | 16130629 | *Escherichia coli* |
| HycE | NP_417201 | 16130628 | *Escherichia coli* |
| HycF | NP_417200 | 16130627 | *Escherichia coli* |
| HycG | NP_417199 | 16130626 | *Escherichia coli* |
| HycH | NP_417198 | 16130625 | *Escherichia coli* |
| HycI | NP_417197 | 16130624 | *Escherichia coli* |
| HyfA | NP_416976 | 90111444 | *Escherichia coli* |
| HyfB | NP_416977 | 16130407 | *Escherichia coli* |
| HyfC | NP_416978 | 90111445 | *Escherichia coli* |
| HyfD | NP_416979 | 16130409 | *Escherichia coli* |
| HyfE | NP_416980 | 16130410 | *Escherichia coli* |
| HyfF | NP_416981 | 16130411 | *Escherichia coli* |
| HyfG | NP_416982 | 16130412 | *Escherichia coli* |
| HyfH | NP_416983 | 16130413 | *Escherichia coli* |
| HyfI | NP_416984 | 16130414 | *Escherichia coli* |
| HyfJ | NP_416985 | 90111446 | *Escherichia coli* |
| HyfR | NP_416986 | 90111447 | *Escherichia coli* |

Proteins in *M. thermoacetica* whose genes are homologous to the *E. coli* hydrogenase genes are shown below.

| Protein | GenBank ID | GI Number | Organism |
|---|---|---|---|
| Moth_2175 | YP_431007 | 83590998 | *Moorella thermoacetica* |
| Moth_2176 | YP_431008 | 83590999 | *Moorella thermoacetica* |
| Moth_2177 | YP_431009 | 83591000 | *Moorella thermoacetica* |
| Moth_2178 | YP_431010 | 83591001 | *Moorella thermoacetica* |
| Moth_2179 | YP_431011 | 83591002 | *Moorella thermoacetica* |
| Moth_2180 | YP_431012 | 83591003 | *Moorella thermoacetica* |
| Moth_2181 | YP_431013 | 83591004 | *Moorella thermoacetica* |
| Moth_2182 | YP_431014 | 83591005 | *Moorella thermoacetica* |
| Moth_2183 | YP_431015 | 83591006 | *Moorella thermoacetica* |
| Moth_2184 | YP_431016 | 83591007 | *Moorella thermoacetica* |
| Moth_2185 | YP_431017 | 83591008 | *Moorella thermoacetica* |
| Moth_2186 | YP_431018 | 83591009 | *Moorella thermoacetica* |
| Moth_2187 | YP_431019 | 83591010 | *Moorella thermoacetica* |
| Moth_2188 | YP_431020 | 83591011 | *Moorella thermoacetica* |
| Moth_2189 | YP_431021 | 83591012 | *Moorella thermoacetica* |
| Moth_2190 | YP_431022 | 83591013 | *Moorella thermoacetica* |
| Moth_2191 | YP_431023 | 83591014 | *Moorella thermoacetica* |
| Moth_2192 | YP_431024 | 83591015 | *Moorella thermoacetica* |
| Moth_0439 | YP_429313 | 83589304 | *Moorella thermoacetica* |
| Moth_0440 | YP_429314 | 83589305 | *Moorella thermoacetica* |
| Moth_0441 | YP_429315 | 83589306 | *Moorella thermoacetica* |
| Moth_0442 | YP_429316 | 83589307 | *Moorella thermoacetica* |
| Moth_0809 | YP_429670 | 83589661 | *Moorella thermoacetica* |
| Moth_0810 | YP_429671 | 83589662 | *Moorella thermoacetica* |
| Moth_0811 | YP_429672 | 83589663 | *Moorella thermoacetica* |
| Moth_0812 | YP_429673 | 83589664 | *Moorella thermoacetica* |
| Moth_0814 | YP_429674 | 83589665 | *Moorella thermoacetica* |
| Moth_0815 | YP_429675 | 83589666 | *Moorella thermoacetica* |
| Moth_0816 | YP_429676 | 83589667 | *Moorella thermoacetica* |
| Moth_1193 | YP_430050 | 83590041 | *Moorella thermoacetica* |
| Moth_1194 | YP_430051 | 83590042 | *Moorella thermoacetica* |
| Moth_1195 | YP_430052 | 83590043 | *Moorella thermoacetica* |
| Moth_1196 | YP_430053 | 83590044 | *Moorella thermoacetica* |
| Moth_1717 | YP_430562 | 83590553 | *Moorella thermoacetica* |
| Moth_1718 | YP_430563 | 83590554 | *Moorella thermoacetica* |
| Moth_1719 | YP_430564 | 83590555 | *Moorella thermoacetica* |
| Moth_1883 | YP_430726 | 83590717 | *Moorella thermoacetica* |
| Moth_1884 | YP_430727 | 83590718 | *Moorella thermoacetica* |
| Moth_1885 | YP_430728 | 83590719 | *Moorella thermoacetica* |
| Moth_1886 | YP_430729 | 83590720 | *Moorella thermoacetica* |
| Moth_1887 | YP_430730 | 83590721 | *Moorella thermoacetica* |
| Moth_1888 | YP_430731 | 83590722 | *Moorella thermoacetica* |
| Moth_1452 | YP_430305 | 83590296 | *Moorella thermoacetica* |
| Moth_1453 | YP_430306 | 83590297 | *Moorella thermoacetica* |
| Moth_1454 | YP_430307 | 83590298 | *Moorella thermoacetica* |

Genes encoding hydrogenase enzymes from *C. ljungdahli* are shown below.

| Protein | GenBank ID | GI Number | Organism |
|---|---|---|---|
| CLJU_c20290 | ADK15091.1 | 300435324 | *Clostridium ljungdahli* |
| CLJU_c07030 | ADK13773.1 | 300434006 | *Clostridium ljungdahli* |
| CLJU_c07040 | ADK13774.1 | 300434007 | *Clostridium ljungdahli* |
| CLJU_c07050 | ADK13775.1 | 300434008 | *Clostridium ljungdahli* |
| CLJU_c07060 | ADK13776.1 | 300434009 | *Clostridium ljungdahli* |
| CLJU_c07070 | ADK13777.1 | 300434010 | *Clostridium ljungdahli* |
| CLJU_c07080 | ADK13778.1 | 300434011 | *Clostridium ljungdahli* |
| CLJU_c14730 | ADK14541.1 | 300434774 | *Clostridium ljungdahli* |
| CLJU_c14720 | ADK14540.1 | 300434773 | *Clostridium ljungdahli* |
| CLJU_c14710 | ADK14539.1 | 300434772 | *Clostridium ljungdahli* |
| CLJU_c14700 | ADK14538.1 | 300434771 | *Clostridium ljungdahli* |
| CLJU_c28670 | ADK15915.1 | 300436148 | *Clostridium ljungdahli* |
| CLJU_c28660 | ADK15914.1 | 300436147 | *Clostridium ljungdahli* |
| CLJU_c28650 | ADK15913.1 | 300436146 | *Clostridium ljungdahli* |
| CLJU_c28640 | ADK15912.1 | 300436145 | *Clostridium ljungdahli* |

In some cases, hydrogenase encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J Bacteria* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J Am. Chem. Soc.* 129:10328-10329 (2007)).

| Protein | GenBank ID | GI Number | Organism |
|---|---|---|---|
| CooL | AAC45118 | 1515468 | *Rhodospirillum rubrum* |
| CooX | AAC45119 | 1515469 | *Rhodospirillum rubrum* |
| CooU | AAC45120 | 1515470 | *Rhodospirillum rubrum* |
| CooH | AAC45121 | 1498746 | *Rhodospirillum rubrum* |
| CooF | AAC45122 | 1498747 | *Rhodospirillum rubrum* |
| CODH (CooS) | AAC45123 | 1498748 | *Rhodospirillum rubrum* |
| CooC | AAC45124 | 1498749 | *Rhodospirillum rubrum* |
| CooT | AAC45125 | 1498750 | *Rhodospirillum rubrum* |
| CooJ | AAC45126 | 1498751 | *Rhodospirillum rubrum* |
| CODH-I (CooS-I) | YP_360644 | 78043418 | *Carboxydothermus hydrogenoformans* |
| CooF | YP_360645 | 78044791 | *Carboxydothermus hydrogenoformans* |
| HypA | YP_360646 | 78044340 | *Carboxydothermus hydrogenoformans* |
| CooH | YP_360647 | 78043871 | *Carboxydothermus hydrogenoformans* |
| CooU | YP_360648 | 78044023 | *Carboxydothermus hydrogenoformans* |
| CooX | YP_360649 | 78043124 | *Carboxydothermus hydrogenoformans* |

-continued

| Protein | GenBank ID | GI Number | Organism |
|---|---|---|---|
| CooL | YP_360650 | 78043938 | Carboxydothermus hydrogenoformans |
| CooK | YP_360651 | 78044700 | Carboxydothermus hydrogenoformans |
| CooM | YP_360652 | 78043942 | Carboxydothermus hydrogenoformans |
| CooC | YP_360654.1 | 78043296 | Carboxydothermus hydrogenoformans |
| CooA-1 | YP_360655.1 | 78044021 | Carboxydothermus hydrogenoformans |

Some hydrogenase and CODH enzymes transfer electrons to ferredoxins. Ferredoxins are small acidic proteins containing one or more iron-sulfur clusters that function as intracellular electron carriers with a low reduction potential. Reduced ferredoxins donate electrons to Fe-dependent enzymes such as ferredoxin-NADP$^+$ oxidoreductase, pyruvate:ferredoxin oxidoreductase (PFOR) and 2-oxoglutarate:ferredoxin oxidoreductase (OFOR). The *H. thermophiles* gene fdx1 encodes a [4Fe-4S]-type ferredoxin that is required for the reversible carboxylation of 2-oxoglutarate and pyruvate by OFOR and PFOR, respectively (Yamamoto et al., *Extremophiles* 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 93% homology with the zfx ferredoxin from *S. acidocaldarius*. The *E. coli* genome encodes a soluble ferredoxin of unknown physiological function, fdx. Some evidence indicates that this protein can function in iron-sulfur cluster assembly (Takahashi and Nakamura, 1999). Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella thermoacetica, Clostridium carboxidivorans* P7, *Clostridium ljungdahli* and *Rhodospirillum rubrum* are predicted to encode several ferredoxins, listed below.

| Protein | GenBank ID | GI Number | Organism |
|---|---|---|---|
| fdx1 | BAE02673.1 | 68163284 | Hydrogenobacter thermophilus |
| M11214.1 | AAA83524.1 | 144806 | Clostridium pasteurianum |
| Zfx | AAY79867.1 | 68566938 | Sulfolobus acidocalarius |
| Fdx | AAC75578.1 | 1788874 | Escherichia coli |
| hp_0277 | AAD07340.1 | 2313367 | Helicobacter pylori |
| fdxA | CAL34484.1 | 112359698 | Campylobacter jejuni |
| Moth_0061 | ABC18400.1 | 83571848 | Moorella thermoacetica |
| Moth_1200 | ABC19514.1 | 83572962 | Moorella thermoacetica |
| Moth_1888 | ABC20188.1 | 83573636 | Moorella thermoacetica |
| Moth_2112 | ABC20404.1 | 83573852 | Moorella thermoacetica |
| Moth_1037 | ABC19351.1 | 83572799 | Moorella thermoacetica |
| CcarbDRAFT_4383 | ZP_05394383.1 | 255527515 | Clostridium carboxidivorans P7 |
| CcarbDRAFT_2958 | ZP_05392958.1 | 255526034 | Clostridium carboxidivorans P7 |
| CcarbDRAFT_2281 | ZP_05392281.1 | 255525342 | Clostridium carboxidivorans P7 |
| CcarbDRAFT_5296 | ZP_05395295.1 | 255528511 | Clostridium carboxidivorans P7 |
| CcarbDRAFT_1615 | ZP_05391615.1 | 255524662 | Clostridium carboxidivorans P7 |
| CcarbDRAFT_1304 | ZP_05391304.1 | 255524347 | Clostridium carboxidivorans P7 |
| cooF | AAG29808.1 | 11095245 | Carboxydothermus hydrogenoformans |
| fdxN | CAA35699.1 | 46143 | Rhodobacter capsulatus |
| Rru_A2264 | ABC23064.1 | 83576513 | Rhodospirillum rubrum |
| Rru_A1916 | ABC22716.1 | 83576165 | Rhodospirillum rubrum |
| Rru_A2026 | ABC22826.1 | 83576275 | Rhodospirillum rubrum |
| cooF | AAC45122.1 | 1498747 | Rhodospirillum rubrum |
| fdxN | AAA26460.1 | 152605 | Rhodospirillum rubrum |
| Alvin_2884 | ADC63789.1 | 288897953 | Allochromatium vinosum DSM 180 |
| Fdx | YP_002801146.1 | 226946073 | Azotobacter vinelandii DJ |
| CKL_3790 | YP_001397146.1 | 153956381 | Clostridium kluyveri DSM 555 |
| fer1 | NP_949965.1 | 39937689 | Rhodopseudomonas palustris CGA009 |
| Fdx | CAA12251.1 | 3724172 | Thauera aromatica |
| CHY_2405 | YP_361202.1 | 78044690 | Carboxydothermus hydrogenoformans |
| Fer | YP_359966.1 | 78045103 | Carboxydothermus hydrogenoformans |
| Fer | AAC83945.1 | 1146198 | Bacillus subtilis |
| fdx1 | NP_249053.1 | 15595559 | Pseudomonas aeruginosa PA01 |
| yfhL | AP_003148.1 | 89109368 | Escherichia coli K-12 |
| CLJU_c00930 | ADK13195.1 | 300433428 | Clostridium ljungdahli |
| CLJU_c00010 | ADK13115.1 | 300433348 | Clostridium ljungdahli |
| CLJU_c01820 | ADK13272.1 | 300433505 | Clostridium ljungdahli |
| CLJU_c17980 | ADK14861.1 | 300435094 | Clostridium ljungdahli |
| CLJU_c17970 | ADK14860.1 | 300435093 | Clostridium ljungdahli |
| CLJU_c22510 | ADK15311.1 | 300435544 | Clostridium ljungdahli |
| CLJU_c26680 | ADK15726.1 | 300435959 | Clostridium ljungdahli |
| CLJU_c29400 | ADK15988.1 | 300436221 | Clostridium ljungdahli |

Ferredoxin oxidoreductase enzymes transfer electrons from ferredoxins or flavodoxins to NAD(P)H. Two enzymes catalyzing the reversible transfer of electrons from reduced ferredoxins to NAD(P)+ are ferredoxin:NAD+ oxidoreductase (EC 1.18.1.3) and ferredoxin:NADP+ oxidoreductase (FNR, EC 1.18.1.2). Ferredoxin:NADP+ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., *Eur. J. Biochem.* 123:563-569 (1982); Fujii et al., 1977). The *Helicobacter pylori* FNR, encoded by HP1164 (fqrB), is coupled to the activity of pyruvate:ferredoxin oxidoreductase (PFOR) resulting in the pyruvate-dependent production of NADPH (St et al. 2007). An analogous enzyme is found in *Campylobacter jejuni* (St Maurice et al., *J. Bacteriol.* 189:4764-4773 (2007)). A ferredoxin:NADP+ oxidoreductase enzyme is encoded in the *E. coli* genome by fpr (Bianchi et al. 1993). Ferredoxin:NAD+ oxidoreductase utilizes reduced ferredoxin to generate NADH from NAD+. In several organisms, including *E. coli*, this enzyme is a component of multifunctional dioxygenase enzyme complexes. The ferredoxin:NAD+ oxidoreductase of *E. coli*, encoded by hcaD, is a component of the 3-phenylproppionate dioxygenase system involved in involved in aromatic acid utilization (Diaz et al. 1998). NADH:ferredoxin reductase activity was detected in cell extracts of *Hydrogenobacter thermophilus*, although a gene with this activity has not yet been indicated (Yoon et al. 2006). Additional ferredoxin:NAD(P)+ oxidoreductases have been annotated in *Clostridium carboxydivorans* P7. The NADH-dependent reduced ferredoxin: NADP oxidoreductase of *C. kluyveri*, encoded by nfnAB, catalyzes the concomitant reduction of ferredoxin and NAD+ with two equivalents of NADPH (Wang et al, *J Bacteriol* 192: 5115-5123 (2010)). Finally, the energy-conserving membrane-associated Rnf-type proteins (Seedorf et al, *PNAS* 105:2128-2133 (2008); and Herrmann, *J. Bacteriol* 190:784-791 (2008)) provide a means to generate NADH or NADPH from reduced ferredoxin.

FIG. 1, Step I—Formate Dehydrogenase

Formate dehydrogenase (FDH) catalyzes the reversible transfer of electrons from formate to an acceptor. Enzymes with FDH activity utilize various electron carriers such as, for example, NADH (EC 1.2.1.2), NADPH (EC 1.2.1.43), quinols (EC 1.1.5.6), cytochromes (EC 1.2.2.3) and hydrogenases (EC 1.1.99.33). FDH enzymes have been characterized from *Morella thermoacetica* (Andreesen and Ljungdahl, *J Bacteriol* 116:867-873 (1973); Li et al., *J Bacteriol* 92:405-412 (1966); Yamamoto et al., *J Biol. Chem.* 258: 1826-1832 (1983). The loci, Moth_2312 is responsible for encoding the alpha subunit of formate dehydrogenase while the beta subunit is encoded by Moth_2314 (Pierce et al., *Environ Microbiol* (2008)). Another set of genes encoding formate dehydrogenase activity with a propensity for $CO_2$ reduction is encoded by Sfum_2703 through Sfum_2706 in *Syntrophobacter fumaroxidans* (de Bok et al., *Eur. J. Biochem.* 270:2476-2485 (2003)); Reda et al., *PNAS* 105: 10654-10658 (2008)). A similar set of genes presumed to carry out the same function are encoded by CHY_0731, CHY_0732, and CHY_0733 in *C. hydrogenoformans* (Wu et al., *PLoS Genet.* 1:e65 (2005)). Formate dehydrogenases are also found many additional organisms including *C. carboxidivorans* P7, *Bacillus methanolicus*, *Burkholderia stabilis*, *Moorella thermoacetica* ATCC 39073, *Candida boidinii*, *Candida methylica*, and *Saccharomyces cerevisiae* S288c. The soluble formate dehydrogenase from *Ralstonia eutropha* reduces $NAD^+$ (fdsG, -B, -A, -C, -D) (Oh and Bowien, 1998)

| Protein | GenBank ID | GI Number | Organism |
| --- | --- | --- | --- |
| fqrB | NP_207955.1 | 15645778 | *Helicobacter pylori* |
| fqrB | YP_001482096.1 | 157414840 | *Campylobacter jejuni* |
| RPA3954 | CAE29395.1 | 39650872 | *Rhodopseudomonas palustris* |
| Fpr | BAH29712.1 | 225320633 | *Hydrogenobacter thermophilus* |
| yumC | NP_391091.2 | 255767736 | *Bacillus subtilis* |
| Fpr | P28861.4 | 399486 | *Escherichia coli* |
| hcaD | AAC75595.1 | 1788892 | *Escherichia coli* |
| LOC100282643 | NP_001149023.1 | 226497434 | *Zea mays* |
| NfnA | YP_001393861.1 | 153953096 | *Clostridium kluyveri* |
| NfnB | YP_001393862.1 | 153953097 | *Clostridium kluyveri* |
| CcarbDRAFT_2639 | ZP_05392639.1 | 255525707 | *Clostridium carboxidivorans* P7 |
| CcarbDRAFT_2638 | ZP_05392638.1 | 255525706 | *Clostridium carboxidivorans* P7 |
| CcarbDRAFT_2636 | ZP_05392636.1 | 255525704 | *Clostridium carboxidivorans* P7 |
| CcarbDRAFT_5060 | ZP_05395060.1 | 255528241 | *Clostridium carboxidivorans* P7 |
| CcarbDRAFT_2450 | ZP_05392450.1 | 255525514 | *Clostridium carboxidivorans* P7 |
| CcarbDRAFT_1084 | ZP_05391084.1 | 255524124 | *Clostridium carboxidivorans* P7 |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |
| CLJU_c11410 (RnfB) | ADK14209.1 | 300434442 | *Clostridium ljungdahlii* |
| CLJU_c11400 (RnfA) | ADK14208.1 | 300434441 | *Clostridium ljungdahlii* |
| CLJU_c11390 (RnfE) | ADK14207.1 | 300434440 | *Clostridium ljungdahlii* |
| CLJU_c11380 (RnfG) | ADK14206.1 | 300434439 | *Clostridium ljungdahlii* |
| CLJU_c11370 (RnfD) | ADK14205.1 | 300434438 | *Clostridium ljungdahlii* |
| CLJU_c11360 (RnfC) | ADK14204.1 | 300434437 | *Clostridium ljungdahlii* |
| MOTH_1518 (NfnA) | YP_430370.1 | 83590361 | *Moorella thermoacetica* |
| MOTH_1517 (NfnB) | YP_430369.1 | 83590360 | *Moorella thermoacetica* |
| CHY_1992 (NfnA) | YP_360811.1 | 78045020 | *Carboxydothermus hydrogenoformans* |
| CHY_1993 (NfnB) | YP_360812.1 | 78044266 | *Carboxydothermus hydrogenoformans* |
| CLJU_c37220 (NfnAB) | YP_003781850.1 | 300856866 | *Clostridium ljungdahlii* |

| Protein | GenBank ID | GI Number | Organism |
|---|---|---|---|
| Moth_2312 | YP_431142 | 148283121 | Moorella thermoacetica |
| Moth_2314 | YP_431144 | 83591135 | Moorella thermoacetica |
| Sfum_2703 | YP_846816.1 | 116750129 | Syntrophobacter fumaroxidans |
| Sfum_2704 | YP_846817.1 | 116750130 | Syntrophobacter fumaroxidans |
| Sfum_2705 | YP_846818.1 | 116750131 | Syntrophobacter fumaroxidans |
| Sfum_2706 | YP_846819.1 | 116750132 | Syntrophobacter fumaroxidans |
| CHY_0731 | YP_359585.1 | 78044572 | Carboxydothermus hydrogenoformans |
| CHY_0732 | YP_359586.1 | 78044500 | Carboxydothermus hydrogenoformans |
| CHY_0733 | YP_359587.1 | 78044647 | Carboxydothermus hydrogenoformans |
| CcarbDRAFT_0901 | ZP_05390901.1 | 255523938 | Clostridium carboxidivorans P7 |
| CcarbDRAFT_4380 | ZP_05394380.1 | 255527512 | Clostridium carboxidivorans P7 |
| fdhA, MGA3_06625 | EIJ82879.1 | 387590560 | Bacillus methanolicus MGA3 |
| fdhA, PB1_11719 | ZP_10131761.1 | 387929084 | Bacillus methanolicus PB1 |
| fdhD, MGA3_06630 | EIJ82880.1 | 387590561 | Bacillus methanolicus MGA3 |
| fdhD, PB1_11724 | ZP_10131762.1 | 387929085 | Bacillus methanolicus PB1 |
| fdh | ACF35003. | 194220249 | Burkholderia stabilis |
| FDH1 | AAC49766.1 | 2276465 | Candida boidinii |
| Fdh | CAA57036.1 | 1181204 | Candida methylica |
| FDH2 | P0CF35.1 | 294956522 | Saccharomyces cerevisiae S288c |
| FDH1 | NP_015033.1 | 6324964 | Saccharomyces cerevisiae S288c |

FIG. 1, Step J—Methanol Dehydrogenase

NAD+ dependent methanol dehydrogenase enzymes (EC 1.1.1.244) catalyze the conversion of methanol and NAD+ to formaldehyde and NADH. An enzyme with this activity was first characterized in Bacillus methanolicus (Heggeset, et al., Applied and Environmental Microbiology, 78(15): 5170-5181 (2012)). This enzyme is zinc and magnesium dependent, and activity of the enzyme is enhanced by the activating enzyme encoded by act (Kloosterman et al, J Biol Chem 277:34785-92 (2002)). Additional NAD(P)+ dependent enzymes can be identified by sequence homology. Methanol dehydrogenase enzymes utilizing different electron acceptors are also known in the art. Examples include cytochrome dependent enzymes such as mxaIF of the methylotroph Methylobacterium extorquens (Nunn et al, Nucl Acid Res 16:7722 (1988)). Methanol dehydrogenase enzymes of methanotrophs such as Methylococcus capsulatis function in a complex with methane monooxygenase (MMO) (Myronova et al, Biochem 45:11905-14 (2006)). Methanol can also be oxidized to formaldehyde by alcohol oxidase enzymes such as methanol oxidase (EC 1.1.3.13) of Candida boidinii (Sakai et al, Gene 114: 67-73 (1992)).

| Protein | GenBank ID | GI Number | Organism |
|---|---|---|---|
| mdh, MGA3_17392 | EIJ77596.1 | 387585261 | Bacillus methanolicus MGA3 |
| mdh2, MGA3_07340 | EIJ83020.1 | 387590701 | Bacillus methanolicus MGA3 |
| mdh3, MGA3_10725 | EIJ80770.1 | 387588449 | Bacillus methanolicus MGA3 |
| act, MGA3_09170 | EIJ83380.1 | 387591061 | Bacillus methanolicus MGA3 |
| mdh, PB1_17533 | ZP_10132907.1 | 387930234 | Bacillus methanolicus PB1 |
| mdh1, PB1_14569 | ZP_10132325.1 | 387929648 | Bacillus methanolicus PB1 |
| mdh2, PB1_12584 | ZP_10131932.1 | 387929255 | Bacillus methanolicus PB1 |
| act, PB1_14394 | ZP_10132290.1 | 387929613 | Bacillus methanolicus PB1 |
| BFZC1_05383 | ZP_07048751.1 | 299535429 | Lysinibacillus fusiformis |
| BFZC1_20163 | ZP_07051637.1 | 299538354 | Lysinibacillus fusiformis |
| Bsph_4187 | YP_001699778.1 | 169829620 | Lysinibacillus sphaericus |
| Bsph_1706 | YP_001697432.1 | 169827274 | Lysinibacillus sphaericus |
| MCA0299 | YP_112833.1 | 53802410 | Methylococcus capsulatis |
| MCA0782 | YP_113284.1 | 53804880 | Methylococcus capsulatis |
| mxaI | YP_002965443.1 | 240140963 | Methylobacterium extorquens |
| mxaF | YP_002965446.1 | 240140966 | Methylobacterium extorquens |
| AOD1 | AAA34321.1 | 170820 | Candida boidinii |

FIG. 1, Step K—Spontaneous or Formaldehyde Activating Enzyme

The conversion of formaldehyde and THF to methylenetetrahydrofolate can occur spontaneously. It is also possible that the rate of this reaction can be enhanced by a formaldehyde activating enzyme. A formaldehyde activating enzyme (Fae) has been identified in Methylobacterium extorquens AM1 which catalyzes the condensation of formaldehyde and tetrahydromethanopterin to methylene tetrahydromethanopterin (Vorholt, et al., J. Bacteriol., 182(23), 6645-6650 (2000)). It is possible that a similar enzyme exists or can be engineered to catalyze the condensation of formaldehyde and tetrahydrofolate to methylenetetrahydrofolate. Homologs exist in several organisms including Xanthobacter autotrophicus Py2 and Hyphomicrobium denitrificans ATCC 51888.

| Protein | GenBank ID | GI Number | Organism |
|---|---|---|---|
| MexAM1_META1p1766 | Q9FA38.3 | 17366061 | Methylobacterium extorquens AM1 |
| Xaut_0032 | YP_001414948.1 | 154243990 | Xanthobacter autotrophicus Py2 |
| Hden_1474 | YP_003755607.1 | 300022996 | Hyphomicrobium denitrificans ATCC 51888 |

FIG. 1, Step L—Formaldehyde Dehydrogenase

Oxidation of formaldehyde to formate is catalyzed by formaldehyde dehydrogenase. An NAD+ dependent formaldehyde dehydrogenase enzyme is encoded by fdhA of *Pseudomonas putida* (Ito et al, *J Bacteriol* 176: 2483-2491 (1994)). Additional formaldehyde dehydrogenase enzymes include the NAD+ and glutathione independent formaldehyde dehydrogenase from *Hyphomicrobium zavarzinii* (Jerome et al, Appl Microbiol Biotechnol 77:779-88 (2007)), the glutathione dependent formaldehyde dehydrogenase of *Pichia pastoris* (Sunga et al, Gene 330:39-47 (2004)) and the NAD(P)+ dependent formaldehyde dehydrogenase of *Methylobacter marinus* (Speer et al, FEMS Microbiol Lett, 121(3):349-55 (1994)).

| Protein | GenBank ID | GI Number | Organism |
|---|---|---|---|
| fdhA | P46154.3 | 1169603 | *Pseudomonas putida* |
| faoA | CAC85637.1 | 19912992 | *Hyphomicrobium zavarzinii* |
| Fld1 | CCA39112.1 | 328352714 | *Pichia pastoris* |
| Fdh | P47734.2 | 221222447 | *Methylobacter marinus* |

In addition to the formaldehyde dehydrogenase enzymes listed above, alternate enzymes and pathways for converting formaldehyde to formate are known in the art. For example, many organisms employ glutathione-dependent formaldehyde oxidation pathways, in which formaldehyde is converted to formate in three steps via the intermediates S-hydroxymethylglutathione and S-formylglutathione (Vorholt et al, *J Bacteriol* 182:6645-50 (2000)). The enzymes of this pathway are S-(hydroxymethyl)glutathione synthase (EC 4.4.1.22), glutathione-dependent formaldehyde dehydrogenase (EC 1.1.1.284) and S-formylglutathione hydrolase (EC 3.1.2.12).

FIG. 1, Step M—Spontaneous or S-(hydroxymethyl)glutathione Synthase

While conversion of formaldehyde to S-hydroxymethylglutathione can occur spontaneously in the presence of glutathione, it has been shown by Goenrich et al (Goenrich, et al., J Biol Chem 277(5); 3069-72 (2002)) that an enzyme from *Paracoccus denitrificans* can accelerate this spontaneous condensation reaction. The enzyme catalyzing the conversion of formaldehyde and glutathione was purified and named glutathione-dependent formaldehyde-activating enzyme (Gfa). The gene encoding it, which was named gfa, is located directly upstream of the gene for glutathione-dependent formaldehyde dehydrogenase, which catalyzes the subsequent oxidation of S-hydroxymethylglutathione. Putative proteins with sequence identity to Gfa from *P. denitrificans* are present also in *Rhodobacter sphaeroides*, *Sinorhizobium meliloti*, and *Mesorhizobium loti*.

| Protein | GenBank ID | GI Number | Organism |
|---|---|---|---|
| Gfa | Q51669.3 | 38257308 | *Paracoccus denitrificans* |
| Gfa | ABP71667.1 | 145557054 | *Rhodobacter sphaeroides* ATCC 17025 |
| Gfa | Q92WX6.1 | 38257348 | *Sinorhizobium meliloti* 1021 |
| Gfa | Q98LU4.2 | 38257349 | *Mesorhizobium loti* MAFF303099 |

FIG. 1, Step N—Glutathione-Dependent Formaldehyde Dehydrogenase

Glutathione-dependent formaldehyde dehydrogenase (GS-FDH) belongs to the family of class III alcohol dehydrogenases. Glutathione and formaldehyde combine non-enzymatically to form hydroxymethylglutathione, the true substrate of the GS-FDH catalyzed reaction. The product, S-formylglutathione, is further metabolized to formic acid.

| Protein | GenBank ID | GI Number | Organism |
|---|---|---|---|
| frmA | YP_488650.1 | 388476464 | *Escherichia coli* K-12 MG1655 |
| SFA1 | NP_010113.1 | 6320033 | *Saccharomyces cerevisiae* S288c |
| flhA | AAC44551.1 | 1002865 | *Paracoccus denitrificans* |
| adhI | AAB09774.1 | 986949 | *Rhodobacter sphaeroides* |

FIG. 1, Step O—S-Formylglutathione Hydrolase

S-formylglutathione hydrolase is a glutathione thiol esterase found in bacteria, plants and animals. It catalyzes conversion of S-formylglutathione to formate and glutathione. The fghA gene of *P. denitrificans* is located in the same operon with gfa and flhA, two genes involved in the oxidation of formaldehyde to formate in this organism. In *E. coli*, FrmB is encoded in an operon with FrmR and FrmA, which are proteins involved in the oxidation of formaldehyde. YeiG of *E. coli* is a promiscuous serine hydrolase; its highest specific activity is with the substrate S-formylglutathione.

| Protein | GenBank ID | GI Number | Organism |
|---|---|---|---|
| frmB | NP_414889.1 | 16128340 | *Escherichia coli* K-12 MG1655 |
| yeiG | AAC75215.1 | 1788477 | *Escherichia coli* K-12 MG1655 |
| fghA | AAC44554.1 | 1002868 | *Paracoccus denitrificans* |

4.2 Example II

Enhanced Yield of Succinate from Carbohydrates Using Methanol

Exemplary methanol metabolic pathways for enhancing the availability of reducing equivalents are provided in FIG. 1.

Succinate production can be achieved in a recombinant organism by the pathway shown in FIG. 2. For example, pathways for the production of succinate from glucose, $CO_2$, and reducing equivalents (e.g., MeOH) at a theoretical yield of 2.0 mol succinate/mol glucose are provided. Exemplary enzymes for the conversion of glucose to succinate by this route include. 2A) a phosphoenolpyruvate (PEP) carboxylase or a PEP carboxykinase; 2B) a pyruvate carboxylase; 2C) a malate dehydrogenase; 2D) a malic enzyme; 2E) a fumarase; and 2F) a fumarate reductase. Succinate production can be carried out by 2A, 2C, 2E and 2F; 2B, 2C, 2E and 2F; or 2D, 2E and 2F. Oxidative TCA cycle enzymes and enzymes for the conversion of phosphoenolpyruvate to acetyl-CoA are not required to produce succinate at the theoretical yield in this example. Note that several other carbohydrates can be converted to phosphoenolpyruvate and succinate by this simplified route including xylose, arabinose, galactose, and glycerol.

FIG. 2, Step A—PEP Carboxylase or PEP Carboxykinase

Carboxylation of phosphoenolpyruvate to oxaloacetate is catalyzed by phosphoenolpyruvate carboxylase. Exemplary PEP carboxylase enzymes are encoded by ppc in *E. coli* (Kai et al., *Arch. Biochem. Biophys.* 414:170-179 (2003), ppcA in *Methylobacterium extorquens* AM1 (Arps et al., *J. Bacteriol.* 175:3776-3783 (1993), and ppc in *Corynebacterium glutamicum* (Eikmanns et al., *Mol. Gen. Genet.* 218:330-339 (1989).

| Protein | GenBank ID | GI Number | Organism |
|---|---|---|---|
| Ppc | NP_418391 | 16131794 | *Escherichia coli* |
| ppcA | AAB58883 | 28572162 | *Methylobacterium extorquens* |
| Ppc | ABB53270 | 80973080 | *Corynebacterium glutamicum* |

An alternative enzyme for converting phosphoenolpyruvate to oxaloacetate is PEP carboxykinase, which simultaneously forms an ATP while carboxylating PEP. In most organisms PEP carboxykinase serves a gluconeogenic function and converts oxaloacetate to PEP at the expense of one ATP. *S. cerevisiae* is one such organism whose native PEP carboxykinase, PCK1, serves a gluconeogenic role (Valdes-Hevia et al., *FEBS Lett.* 258:313-316 (1989). *E. coli* is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim et al., *Appl. Environ. Microbiol.* 70:1238-1241 (2004)). Nevertheless, activity of the native *E. coli* PEP carboxykinase from PEP towards oxaloacetate has been recently demonstrated in ppc mutants of *E. coli* K-12 (Kwon et al., *J. Microbiol. Biotechnol.* 16:1448-1452 (2006)). These strains exhibited no growth defects and had increased succinate production at high $NaHCO_3$ concentrations. Alternately, the activity of the *E. coli* enzyme in the oxaloacetate-consuming direction can be reduced by introducing an amino acid substitution at the oxaloacetate binding site (pck R65Q) (Cotelesage et al., *Int. J. Biochem. Cell Biol.* 39:1204-1210 (2007)). Mutant strains of *E. coli* can adopt Pck as the dominant $CO_2$-fixing enzyme following adaptive evolution (Zhang et al., supra, 2009). In some organisms, particularly rumen bacteria, PEP carboxykinase is quite efficient in producing oxaloacetate from PEP and generating ATP. Examples of PEP carboxykinase genes that have been cloned into *E. coli* include those from *Mannheimia succiniciproducens* (Lee et al., *Biotechnol. Bioprocess Eng.* 7:95-99 (2002)), *Anaerobiospirillum succiniciproducens* (Laivenieks et al., *Appl. Environ. Microbiol.* 63:2273-2280 (1997), and *Actinobacillus succinogenes* (Kim et al. supra). The PEPCK enzyme from *Megathyrsus maximus* has a low Km for $CO_2$, a substrate thought to be rate-limiting in the *E. coli* enzyme (Chen et al., *Plant Physiol* 128:160-164 (2002); Cotelesage et al., *Int. J Biochem. Cell Biol.* 39:1204-1210 (2007)). The PEP carboxykinase enzyme of *Haemophilus influenza* is effective at forming oxaloacetate from PEP.

| Protein | GenBank ID | GI Number | Organism |
|---|---|---|---|
| PCK1 | NP_013023 | 6322950 | *Saccharomyces cerevisiae* |
| Pck | NP_417862.1 | 16131280 | *Escherichia coli* |
| pckA | YP_089485.1 | 52426348 | *Mannheimia succiniciproducens* |
| pckA | O09460.1 | 3122621 | *Anaerobiospirillum succiniciproducens* |
| pckA | Q6W6X5 | 75440571 | *Actinobacillus succinogenes* |
| AF532733.1:1..1929 | AAQ10076.1 | 33329363 | *Megathyrsus maximus* |
| pckA | P43923.1 | 1172573 | *Haemophilus influenza* |

FIG. 2, Step B—Pyruvate Carboxylase

Pyruvate carboxylase (EC 6.4.1.1) directly converts pyruvate to oxaloacetate at the cost of one ATP. Pyruvate carboxylase enzymes are encoded by PYC1 (Walker et al., *Biochem. Biophys. Res. Commun.* 176:1210-1217 (1991) and PYC2 (Walker et al., supra) in *Saccharomyces cerevisiae*, and pyc in *Mycobacterium smegmatis* (Mukhopadhyay and Purwantini, *Biochim. Biophys. Acta* 1475:191-206 (2000)).

| Protein | GenBank ID | GI Number | Organism |
|---|---|---|---|
| PYC1 | NP_011453 | 6321376 | *Saccharomyces cerevisiae* |
| PYC2 | NP_009777 | 6319695 | *Saccharomyces cerevisiae* |
| Pyc | YP_890857.1 | 118470447 | *Mycobacterium smegmatis* |

FIG. 2, Step C—Malate Dehydrogenase

Oxaloacetate is converted into malate by malate dehydrogenase (EC 1.1.1.37), an enzyme which functions in both the forward and reverse direction. *S. cerevisiae* possesses three copies of malate dehydrogenase, MDH1 (McAlister-Henn and Thompson, *J. Bacteriol.* 169:5157-5166 (1987), MDH2 (Minard and McAlister-Henn, *Mol. Cell. Biol.* 11:370-380 (1991); Gibson and McAlister-Henn, *J. Biol. Chem.* 278:25628-25636 (2003)), and MDH3 (Steffan and McAlister-Henn, *J. Biol. Chem.* 267:24708-24715 (1992)), which localize to the mitochondrion, cytosol, and peroxisome, respectively. Close homologs to the cytosolic malate dehydrogenase, MDH2, from *S. cerevisiae* are found in several organisms including *Kluyveromyces lactis* and *Candida tropicalis*. *E. coli* is known to have an active malate dehydrogenase encoded by mdh.

| Protein | GenBank ID | GI Number | Organism |
|---|---|---|---|
| MDH1 | NP_012838 | 6322765 | *Saccharomyces cerevisiae* |
| MDH2 | NP_014515 | 116006499 | *Saccharomyces cerevisiae* |
| MDH3 | NP_010205 | 6320125 | *Saccharomyces cerevisiae* |
| KLLA0E07525p | XP_454288.1 | 50308571 | *Kluyveromyces lactis* NRRL Y-1140 |
| YALI0D16753g | XP_502909.1 | 50550873 | *Yarrowia lipolytica* |
| CTRG_01021 | XP_002546239.1 | 255722609 | *Candida tropicalis* MYA-3404 |
| Mdh | NP_417703.1 | 16131126 | *Escherichia coli* |

FIG. 2, Step D—Malic Enzyme

Malic enzyme can be applied to convert $CO_2$ and pyruvate to malate at the expense of one reducing equivalent. Malic enzymes for this purpose can include, without limitation, malic enzyme (NAD-dependent) and malic enzyme (NADP-dependent). For example, one of the E. coli malic enzymes (Takeo, J. Biochem. 66:379-387 (1969)) or a similar enzyme with higher activity can be expressed to enable the conversion of pyruvate and $CO_2$ to malate. By fixing carbon to pyruvate as opposed to PEP, malic enzyme allows the high-energy phosphate bond from PEP to be conserved by pyruvate kinase whereby ATP is generated in the formation of pyruvate or by the phosphotransferase system for glucose transport. Although malic enzyme is typically assumed to operate in the direction of pyruvate formation from malate, overexpression of the NAD-dependent enzyme, encoded by maeA, has been demonstrated to increase succinate production in E. coli while restoring the lethal Δpfl-ΔldhA phenotype under anaerobic conditions by operating in the carbon-fixing direction (Stols and Donnelly, Appl. Environ. Microbiol. 63(7) 2695-2701 (1997)). A similar observation was made upon overexpressing the malic enzyme from Ascaris suum in E. coli (Stols et al., Appl. Biochem. Biotechnol. 63-65(1), 153-158 (1997)). The second E. coli malic enzyme, encoded by maeB, is NADP-dependent and also decarboxylates oxaloacetate and other alpha-keto acids (Iwakura et al., J. Biochem. 85(5):1355-65 (1979)).

| Protein | GenBank ID | GI Number | Organism |
|---|---|---|---|
| maeA | NP_415996 | 90111281 | Escherichia coli |
| maeB | NP_416958 | 16130388 | Escherichia coli |
| NAD-ME | P27443 | 126732 | Ascaris suum |
| MAE1 | NP_012896.1 | 6322823 | Saccharomyces cerevisiae |
| MAE1 | XP_716669.1 | 68478574 | Candida albicans |

FIG. 2, Step E—Fumarase

Fumarate hydratase (EC 4.2.1.2) catalyzes the reversible hydration of fumarate to malate. The three fumarases of E. coli, encoded by fumA, fumB and fumC, are regulated under different conditions of oxygen availability. FumB is oxygen sensitive and is active under anaerobic conditions. FumA is active under microanaerobic conditions, and FumC is active under aerobic growth conditions (Tseng et al., J. Bacteriol. 183:461-467 (2001); Woods et al., Biochim. Biophys. Acta 954:14-26 (1988); Guest et al., J. Gen. Microbiol. 131:2971-2984 (1985)). S. cerevisiae contains one copy of a fumarase-encoding gene, FUM1, whose product localizes to both the cytosol and mitochondrion (Sass et al., J. Biol. Chem. 278:45109-45116 (2003)). Additional fumarase enzymes are found in Campylobacter jejuni (Smith et al., Int. J. Biochem. Cell. Biol. 31:961-975 (1999)), Thermus thermophilus (Mizobata et al., Arch. Biochem. Biophys. 355:49-55 (1998)) and Rattus norvegicus (Kobayashi et al., J. Biochem. 89:1923-1931 (1981)). Similar enzymes with high sequence homology include fum1 from Arabidopsis thaliana and fumC from Corynebacterium glutamicum. The MmcBC fumarase from Pelotomaculum thermopropionicum is another class of fumarase with two subunits (Shimoyama et al., FEMS Microbiol. Lett. 270:207-213 (2007)).

| Protein | GenBank ID | GI Number | Organism |
|---|---|---|---|
| fumA | NP_416129.1 | 16129570 | Escherichia coli |
| fumB | NP_418546.1 | 16131948 | Escherichia coli |
| fumC | NP_416128.1 | 16129569 | Escherichia coli |
| FUM1 | NP_015061 | 6324993 | Saccharomyces cerevisiae |
| fumC | Q8NRN8.1 | 39931596 | Corynebacterium glutamicum |
| fumC | O69294.1 | 9789756 | Campylobacter jejuni |
| fumC | P84127 | 75427690 | Thermus thermophilus |
| fumH | P14408.1 | 120605 | Rattus norvegicus |
| MmcB | YP_001211906 | 147677691 | Pelotomaculum thermopropionicum |
| MmcC | YP_001211907 | 147677692 | Pelotomaculum thermopropionicum |

FIG. 2, Step F—Fumarate Reductase

Fumarate reductase catalyzes the reduction of fumarate to succinate. The fumarate reductase of E. coli, composed of four subunits encoded by frdABCD, is membrane-bound and active under anaerobic conditions. The electron donor for this reaction is menaquinone and the two protons produced in this reaction do not contribute to the proton gradient (Iverson et al., Science 284:1961-1966 (1999)). The yeast genome encodes two soluble fumarate reductase isozymes encoded by FRDS1 (Enomoto et al., DNA Res. 3:263-267 (1996)) and FRDS2 (Muratsubaki et al., Arch. Biochem. Biophys. 352:175-181 (1998)), which localize to the cytosol and promitochondrion, respectively, and are used during anaerobic growth on glucose (Arikawa et al., FEMS Microbiol. Lett. 165:111-116 (1998)).

| Protein | GenBank ID | GI Number | Organism |
|---|---|---|---|
| FRDS1 | P32614 | 418423 | Saccharomyces cerevisiae |
| FRDS2 | NP_012585 | 6322511 | Saccharomyces cerevisiae |
| frdA | NP_418578.1 | 16131979 | Escherichia coli |
| frdB | NP_418577.1 | 16131978 | Escherichia coli |
| frdC | NP_418576.1 | 16131977 | Escherichia coli |
| frdD | NP_418475.1 | 16131877 | Escherichia coli |

Succinate dehydrogenase, encoded by sdhCDAB of E. coli, can also catalyze the reduction of fumarate to succinate. The reversibility of both enzymes is sufficient for SDH and FRD enzymes to complement each other and support growth if the organism is genetically manipulated to express only one or the other. When SDH is expressed under anoxic conditions in the absence of FRD, the SDH complex is able to support a low rate of cell growth by operating as a menaquinol-fumarate reductase (Maklashina et al, J Bacteriol 180:5989-96 (1998)). In another study, Maklashina and coworkers found that the amino acid at position 50 of SdhA is a key residue for determining directionality of the reaction, and that SDH is a more efficient fumarate reductases when Glu is present at this position (Maklashina et al, J Biol Chem 281:11357-65 (2006)).

| Protein | GenBank ID | GI Number | Organism |
|---|---|---|---|
| sdhC | NP_415249.1 | 16128696 | Escherichia coli |
| sdhD | NP_415250.1 | 16128697 | Escherichia coli |
| sdhA | NP_415251.1 | 16128698 | Escherichia coli |
| sdhB | NP_415252.1 | 16128699 | Escherichia coli |

4.3 Example III

Methods of Using Formaldehyde Produced from the Oxidation of Methanol in the Formation of Intermediates of Central Metabolic Pathways for the Formation of Biomass Provided herein are exemplary pathways, which utilize formaldehyde produced from the oxidation of methanol (see, e.g., FIG. 1, step J) in the formation of intermediates of certain central metabolic pathways that can be used for the formation of biomass. Exemplary methanol metabolic pathways for enhancing the availability of reducing equivalents, as well as the producing formaldehyde from methanol (step J), are provided in FIG. 1.

One exemplary pathway that can utilize formaldehyde produced from the oxidation of methanol (e.g., as provided in FIG. 1) is shown in FIG. 3, which involves condensation of formaldehyde and D-ribulose-5-phosphate to form hexylose-6-phosphate (h6p) by hexylose-6-phosphate synthase (FIG. 3, step A). The enzyme can use $Mg^{2+}$ or $Mn^{2+}$ for maximal activity, although other metal ions are useful, and even non-metal-ion-dependent mechanisms are contemplated. H6p is converted into fructose-6-phosphate by 6-phospho-3-hexyloisomerase (FIG. 3, step B).

Another exemplary pathway that involves the detoxification and assimilation of formaldehyde produced from the oxidation of methanol (e.g., as provided in FIG. 1) is shown in FIG. 4 and proceeds through dihydroxyacetone. Dihydroxyacetone synthase is a special transketolase that first transfers a glycoaldehyde group from xylulose-5-phosphate to formaldehyde, resulting in the formation of dihydroxyacetone (DHA) and glyceraldehyde-3-phosphate (G3P), which is an intermediate in glycolysis (FIG. 4, step A). The DHA obtained from DHA synthase is then further phosphorylated to form DHA phosphate by a DHA kinase (FIG. 4, step B). DHAP can be assimilated into glycolysis and several other pathways.

FIG. 3, Steps A and B—Hexylose-6-Phosphate Synthase (Step A) and 6-Phospho-3-hexyloisomerase (Step B)

Both of the hexylose-6-phosphate synthase and 6-phospho-3-hexyloisomerase enzymes are found in several organisms, including methanotrops and methylotrophs where they have been purified (Kato et al., 2006, BioSci Biotechnol Biochem. 70(1):10-21. In addition, these enzymes have been reported in heterotrophs such as *Bacillus subtilis* also where they are reported to be involved in formaldehyde detoxification (Mitsui et al., 2003, AEM 69(10):6128-32, Yasueda et al., 1999. J Bac 181(23):7154-60. Genes for these two enzymes from the methylotrophic bacterium *Mycobacterium gastri* MB19 have been fused and *E. coli* strains harboring the hps-phi construct showed more efficient utilization of formaldehyde (Orita et al., 2007, Appl Microbiol Biotechnol. 76:439-445). In some organisms, these two enzymes naturally exist as a fused version that is bifunctional.

Exemplary candidate genes for hexylose-6-phopshate synthase are:

| Protein | GenBank ID | GI number | Organism |
| --- | --- | --- | --- |
| Hps | AAR39392.1 | 40074227 | *Bacillus methanolicus* MGA3 |
| Hps | EIJ81375.1 | 387589055 | *Bacillus methanolicus* PB1 |
| RmpA | BAA83096.1 | 5706381 | *Methylomonas aminofaciens* |
| RmpA | BAA90546.1 | 6899861 | *Mycobacterium gastri* |
| YckG | BAA08980.1 | 1805418 | *Bacillus subtilis* |

Exemplary gene candidates for 6-phospho-3-hexyloisomerase are:

| Protein | GenBank ID | GI number | Organism |
| --- | --- | --- | --- |
| Phi | AAR39393.1 | 40074228 | *Bacillus methanolicus* MGA3 |
| Phi | EIJ81376.1 | 387589056 | *Bacillus methanolicus* PB1 |
| Phi | BAA83098.1 | 5706383 | *Methylomonas aminofaciens* |
| RmpB | BAA90545.1 | 6899860 | *Mycobacterium gastri* |

Candidates for enzymes where both of these functions have been fused into a single open reading frame include the following.

| Protein | GenBank ID | GI number | Organism |
| --- | --- | --- | --- |
| PH1938 | NP_143767.1 | 14591680 | *Pyrococcus horikoshii* OT3 |
| PF0220 | NP_577949.1 | 18976592 | *Pyrococcus furiosus* |
| TK0475 | YP_182888.1 | 57640410 | *Thermococcus kodakaraensis* |
|  | NP_127388.1 | 14521911 | *Pyrococcus abyssi* |
| MCA2738 | YP_115138.1 | 53803128 | *Methylococcus capsulatas* |

FIG. 4, Step A—Dihydroxyacetone synthase

Another exemplary pathway that involves the detoxification and assimilation of formaldehyde produced from the oxidation of methanol (e.g., as provided in FIG. 1) is shown in FIG. 4 and proceeds through dihydroxyacetone. Dihydroxyacetone synthase is a special transketolase that first transfers a glycoaldehyde group from xylulose-5-phosphate to formaldehyde, resulting in the formation of dihydroxyacetone (DHA) and glyceraldehyde-3-phosphate (G3P), which is an intermediate in glycolysis (FIG. 4, step A). The DHA obtained from DHA synthase is then further phosphorylated to form DHA phosphate by a DHA kinase (FIG. 4, step B). DHAP can be assimilated into glycolysis and several other pathways.

The dihydroxyacetone synthase enzyme in *Candida boidinii* uses thiamine pyrophosphate and $Mg^{2+}$ as cofactors and is localized in the peroxisome. The enzyme from the methanol-growing carboxydobacterium, *Mycobacter* sp. strain JC1 DSM 3803, was also found to have DHA synthase and kinase activities (Ro et al., 1997, JBac 179(19):6041-7). DHA synthase from this organism also has similar cofactor requirements as the enzyme from *C. boidinii*. The $K_m$s for formaldehyde and xylulose 5-phosphate were reported to be 1.86 mM and 33.3 microM, respectively. Several other mycobacteria, excluding only *Mycobacterium tuberculosis*, can use methanol as the sole source of carbon and energy and are reported to use dihydroxyacetone synthase (Part et al., 2003, JBac 185(1):142-7.

| Protein | GenBank ID | GI number | Organism |
| --- | --- | --- | --- |
| DAS1 | AAC83349.1 | 3978466 | *Candida boidinii* |
| HPODL_2613 | EFW95760.1 | 320581540 | *Ogataea parapolymorpha* DL-1 (*Hansenula polymorpha* DL-1) |
|  | AAG12171.2 | 18497328 | *Mycobacter* sp. strain JC1 DSM 3803 |

FIG. 4, Step B—Dihydroxyacetone (PHA) Kinase

DHA obtained from DHA synthase is further phosphorylated to form DHA phosphate by a DHA kinase. DHAP can be assimilated into glycolysis and several other pathways. Dihydroxyacetone kinase has been purified from *Ogataea angusta* to homogeneity (Bystrkh, 1983, Biokhimiia, 48(10):1611-6). The enzyme, which phosphorylates dihydroxyacetone and, to a lesser degree, glyceraldehyde, is a homodimeric protein of 139 kDa. ATP is the preferred phosphate group donor for the enzyme. When ITP, GTP, CTP and UTP are used, the activity drops to about 30%. In several organisms such as *Klebsiella pneumoniae* and *Citrobacter fruendii* (Daniel et al., 1995, JBac 177(15):4392-40), DHA is formed as a result of oxidation of glycerol and is converted into DHAP by the kinase DHA kinase of *K. pneumoniae* has been characterized (Jonathan et al, 1984, JBac 160(1):55-60). It is very specific for DHA, with a $K_m$ of 4 µM, and has two apparent $K_m$ values for ATP, one at 25 to 35 µM, and the other at 200 to 300 DHA can also be phosphorylated by glycerol kinases but the DHA kinase from *K. puemoniae* is different from glycerol kinase in several respects. While both enzymes can phosphorylate dihydroxyacetone, DHA kinase does not phosphorylate glycerol, neither is it inhibited by fructose-1,6-diphosphate. In *Saccharomyces cerevisiae*, DHA kinases (I and II) are involved in rescuing the cells from toxic effects of dihydroxyacetone (Molin et al., 2003, J Biol. Chem. 17; 278(3): 1415-23).

In *Escherichia coli*, DHA kinase is composed of the three subunits DhaK, DhaL, and DhaM and it functions similarly to a phosphotransferase system (PTS) in that it utilizes phosphoenolpyruvate as a phosphoryl donor (Gutknecht et al., 2001, EMBO J. 20(10):2480-6). It differs in not being involved in transport. The phosphorylation reaction requires the presence of the EI and HPr proteins of the PTS system. The DhaM subunit is phosphorylated at multiple sites. DhaK contains the substrate binding site (Garcia-Alles et al., 2004, 43(41):13037-45; Siebold et al., 2003, PNAS. 100(14): 8188-92). The $K_M$ for dihydroxyacetone for the *E. coli* enzyme has been reported to be 6 µM. The K subunit is similar to the N-terminal half of ATP-dependent dihydroxyacetone kinase of *Citrobacter freundii* and eukaryotes.

Exemplary DHA kinase gene candidates for this step are:

| Protein | GenBank ID | GI number | Organism |
|---|---|---|---|
| DAK1 | P54838.1 | 1706391 | *Saccharomyces cerevisiae* S288c |
| DAK2 | P43550.1 | 1169289 | *Saccharomyces cerevisiae* S288c |
| D186_20916 | ZP_16280678.1 | 421847542 | *Citrobacter freundii* |
| DAK2 | ZP_18488498.1 | 425085405 | *Klebsiella pneumoniae* |
| DAK | AAC27705.1 | 3171001 | *Ogataea angusta* |
| DhaK | NP_415718.6 | 162135900 | *Escherichia coli* |
| DhaL | NP_415717.1 | 16129162 | *Escherichia coli* |
| DhaM | NP_415716.4 | 226524708 | *Escherichia coli* |

4.4 Example III

Methods for Handling Anaerobic Cultures

This example describes methods used in handling anaerobic cultures.

A. Anaerobic Chamber and Conditions.

Exemplary anaerobic chambers are available commercially (see, for example, Vacuum Atmospheres Company, Hawthorne Calif.; MBraun, Newburyport Mass.). Conditions included an $O_2$ concentration of 1 ppm or less and 1 atm pure $N_2$. In one example, 3 oxygen scrubbers/catalyst regenerators were used, and the chamber included an $O_2$ electrode (such as Teledyne; City of Industry CA). Nearly all items and reagents were cycled four times in the airlock of the chamber prior to opening the inner chamber door. Reagents with a volume >5 mL were sparged with pure $N_2$ prior to introduction into the chamber. Gloves are changed twice/yr and the catalyst containers were regenerated periodically when the chamber displays increasingly sluggish response to changes in oxygen levels. The chamber's pressure was controlled through one-way valves activated by solenoids. This feature allowed setting the chamber pressure at a level higher than the surroundings to allow transfer of very small tubes through the purge valve.

The anaerobic chambers achieved levels of $O_2$ that were consistently very low and were needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release can be controlled by a bubbler. Instead of using instrument-based $O_2$ monitoring, test strips can be used instead.

B. Anaerobic Microbiology.

In particular, serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 mM of moderate bubbling. This removes most of the oxygen from the medium and, after this step, each bottle is capped with a rubber stopper (such as Bellco 20 mm septum stoppers; Bellco, Vineland, N.J.) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl is added. This is made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle is stoppered immediately as the sodium sulfide solution generates hydrogen sulfide gas upon contact with the cysteine. When injecting into the culture, a syringe filter is used to sterilize the solution. Other components are added through syringe needles, such as B12 (10 cyanocobalamin), nickel chloride ($NiCl_2$, 20 microM final concentration from a 40 mM stock made in anaerobic water in the chamber and sterilized by autoclaving or by using a syringe filter upon injection into the culture), and ferrous ammonium sulfate (final concentration needed is 100 µM—made as 100-1000× stock solution in anaerobic water in the chamber and sterilized by autoclaving or by using a syringe filter upon injection into the culture). To facilitate faster growth under anaerobic conditions, the 1 liter bottles were inoculated with 50 mL of a preculture grown anaerobically. Induction of the pA1-lacO1 promoter in the vectors was performed by addition of isopropyl β-D-1-thiogalactopyranoside (IPTG) to a final concentration of 0.2 mM and was carried out for about 3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles are incubated in an incubator in room air but with continuous nitrogen sparging into the bottles.

4.5 Example IV

Strategies for Increased Production of Succinate

This example describes exemplary strategies to increase production of succinate.

Several strain engineering strategies can be implemented to increase the production of succinate in an organism and to couple it to growth.

Overexpression of carbon-fixing enzymes such as PEP carboxylase or PEP carboxykinase (PEPCK), malic enzyme, and pyruvate carboxylase can be used to redirect carbon flux into succinate formation. Catabolite repression can be removed or reduced by truncating the gene responsible for forming cAMP, adenylate cyclase, cyaA (Crasnier et al, *Mol. Gen. Genet.* 243:409-416 (1994)), and by mutating the catabolite repressor protein, crp (Eppler and Boos, *Mol. Microbiol.* 33:1221-1231 (1999); Karimova et al, *Res. Microbiol.* 155:76-79 (2004); Zhu and Lin, *J. Bacteriol.* 170:2352-2358 (1988)). Decreasing or eliminating byproducts such as ethanol, glycerol, acetate, lactate and formate can be used to improve yields of succinate. In *E. coli* and other prokaryotes, decreasing or eliminating such byproducts can be effected by deletions in alcohol dehydrogenase (adhE), lactate dehydrogenase (ldhA), acetate kinase (ackA), pyruvate oxidase (poxB), and pyruvate formate lyase (pflB). The homologue of pflB, pyruvate formate-lyase 2-ketobutyrate formate-lyase (tdcE), can also be deleted in *E. coli*. Further, deletion of transporters such as the phosphotransferase system (PTS) of glucose uptake increases the PEP pool in the organism and this has been demonstrated to improve succinate production in the literature. This can be accomplished by deletion, mutation or truncation of ptsG, ptsH, ptsI or crr or their combinations (Zhang et al, *Proc. Natl. Acad. Sci. USA* 106(48):20180-20185 (2009), Flores et al, *Mol. Microbiol. Biotechnol.* 13:105-116 (2007); Sanchez et al., *Biotechnol. Prog.* 21(2):358-365 (2005)). This deletion can optionally be accompanied by overexpression of glucokinase encoded by glk and galactose permease encoded by galP. Similarly, deletion in pyruvate kinase (pykA, pykF) prevents the conversion of PEP to pyruvate and improves succinate production. Further, high concentrations of $CO_2$ in the fermenters allow the function of PEPCK and pyruvate carboxylase in the anaplerotic direction, as needed for succinate production. While exemplified above with specific genes, it is understood by those skilled in the art that genes performing the same or similar functions can be genetically modified in the appropriate host organism to achieve a similar improvement in succinate production.

Similar strategies to those proposed above can be used for production of succinate in yeasts such as *Saccharomyces cerevisiae* and *Candida*. Carbon flux towards succinate can be improved by deleting or tuning down competing pathways. Typical fermentation products of yeast include ethanol, glycerol and $CO_2$. The elimination of these byproducts can be accomplished by approaches delineated herein. Other potential byproducts include lactate, acetate, formate and amino acids.

Ethanol can be formed from pyruvate in two enzymatic steps catalyzed by pyruvate decarboxylase and ethanol dehydrogenase. *Saccharomyces cerevisiae* has three pyruvate decarboxylases (PDC1, PDC5 and PDC6). PDC1 is the major isozyme and is strongly expressed in actively fermenting cells. PDC5 also functions during glycolytic fermentation, but is expressed only in the absence of PDC1 or under thiamine limiting conditions. PDC6 functions during growth on nonfermentable carbon sources. Deleting PDC1 and PDC5 can reduce ethanol production significantly; however these deletions can lead to mutants with increased PDC6 expression. Deletion of all three eliminates ethanol formation completely but also can cause a growth defect because of inability of the cells to form sufficient acetyl-CoA for biomass formation. This, however, can be overcome by evolving cells in the presence of reducing amounts of C2 carbon source (ethanol or acetate) (van Maris et al, *AEM* 69:2094-9 (2003)). It has also been reported that deletion of the positive regulator PDC2 of pyruvate decarboxylases PDC1 and PDC5, reduced ethanol formation to ~10% of that made by wild-type (Hohmann et al, *Mol Gen Genet.* 241:657-66 (1993)). Pyruvate decarboxylase (PDC) is a key enzyme in alcoholic fermentation, catalyzing the decarboxylation of pyruvate to acetaldehyde. The PDC1 enzyme from *Saccharomyces cerevisiae* has been extensively studied (Killenberg-Jabs et al., *Eur. J. Biochem.* 268:1698-1704 (2001); Li et al., *Biochemistry.* 38:10004-10012 (1999); ter Schure et al., *Appl. Environ. Microbiol.* 64:1303-1307 (1998)). Other well-characterized PDC enzymes are found in *Zymomonas mobilis* (Siegert et al., *Protein Eng Des Sel* 18:345-357 (2005)), *Acetobacter pasteurians* (Chandra et al., 176:443-451 (2001)) and *Kluyveromyces lactis* (Krieger et al., 269:3256-3263 (2002)). The PDC1 and PDC5 enzymes of *Saccharomyces cerevisiae* are subject to positive transcriptional regulation by PDC2 (Hohmann et al, *Mol Gen Genet.* 241:657-66 (1993)). Pyruvate decarboxylase activity is also possessed by a protein encoded by CTRG_03826 (GI:255729208) in *Candida tropicalis*, PDC1 (GI number: 1226007) in *Kluyveromyces lactis*, YALI0D10131g (GI:50550349) in *Yarrowia lipolytica*, PAS_chr3_0188 (GI:254570575) in *Pichia pastoris*, pyruvate decarboxylase (GI: GI:159883897) in *Schizosaccharomyces pombe*, ANI_1_1024084 (GI:145241548), ANI_1_796114 (GI:317034487), ANI_1_936024 (GI:317026934) and ANI_1_2276014 (GI:317025935) in *Aspergillus niger*.

| Protein | GenBank ID | GI Number | Organism |
| --- | --- | --- | --- |
| Pdc | P06672.1 | 118391 | *Zymomonas mobilis* |
| pdc1 | P06169 | 30923172 | *Saccharomyces cerevisiae* |
| Pdc2 | NP_010366.1 | 6320286 | *Saccharomyces cerevisiae* |
| Pdc5 | NP_013235.1 | 6323163 | *Saccharomyces cerevisiae* |
| CTRG_03826 | XP_002549529 | 255729208 | *Candida tropicalis*, |
| CU329670.1:585597.587312 | CAA90807 | 159883897 | *Schizosaccharomyces pombe* |
| YALI0D10131g | XP_502647 | 50550349 | *Yarrowia lipolytica* |
| PAS_chr3_0188 | XP_002492397 | 254570575 | *Pichia pastoris* |
| Pdc | Q8L388 | 20385191 | *Acetobacter pasteurians* |
| pdc1 | Q12629 | 52788279 | *Kluyveromyces lactis* |
| ANI_1_1024084 | XP_001393420 | 145241548 | *Aspergillus niger* |
| ANI_1_796114 | XP_001399817 | 317026934 | *Aspergillus niger* |
| ANI_1_936024 | XP_001396467 | 317034487 | *Aspergillus niger* |
| ANI_1_2276014 | XP_001388598 | 317025935 | *Aspergillus niger* |

Ethanol dehydrogenases that convert acetaldehyde into ethanol and/or other short chain alcohol dehydrogenases can be deleted or attenuated to provide carbon and reducing equivalents for the succinate pathway. To date, seven alcohol dehydrogenases, ADHI-ADHVII, have been reported in *S. cerevisiae* (de Smidt et al, *FEMS Yeast Res* 8:967-78 (2008)). ADH1 (GI:1419926) is the key enzyme responsible for reducing acetaldehyde to ethanol in the cytosol under anaerobic conditions. It has been reported that a yeast strain deficient in ADH1 cannot grow anaerobically because an active respiratory chain is the only alternative path to regenerate NADH and lead to a net gain of ATP (Drewke et al, *J Bacteriol* 172:3909-17 (1990)). This enzyme is an ideal candidate for downregulation to limit ethanol production. ADH2 is severely repressed in the presence of glucose. In *K.* lactis, two NAD-dependent cytosolic alcohol dehydrogenases have been identified and characterized. These genes also show activity for other aliphatic alcohols. The genes ADH1 (GI:113358) and ADHII (GI:51704293) are preferentially expressed in glucose-grown cells (Bozzi et al, Biochim Biophys Acta 1339:133-142 (1997)). Cytosolic alcohol dehydrogenases are encoded by ADH1 (GI:608690) in C. albicans, ADH1 (GI:3810864) in S. pombe, ADH1 (GI:5802617) in Y. lipolytica, ADH1 (GI:2114038) and ADHII (GI:2143328) in Pichia stipitis or Scheffersomyces stipitis (Passoth et al, Yeast 14:1311-23 (1998)). Candidate alcohol dehydrogenases are shown the table below.

| Protein | GenBank ID | GI number Organism |
| --- | --- | --- |
| SADH | BAA24528.1 | 2815409 Candida parapsilosis |
| ADH1 | NP_014555.1 | 6324486 Saccharomyces cerevisiae s288c |
| ADH2 | NP_014032.1 | 6323961 Saccharomyces cerevisiae s288c |
| ADH3 | NP_013800.1 | 6323729 Saccharomyces cerevisiae s288c |
| ADH4 | NP_011258.2 | 269970305 Saccharomyces cerevisiae s288c |
| ADH5 (SFA1) | NP_010113.1 | 6320033 Saccharomyces cerevisiae s288c |
| ADH6 | NP_014051.1 | 6323980 Saccharomyces cerevisiae s288c |
| ADH7 | NP_010030.1 | 6319949 Saccharomyces cerevisiae s288c |
| adhP | CAA44614.1 | 2810 Kluyveromyces lactis |
| ADH1 | P20369.1 | 113358 Kluyveromyces lactis |
| ADH2 | CAA45739.1 | 2833 Kluyveromyces lactis |
| ADH3 | P49384.2 | 51704294 Kluyveromyces lactis |
| ADH1 | CAA57342.1 | 608690 Candida albicans |
| ADH2 | CAA21988.1 | 3859714 Candida albicans |
| SAD | XP_712899.1 | 68486457 Candida albicans |
| ADH1 | CAA21782.1 | 3810864 Schizosaccharomyces pombe |
| ADH1 | AAD51737.1 | 5802617 Yarrowia lipolytica |
| ADH2 | AAD51738.1 | 5802619 Yarrowia lipolytica |
| ADH3 | AAD51739.1 | 5802621 Yarrowia lipolytica |
| AlcB | AAX53105.1 | 61696864 Aspergillus niger |
| ANI_1_282024 | XP_001399347.1 | 145231748 Aspergillus niger |
| ANI_1_126164 | XP_001398574.2 | 317037131 Aspergillus niger |
| ANI_1_1756104 | XP_001395505.2 | 317033815 Aspergillus niger |
| ADH2 | CAA73827.1 | 2143328 Scheffersomyces stipitis |

Attenuation or deletion of one or more glycerol-3-phosphatase or glycerol-3-phosphate (G3P) dehydrogenase enzymes can eliminate or reduce the formation of glycerol, and thereby conserve carbon and reducing equivalents for production of succinate.

G3P phosphatase catalyzes the hydrolysis of G3P to glycerol. Enzymes with this activity include the glycerol-1-phosphatase (EC 3.1.3.21) enzymes of Saccharomyces cerevisiae (GPP1 and GPP2), Candida albicans and Dunaleilla parva (Popp et al, Biotechnol Bioeng 100:497-505 (2008); Fan et al, FEMS Microbial Lett 245:107-16 (2005)). The D. parva gene has not been identified to date. These and additional G3P phosphatase enzymes are shown in the table below.

| Protein | GenBank ID | GI Number Organism |
| --- | --- | --- |
| GPP1 | DAA08494.1 | 285812595 Saccharomyces cerevisiae |
| GPP2 | NP_010984.1 | 6320905 Saccharomyces cerevisiae |
| GPP1 | XP_717809.1 | 68476319 Candida albicans |
| KLLA0C08217g | XP_452565.1 | 50305213 Kluyveromyces lactis |
| KLLA0C11143g | XP_452697.1 | 50305475 Kluyveromyces lactis |
| ANI_1_380074 | XP_001392369.1 | 145239445 Aspergillus niger |
| ANI_1_444054 | XP_001390913.2 | 317029125 Aspergillus niger |

S. cerevisiae has three G3P dehydrogenase enzymes encoded by GPD1 and GDP2 in the cytosol and GUT2 in the mitochondrion. GPD2 is known to encode the enzyme responsible for the majority of the glycerol formation and is responsible for maintaining the redox balance under anaerobic conditions. GPD1 is primarily responsible for adaptation of S. cerevisiae to osmotic stress (Bakker et al., FEMS Microbiol Rev 24:15-37 (2001)). Attenuation of GPD1, GPD2 and/or GUT2 will reduce glycerol formation. GPD1 and GUT2 encode G3P dehydrogenases in Yarrowia lipolytica (Beopoulos et al, AEM 74:7779-89 (2008)). GPD1 and GPD2 encode for G3P dehydrogenases in S. pombe. Similarly, G3P dehydrogenase is encoded by CTRG_02011 in Candida tropicalis and a gene represented by GI:20522022 in Candida albicans.

| Protein | GenBank ID | GI number Organism |
| --- | --- | --- |
| GPD1 | CAA98582.1 | 1430995 Saccharomyces cerevisiae |
| GPD2 | NP_014582.1 | 6324513 Saccharomyces cerevisiae |
| GUT2 | NP_012111.1 | 6322036 Saccharomyces cerevisiae |
| GPD1 | CAA22119.1 | 6066826 Yarrowia lipolytica |
| GUT2 | CAG83113.1 | 49646728 Yarrowia lipolytica |
| GPD1 | CAA22119.1 | 3873542 Schizosaccharomyces pombe |
| GPD2 | CAA91239.1 | 1039342 Schizosaccharomyces pombe |
| ANI_1_786014 | XP_001389035.2 | 317025419 Aspergillus niger |
| ANI_1_1768134 | XP_001397265.1 | 145251503 Aspergillus niger |
| KLLA0C04004g | XP_452375.1 | 50304839 Kluyveromyces lactis |
| CTRG_02011 | XP_002547704.1 | 255725550 Candida tropicalis |
| GPD1 | XP_714362.1 | 68483412 Candida albicans |
| GPD2 | XP_713824.1 | 68484586 Candida albicans |

Enzymes that form acid byproducts such as acetate, formate and lactate can also be tuned down or deleted. Such enzymes include acetate kinase, phosphotransacetylase and pyruvate oxidase.

An exemplary acetate kinase is the E. coli acetate kinase, encoded by ackA (Skarstedt and Silverstein J. Biol. Chem. 251:6775-6783 (1976)). Homologs exist in several other organisms including Salmonella enterica and Chlamydomonas reinhardtii. Information related to these proteins and genes is shown below:

| Protein | GenBank ID | GI number Organism |
| --- | --- | --- |
| AckA | NP_416799.1 | 16130231 Escherichia coli |
| AckA | NP_461279.1 | 16765664 Salmonella enterica subsp. enterica serovar Typhimurium str. LT2 |
| ACK1 | XP_001694505.1 | 159472745 Chlamydomonas reinhardtii |
| ACK2 | XP_001691682.1 | 159466992 Chlamydomonas reinhardtii |

An exemplary phosphate-transferring acyltransferase is phosphotransacetylase, encoded by pta. The pta gene from E. coli encodes an enzyme that can convert acetyl-CoA into acetyl-phosphate, and vice versa (Suzuki, T. Biochim. Biophys. Acta 191:559-569 (1969)). This enzyme can also utilize propionyl-CoA instead of acetyl-CoA forming propionate in the process (Hesslinger et al. *Mol. Microbiol* 27:477-492 (1998)). Homologs exist in several other organisms including *Salmonella enterica* and *Chlamydomonas reinhardtii*.

| Protein | GenBank ID | GI number | Organism |
|---|---|---|---|
| Pta | NP_416800.1 | 16130232 | *Escherichia coli* |
| Pta | NP_461280.1 | 16765665 | *Salmonella enterica* subsp. enterica serovar Typhimurium str. LT2 |
| PAT2 | XP_001694504.1 | 159472743 | *Chlamydomonas reinhardtii* |
| PAT1 | XP_001691787.1 | 159467202 | *Chlamydomonas reinhardtii* |

Pyruvate oxidase (acetate-forming) or pyruvate:quinone oxidoreductase (PQO) catalyzes the oxidative decarboxylation of pyruvate into acetate, using ubiquione (EC 1.2.5.1) or quinone (EC 1.2.2.1) as an electron acceptor. The *E. coli* enzyme, PoxB, is localized on the inner membrane (Abdel-Hamid et al., *Microbiol* 147:1483-98 (2001)). The enzyme has thiamin pyrophosphate and flavin adenine dinucleotide (FAD) cofactors (Koland and Gennis, *Biochemistry* 21:4438-4442 (1982)); O'Brien et al., *Biochemistry* 16:3105-3109 (1977); O'Brien and Gennis, *J. Biol. Chem.* 255:3302-3307 (1980)). PoxB has similarity to pyruvate decarboxylase of *S. cerevisiae* and *Zymomonas mobilis*. The pqo transcript of *Corynebacterium glutamicum* encodes a quinone-dependent and acetate-forming pyruvate oxidoreductase (Schreiner et al., *J Bacteriol* 188:1341-50 (2006)). Similar enzymes can be inferred by sequence homology.

| Protein | GenBank ID | GI Number | Organism |
|---|---|---|---|
| poxB | NP_415392.1 | 16128839 | *Escherichia coli* |
| Pqo | YP_226851.1 | 62391449 | *Corynebacterium glutamicum* |
| poxB | YP_309835.1 | 74311416 | *Shigella sonnei* |
| poxB | ZP_03065403.1 | 194433121 | *Shigella dysenteriae* |

Deletion or attenuation of pyruvate formate lyase could limit formation of formate. Pyruvate formate-lyase (PFL, EC 2.3.1.54), encoded by pflB in *E. coli*, can convert pyruvate into acetyl-CoA and formate. The activity of PFL can be enhanced by an activating enzyme encoded by pflA (Knappe et al., *Proc. Natl. Acad. Sci U.S.A* 81:1332-1335 (1984); Wong et al., *Biochemistry* 32:14102-14110 (1993)). Keto-acid formate-lyase (EC 2.3.1.-), also known as 2-ketobutyrate formate-lyase (KFL) and pyruvate formate-lyase 4, is the gene product of tdcE in *E. coli*. This enzyme catalyzes the conversion of 2-ketobutyrate to propionyl-CoA and formate during anaerobic threonine degradation, and can also substitute for pyruvate formate-lyase in anaerobic catabolism (Simanshu et al., *J Biosci.* 32:1195-1206 (2007)). The enzyme is oxygen-sensitive and, like PflB, can require post-translational modification by PFL-AE to activate a glycyl radical in the active site (Hesslinger et al., *Mol. Microbiol* 27:477-492 (1998)). A pyruvate formate-lyase from *Archaeglubus fulgidus* encoded by pflD has been cloned, expressed in *E. coli* and characterized (Lehtio et al., *Protein Eng Des Sel* 17:545-552 (2004)). The crystal structures of the *A. fulgidus* and *E. coli* enzymes have been resolved (Lehtio et al., *J. Mol. Biol.* 357:221-235 (2006); Leppanen et al., *Structure.* 7:733-744 (1999)). Additional PFL and PFL-AE candidates are found in *Lactococcus lactis* (Melchiorsen et al., *Appl Microbiol Biotechnol* 58:338-344 (2002)), and *Streptococcus mutans* (Takahashi-Abbe et al., *Oral. Microbiol Immunol.* 18:293-297 (2003)), *Chlamydomonas reinhardtii* (Hemschemeier et al., *Eukaryot. Cell* 7:518-526 (2008b); Atteia et al., *J. Biol. Chem.* 281:9909-9918 (2006)) and *Clostridium pasteurianum* (Weidner et al., *J. Bacteriol.* 178:2440-2444 (1996)).

| Protein | GenBank ID | GI Number | Organism |
|---|---|---|---|
| pflB | NP_415423 | 16128870 | *Escherichia coli* |
| pflA | NP_415422.1 | 16128869 | *Escherichia coli* |
| tdcE | AAT48170.1 | 48994926 | *Escherichia coli* |
| pflD | NP_070278.1 | 11499044 | *Archaeglubus fulgidus* |
| Pfl | CAA03993 | 2407931 | *Lactococcus lactis* |
| Pfl | BAA09085 | 1129082 | *Streptococcus mutans* |
| PFL1 | XP_001689719.1 | 159462978 | *Chlamydomonas reinhardtii* |
| pflA1 | XP_001700657.1 | 159485246 | *Chlam domonas reinhardtii* |
| Pfl | Q46266.1 | 2500058 | *Clostridium pasteurianum* |
| Act | CAA63749.1 | 1072362 | *Clostridium pasteurianum* |

Alcohol dehydrogenases that convert pyruvate to lactate are also candidates for deletion or attenuation. Lactate dehydrogenase enzymes include ldhA of *E. coli* and ldh from *Ralstonia eutropha* (Steinbuchel and Schlegel, *Eur. J. Biochem.* 130:329-334 (1983)). Other alcohol dehydrogenases listed above may also exhibit LDH activity.

| Protein | GenBank ID | GI number | Organism |
|---|---|---|---|
| ldhA | NP_415898.1 | 16129341 | *Escherichia coli* |
| Ldh | YP_725182.1 | 113866693 | *Ralstonia eutropha* |

Tuning down activity of the mitochondrial pyruvate dehydrogenase complex will limit flux into the mitochondrial TCA cycle. Under anaerobic conditions and in conditions where glucose concentrations are high in the medium, the capacity of this mitochondrial enzyme is very limited and there is no significant flux through it. However, in some embodiments, this enzyme can be disrupted or attenuated to increase succinate production. Exemplary pyruvate dehydrogenase genes include PDB1, PDA1, LAT1 and LPD1.

The pyruvate dehydrogenase (PDH) complex catalyzes the conversion of pyruvate to acetyl-CoA. The *E. coli* PDH complex is encoded by the genes aceEF and lpdA. Enzyme engineering efforts have improved the *E. coli* PDH enzyme activity under anaerobic conditions (Kim et al., *J. Bacteriol.* 190:3851-3858 (2008); Kim et al., *Appl Environ. Microbiol.* 73:1766-1771 (2007); Zhou et al., *Biotechnol Lett.* 30:335-342 (2008)). In contrast to the *E. coli* PDH, the *B. subtilis* complex is active and required for growth under anaerobic conditions (Nakano et al., 179:6749-6755 (1997)). The *Klebsiella pneumoniae* PDH, characterized during growth on glycerol, is also active under anaerobic conditions (Menzel et al., 56:135-142 (1997)). Crystal structures of the enzyme complex from bovine kidney (Zhou et al., 98:14802-14807 (2001)) and the E2 catalytic domain from *Azotobacter vinelandii* are available (Mattevi et al., *Science.* 255:1544-1550 (1992)). Some mammalian PDH enzymes complexes can react on alternate substrates such as 2-oxobutanoate. Comparative kinetics of *Rattus norvegicus* PDH and BCKAD indicate that BCKAD has higher activity on 2-oxobutanoate as a substrate (Paxton et al., *Biochem.* 1 234:295-303 (1986)). The *S. cerevisiae* PDH complex can-consist of an E2 (LAT1) core that binds E1 (PDA), PDB1), E3 (LPD1), and Protein X (PDX1) components (Pronk et al., *Yeast* 12:1607-1633 (1996)). The PDH complex of *S. cerevisiae* is regulated by phosphorylation of E1 involving PKP1 (PDH kinase I), PTC5 (PDH phosphatase 1), PKP2 and PTC6. Modification of these regulators may also enhance PDH activity. Coexpression of lipoyl ligase (Lp1A of *E. coli* and AIM22 in *S. cerevisiae*) with PDH in the cytosol may be necessary for activating the PDH enzyme complex. Increasing the supply of cytosolic lipoate, either by modifying a metabolic pathway or media supplementation with lipoate, may also improve PDH activity.

| Gene | Accession No. | GI Number | Organism |
|---|---|---|---|
| aceE | NP_414656.1 | 16128107 | *Escherichia coli* |
| aceF | NP_414657.1 | 16128108 | *Escherichia coli* |
| Lpd | NP_414658.1 | 16128109 | *Escherichia coli* |
| lplA | NP_418803.1 | 16132203 | *Escherichia coli* |
| pdhA | P21881.1 | 3123238 | *Bacillus subtilis* |
| pdhB | P21882.1 | 129068 | *Bacillus subtilis* |
| pdhC | P21883.2 | 129054 | *Bacillus subtilis* |
| pdhD | P21880.1 | 118672 | *Bacillus subtilis* |
| aceE | YP_001333808.1 | 152968699 | *Klebsiella pneumoniae* |
| aceF | YP_001333809.1 | 152968700 | *Klebsiella pneumoniae* |
| lpdA | YP_001333810.1 | 152968701 | *Klebsiella pneumoniae* |
| Pdha1 | NP_001004072.2 | 124430510 | *Rattus norvegicus* |
| Pdha2 | NP_446446.1 | 16758900 | *Rattus norvegicus* |
| Dlat | NP_112287.1 | 78365255 | *Rattus norvegicus* |
| Dld | NP_955417.1 | 40786469 | *Rattus norvegicus* |
| LAT1 | NP_014328 | 6324258 | *Saccharomyces cerevisiae* |
| PDA1 | NP_011105 | 37362644 | *Saccharomyces cerevisiae* |
| PDB1 | NP_009780 | 6319698 | *Saccharomyces cerevisiae* |
| LPD1 | NP_116635 | 14318501 | *Saccharomyces cerevisiae* |
| PDX1 | NP_011709 | 6321632 | *Saccharomyces cerevisiae* |
| AIM22 | NP_012489.2 | 83578101 | *Saccharomyces cerevisiae* |

Another strategy for reducing flux into the TCA cycle is to limit transport of pyruvate into the mitochondria by tuning down or deleting the mitochondrial pyruvate carrier. Transport of pyruvate into the mitochondria in *S. cerevisiae* is catalyzed by a heterocomplex encoded by MPC1 and MPC2 (Herzig et al, Science 337:93-6 (2012); Bricker et al, Science 337:96-100 (2012)). *S. cerevisiae* encodes five other putative monocarboxylate transporters (MCH1-5), several of which may be localized to the mitochondrial membrane (Makuc et al, Yeast 18:1131-43 (2001)). NDT1 is another putative pyruvate transporter, although the role of this protein is disputed in the literature (Todisco et al, *J Biol Chem* 20:1524-31 (2006)). Exemplary pyruvate and monocarboxylate transporters are shown in the table below:

| Protein | GenBank ID | GI number | Organism |
|---|---|---|---|
| MPC1 | NP_011435.1 | 6321358 | *Saccharomyces cerevisiae* |
| MPC2 | NP_012032.1 | 6321956 | *Saccharomyces cerevisiae* |
| MPC1 | XP_504811.1 | 50554805 | *Yarrowia lipolytica* |
| MPC2 | XP_501390.1 | 50547841 | *Yarrowia lipolytica* |
| MPC1 | XP_719951.1 | 68471816 | *Candida albicans* |
| MPC2 | XP_716190.1 | 68479656 | *Candida albicans* |
| MCH1 | NP_010229.1 | 6320149 | *Saccharomyces cerevisiae* |
| MCH2 | NP_012701.2 | 330443640 | *Saccharomyces cerevisiae* |
| MCH3 | NP_014274.1 | 6324204 | *Saccharomyces cerevisiae* |
| MCH5 | NP_014951.2 | 330443742 | *Saccharomyces cerevisiae* |
| NDT1 | NP_012260.1 | 6322185 | *Saccharomyces cerevisiae* |
| ANI_1_1592184 | XP_001401484.2 | 317038471 | *Aspergillus niger* |
| CaJ7_0216 | XP_888808.1 | 77022728 | *Candida albicans* |
| YALI0E16478g | XP_504023.1 | 50553226 | *Yarrowia lipolytica* |
| KLLA0D14036g | XP_453688.1 | 50307419 | *Kluyveromyces lactis* |

One exemplary method to provide an increased number of reducing equivalents, such as NAD(P)H, for enabling the formation of succinate is to constrain the use of such reducing equivalents during respiration. Respiration can be limited by: reducing the availability of oxygen, attenuating NADH dehydrogenases and/or cytochrome oxidase activity, attenuating G3P dehydrogenase, and/or providing excess glucose to Crabtree positive organisms.

Restricting oxygen availability by culturing the non-naturally occurring eukaryotic organisms in a fermenter is one approach for limiting respiration and thereby increasing the ratio of NAD(P)H to NAD(P). The ratio of NAD(P)H/NAD(P) increases as culture conditions get more anaerobic, with completely anaerobic conditions providing the highest ratios of the reduced cofactors to the oxidized ones. For example, it has been reported that the ratio of NADH/NAD=0.02 in aerobic conditions and 0.75 in anaerobic conditions in *E. coli* (de Graes et al, J Bacteriol 181:2351-57 (1999)).

Respiration can also be limited by reducing expression or activity of NADH dehydrogenases and/or cytochrome oxidases in the cell under aerobic conditions. In this case, respiration will be limited by the capacity of the electron transport chain. Such an approach has been used to enable anaerobic metabolism of *E. coli* under completely aerobic conditions (Portnoy et al, *AEM* 74:7561-9 (2008)). *S. cerevisiae* can oxidize cytosolic NADH directly using external NADH dehydrogenases, encoded by NDE1 and NDE2. One such NADH dehydrogenase in *Yarrowia lipolytica* is encoded by NDH2 (Kerscher et al, *J Cell Sci* 112:2347-54 (1999)). These and other NADH dehydrogenase enzymes are listed in the table below.

| Protein | GenBank ID | GI number | Organism |
|---|---|---|---|
| NDE1 | NP_013865.1 | 6323794 | *Saccharomyces cerevisiae* s288c |
| NDE2 | NP_010198.1 | 6320118 | *Saccharomyces cerevisiae* s288c |
| NDH2 | AJ006852.1 | 3718004 | *Yarrowia lipolytica* |
| ANI_1_610074 | XP_001392541.2 | 317030427 | *Aspergillus niger* |
| ANI_1_2462094 | XP_001394893.2 | 317033119 | *Aspergillus niger* |
| KLLA0E21891g | XP_454942.1 | 50309857 | *Kluyveromyces lactis* |
| KLLA0C06336g | XP_452480.1 | 50305045 | *Kluyveromyces lactis* |
| NDE1 | XP_720034.1 | 68471982 | *Candida albicans* |
| NDE2 | XP_717986.1 | 68475826 | *Candida albicans* |

Cytochrome oxidases of *Saccharomyces cerevisiae* include the COX gene products. COX1-3 are the three core subunits encoded by the mitochondrial genome, whereas COX4-13 are encoded by nuclear genes. Attenuation or deletion of any of the cytochrome genes results in a decrease or block in respiratory growth (Hermann and Funes, Gene 354:43-52 (2005)). Cytochrome oxidase genes in other organisms can be inferred by sequence homology.

| Protein | GenBank ID | GI number | Organism |
|---|---|---|---|
| COX1 | CAA09824.1 | 4160366 | *Saccharomyces cerevisiae* s288c |
| COX2 | CAA09845.1 | 4160387 | *Saccharomyces cerevisiae* s288c |
| COX3 | CAA09846.1 | 4160389 | *Saccharomyces cerevisiae* s288c |
| COX4 | NP_011328.1 | 6321251 | *Saccharomyces cerevisiae* s288c |
| COX5A | NP_014346.1 | 6324276 | *Saccharomyces cerevisiae* s288c |
| COX5B | NP_012155.1 | 6322080 | *Saccharomyces cerevisiae* s288c |
| COX6 | NP_011918.1 | 6321842 | *Saccharomyces cerevisiae* s288c |
| COX7 | NP_013983.1 | 6323912 | *Saccharomyces cerevisiae* s288c |
| COX8 | NP_013499.1 | 6323427 | *Saccharomyces cerevisiae* s288c |
| COX9 | NP_010216.1 | 6320136 | *Saccharomyces cerevisiae* s288c |
| COX12 | NP_013139.1 | 6323067 | *Saccharomyces cerevisiae* s288c |
| COX13 | NP_011324.1 | 6321247 | *Saccharomyces cerevisiae* s288c |

Cytosolic NADH can also be oxidized by the respiratory chain via the G3P dehydrogenase shuttle, consisting of cytosolic NADH-linked G3P dehydrogenase and a membrane-bound G3P:ubiquinone oxidoreductase. The deletion or attenuation of G3P dehydrogenase enzymes will also prevent the oxidation of NADH for respiration. Enzyme candidates encoding these enzymes were described above.

Additionally, in Crabtree positive organisms, fermentative metabolism can be achieved in the presence of excess of glucose. For example, *S. cerevisiae* makes ethanol even under aerobic conditions. The formation of ethanol and glycerol can be reduced/eliminated and replaced by the production of succinate in a Crabtree positive organism by feeding excess glucose to the Crabtree positive organism. In another aspect provided herein is a method for producing succinate, comprising culturing a non-naturally occurring eukaryotic organism under conditions and for a sufficient period of time to produce succinate, wherein the eukaryotic organism is a Crabtree positive organism that comprises at least one nucleic acid encoding a succinate pathway enzyme and wherein eukaryotic organism is in a culture medium comprising excess glucose.

Reduced activity of pyruvate kinase encoded by pyk1 and pyk2 can also be used to increase the pool of PEP for succinate production. Pyruvate kinase, also known as phosphoenolpyruvate synthase (EC 2.7.9.2), converts pyruvate and ATP to PEP and AMP. This enzyme is encoded by the PYK1 (Burke et al., *J. Biol. Chem.* 258:2193-2201 (1983)) and PYK2 (Boles et al., *J. Bacteriol.* 179:2987-2993 (1997)) genes in *S. cerevisiae*. In *E. coli*, this activity is catalyzed by the gene products of pykF and pykA. Selected homologs of the *S. cerevisiae* enzymes are also shown in the table below.

| Protein | GenBank ID | GI Number | Organism |
|---|---|---|---|
| PYK1 | NP_009362 | 6319279 | *Saccharomyces cerevisiae* |
| PYK2 | NP_014992 | 6324923 | *Saccharomyces cerevisiae* |
| pykF | NP_416191.1 | 16129632 | *Escherichia coli* |
| pykA | NP_416368.1 | 16129807 | *Escherichia coli* |
| KLLA0F23397g | XP_4456122.1 | 50312181 | *Kluyveromyces lactis* |
| CaO19.3575 | XP_714934.1 | 68482353 | *Candida albicans* |
| CaO19.11059 | XP_714997.1 | 68482226 | *Candida albicans* |
| YALI0F09185p | XP_505195 | 210075987 | *Yarrowia lipolytica* |
| ANI_1_1126064 | XP_001391973 | 145238652 | *Aspergillus niger* |

4.6 Example V

Increased Production of Succinate in Microbial Organisms

This example describes engineering of microbial organisms for increased production of succinate.

In *E. coli*, the relevant genes are expressed in a synthetic operon behind an inducible promoter on a medium- or high-copy plasmid; for example the PBAD promoter which is induced by arabinose, on a plasmid of the pBAD series (Guzman et al., *J Bacteriol.* 177:4121-4130 (1995)). In *S. cerevisiae*, genes are integrated into the chromosome behind the PDC1 promoter, replacing the native pyruvate carboxylase gene. It has been reported that this results in higher expression of foreign genes than from a plasmid (Ishida et al., *Appl. Environ. Microbiol.* 71:1964-1970 (2005)), and will also ensure expression during anaerobic conditions.

Cells containing the relevant constructs are grown in suitable growth media, for example, minimal media containing glucose. The addition of arabinose can be included in the case of *E. coli* containing genes expressed under the PBAD promoter. Periodic samples are taken for both gene expression and enzyme activity analysis. Enzyme activity assays are performed on crude cell extracts using procedures well known in the art. Alternatively, assays based on the oxidation of NAD(P)H, which is produced in all dehydrogenase reaction steps and detectable by spectrophotometry can be utilized. In addition, antibodies can be used to detect the level of particular enzymes. In lieu of or in addition to enzyme activity measurements, RNA can be isolated from parallel samples and transcript of the gene of interest measured by reverse transcriptase PCR. Any constructs lacking detectable transcript expression are reanalyzed to ensure the encoding nucleic acids are harbored in an expressible form. Where transcripts are detected, this result indicates either a lack of translation or production of inactive enzyme. A variety of methods well known in the art can additionally be employed, such as codon optimization, engineering a strong ribosome binding site, use of a gene from a different species, and prevention of N-glycosylation (for expression of bacterial enzymes in yeast) by conversion of Asn residues to Asp. Once all required enzyme activities are detected, the next step is to measure the production of succinate in vivo. Triplicate shake flask cultures are grown aerobically, anaerobically or microaerobically, depending on the conditions required, and periodic samples taken. Organic acids present in the culture supernatants are analyzed by HPLC using the Aminex AH-87X column. The elution time of succinate will be determined using a standard purchased from a chemical supplier.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples and embodiments provided above, it should be understood that various modifications can be made without departing from the spirit of the invention.

What is claimed is:

1. A non-naturally occurring microbial organism comprising:
   (a) a methanol metabolic pathway, wherein said non-naturally occurring microbial organism comprises at least one exogenous nucleic acid encoding a methanol metabolic pathway enzyme expressed in a sufficient amount to enhance the availability of reducing equivalents in the presence of methanol or metabolize methanol as a carbon source for biosynthesis of succinate, wherein said methanol metabolic pathway comprises:
      (i) a methanol methyltransferase and a methylenetetrahydrofolate reductase;
      (ii) a methanol dehydrogenase; or
      (iii) a methanol dehydrogenase and a formaldehyde activating enzyme; and
   (b) a succinate pathway comprising exogenous nucleic acids wherein at least one of said exogenous nucleic acids is a heterologous nucleic acid encoding a succinate pathway enzyme expressed in a sufficient amount to produce succinate, said succinate pathway comprising:
      (i) a phosphoenolpyruvate (PEP) carboxylase or a PEP carboxykinase, a malate dehydrogenase, a fumarase, and a fumarate reductase;
      (ii) a pyruvate carboxylase, a malate dehydrogenase, a fumarase, and a fumarate reductase; or
      (iii) a malic enzyme, a fumarase, and a fumarate reductase.

2. The non-naturally occurring microbial organism of claim 1, wherein the non-naturally occurring microbial organism comprises two, three, or four heterologous nucleic acids, each encoding a succinate pathway enzyme.

3. The non-naturally occurring microbial organism of claim 1, wherein the methanol metabolic pathway comprises
   (i) a methanol methyltransferase, a methylenetetrahydrofolate reductase, a methylenetetrahydrofolate dehydrogenase, a methenyltetrahydrofolate cyclohydrolase, and a formyltetrahydrofolate deformylase;
   (ii) a methanol methyltransferase, a methylenetetrahydrofolate reductase, a methylenetetrahydrofolate dehydrogenase, a methenyltetrahydrofolate cyclohydrolase and a formyltetrahydrofolate synthetase;
   (iii) a methanol dehydrogenase, a methylenetetrahydrofolate dehydrogenase, a methenyltetrahydrofolate cyclohydrolase and a formyltetrahydrofolate deformylase;
   (iv) a methanol dehydrogenase, a methylenetetrahydrofolate dehydrogenase, a methenyltetrahydrofolate cyclohydrolase and a formyltetrahydrofolate synthetase;
   (v) a methanol dehydrogenase and a formaldehyde dehydrogenase;
   (vi) a methanol dehydrogenase, a S-(hydroxymethyl)glutathione synthase, a glutathione-dependent formaldehyde dehydrogenase and a S-formylglutathione hydrolase;
   (vii) a methanol dehydrogenase, a glutathione-dependent formaldehyde dehydrogenase and a S-formylglutathione hydrolase;
   (viii) a methanol dehydrogenase, a formaldehyde activating enzyme, a methylenetetrahydrofolate dehydrogenase, a methenyltetrahydrofolate cyclohydrolase and a formyltetrahydrofolate deformylase; or
   (ix) a methanol dehydrogenase, a formaldehyde activating enzyme, a methylenetetrahydrofolate dehydrogenase, a methenyltetrahydrofolate cyclohydrolase and a formyltetrahydrofolate synthetase.

4. The non-naturally occurring microbial organism of claim 1, wherein the methanol metabolic pathway further comprises a formate dehydrogenase, a formate hydrogen lyase, or hydrogenase.

5. The non-naturally occurring microbial organism of claim 1, wherein said non-naturally occurring microbial organism comprises two, three, four, five, six or seven heterologous nucleic acids, each encoding a methanol metabolic pathway enzyme.

6. The non-naturally occurring microbial organism of claim 1, wherein said at least one exogenous nucleic acid encoding a methanol metabolic pathway enzyme is a heterologous nucleic acid.

7. The non-naturally occurring microbial organism of claim 1, further comprising one or more gene disruptions, wherein said one or more gene disruptions occur in one or more endogenous genes encoding protein(s) or enzyme(s) involved in native production of ethanol, glycerol, acetate, lactate, formate, $CO_2$, and/or amino acids by said microbial organism, and wherein said one or more gene disruptions confer increased production of succinate in said microbial organism.

8. The non-naturally occurring microbial organism of claim 7, wherein said protein(s) or enzyme(s) is a pyruvate decarboxylase, an ethanol dehydrogenase, a glycerol dehydrogenase, a glycerol-3-phosphatase, a glycerol-3-phosphate dehydrogenase, a lactate dehydrogenase, an acetate kinase, a phosphotransacetylase, a pyruvate oxidase, a pyruvate:quinone oxidoreductase, a pyruvate formate lyase, an alcohol dehydrogenase, a lactate dehydrogenase, a pyruvate dehydrogenase, a pyruvate formate-lyase-2-ketobutyrate formate-lyase, a pyruvate transporter, a monocarboxylate transporter, a NADH dehydrogenase, a cytochrome oxidase, a pyruvate kinase, or any combination thereof.

9. The non-naturally occurring microbial organism of claim 1, wherein one or more endogenous enzymes involved in native production of ethanol, glycerol, acetate, lactate, formate, CO2 and/or amino acids by said microbial organism has attenuated enzyme activity or expression levels.

10. The non-naturally occurring microbial organism of claim 9, wherein said enzyme is a pyruvate decarboxylase, an ethanol dehydrogenase, a glycerol dehydrogenase, a glycerol-3-phosphatase, a glycerol-3-phosphate dehydrogenase, a lactate dehydrogenase, an acetate kinase, a phosphotransacetylase, a pyruvate oxidase, a pyruvate:quinone oxidoreductase, a pyruvate formate lyase, an alcohol dehydrogenase, a lactate dehydrogenase, a pyruvate dehydrogenase, a pyruvate formate-lyase-2-ketobutyrate formate-lyase, a pyruvate transporter, a monocarboxylate transporter, a NADH dehydrogenase, a cytochrome oxidase, a pyruvate kinase, or any combination thereof.

11. The non-naturally occurring microbial organism of claim 1, further comprising a formaldehyde assimilation pathway, wherein said non-naturally occurring microbial organism comprises at least one exogenous nucleic acid encoding a formaldehyde assimilation pathway enzyme expressed in a sufficient amount to produce an intermediate of glycolysis and/or a metabolic pathway that can be used in the formation of biomass, and wherein said formaldehyde assimilation pathway comprises
   (i) a hexulose-6-phosphate synthase and a 6-phospho-3-hexuloisomerase, wherein optionally the intermediate is a hexulose-6-phosphate, a fructose-6-phosphate, or a combination thereof; or (ii) a dihydroxyacetone synthase and a dihydroxyacetone-phosphate kinase, wherein optionally the intermediate is a dihydroxyacetone, a dihydroxyacetone phosphate, or a combination thereof.

12. The non-naturally occurring microbial organism of claim 11, wherein the non-naturally occurring microbial organism comprises two exogenous nucleic acids, each encoding a formaldehyde assimilation pathway enzyme.

13. The non-naturally occurring microbial organism of claim 1, wherein said non-naturally occurring microbial organism is in a substantially anaerobic culture medium.

14. A method for producing succinate, comprising culturing the organism of claim 1 under conditions and for a sufficient period of time to produce succinate
wherein optionally the organism is a Crabtree positive, eukaryotic organism, and wherein the organism is cultured in a culture medium comprising glucose.

15. A method of producing formaldehyde, comprising culturing the organism of claim 1 under conditions and for a sufficient period of time to produce formaldehyde, and optionally wherein the formaldehyde is consumed to provide a reducing equivalent or to incorporate into succinate or target product.

16. A method of producing an intermediate of glycolysis and/or an intermediate of a metabolic pathway that can be used in the formation of biomass, comprising culturing the organism of claim 11 under conditions and for a sufficient period of time to produce the intermediate, and optionally wherein the intermediate is consumed to provide a reducing equivalent or to incorporate into succinate or target product.

17. The non-naturally occurring microbial organism of claim 11, wherein at least one of said exogenous nucleic acids is a heterologous nucleic acid.

18. The non-naturally occurring microbial organism of claim 12, wherein the two exogenous nucleic acids are heterologous nucleic acids, each encoding a formaldehyde assimilation pathway enzyme.

19. The non-naturally occurring microorganism of claim 1, wherein said non-naturally occurring microbial organism is selected from the group consisting of:
(i) *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*; or
(ii) *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus,* and *Rhizopus oryzae.*

* * * * *